United States Patent
Wicher et al.

(10) Patent No.: US 12,258,414 B2
(45) Date of Patent: Mar. 25, 2025

(54) ANTI-CD98hc VNARs FOR CROSSING THE BLOOD BRAIN BARRIER AND TYPE IV VNAR LIBRARIES

(71) Applicant: Ossianix, Inc., Philadelphia, PA (US)

(72) Inventors: Krzysztof Bartlomiej Wicher, Cambridge (GB); Jaroslaw Michal Szary, Cambridge (GB); Julia Lynn Rutkowski, Bryn Mawr, PA (US); Fabrizio Comper, Knebworth (GB); Pawel Stocki, Royston (GB)

(73) Assignee: Ossianix, Inc., Philadelphia, PA (US)

( * ) Notice: Subject to any disclaimer, the term of this patent is extended or adjusted under 35 U.S.C. 154(b) by 700 days.

(21) Appl. No.: 17/255,378

(22) PCT Filed: Jun. 19, 2019

(86) PCT No.: PCT/US2019/038021
§ 371 (c)(1),
(2) Date: Dec. 22, 2020

(87) PCT Pub. No.: WO2019/246288
PCT Pub. Date: Dec. 26, 2019

(65) Prior Publication Data
US 2022/0177597 A1 Jun. 9, 2022

Related U.S. Application Data

(60) Provisional application No. 62/688,966, filed on Jun. 22, 2018.

(51) Int. Cl.
| | | |
|---|---|---|
| C07K 16/28 | (2006.01) | |
| A61K 39/00 | (2006.01) | |
| A61P 35/00 | (2006.01) | |
| C40B 30/04 | (2006.01) | |

(52) U.S. Cl.
CPC .......... *C07K 16/2896* (2013.01); *A61P 35/00* (2018.01); *C07K 16/2881* (2013.01); *C07K 16/2887* (2013.01); *C40B 30/04* (2013.01); *A61K 2039/505* (2013.01); *C07K 2317/22* (2013.01); *C07K 2317/24* (2013.01); *C07K 2317/31* (2013.01); *C07K 2317/33* (2013.01); *C07K 2317/526* (2013.01); *C07K 2317/565* (2013.01); *C07K 2317/569* (2013.01); *C07K 2317/92* (2013.01)

(58) Field of Classification Search
CPC ............ C07K 16/2896; C07K 16/2881; C07K 16/2887; C07K 2317/22; C07K 2317/24; C07K 2317/31; C07K 2317/33; C07K 2317/526; C07K 2317/565; C07K 2317/569; C07K 2317/92; C07K 2317/90; A61P 35/00; C40B 30/04; A61K 2039/505
See application file for complete search history.

(56) References Cited

U.S. PATENT DOCUMENTS

| | | | |
|---|---|---|---|
| 8,865,431 B2 * | 10/2014 | Dooley | .............. A61P 37/02 435/71.1 |
| 10,479,990 B2 | 11/2019 | Hasler et al. | |
| 2020/0115720 A1 | 4/2020 | Quintana et al. | |

FOREIGN PATENT DOCUMENTS

| | | |
|---|---|---|
| WO | 199811125 A1 | 3/1998 |
| WO | 2006068867 A1 | 6/2006 |
| WO | 2007140371 A2 | 12/2007 |
| WO | 2015200883 A2 | 12/2015 |
| WO | 2016077840 A2 | 5/2016 |
| WO | 2016094566 A2 | 6/2016 |
| WO | 2018031424 A1 | 2/2018 |
| WO | 2019089395 A1 | 5/2019 |

OTHER PUBLICATIONS

Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
MacCallum et al., 1996, J. Mol. Biol. 262: 732-745 (Year: 1996).*
Greenspan et al. 1999 Defining epitopes: It's not as easy as it seems; Nature Biotechnology, 17:936-937 (Year: 1999).*

(Continued)

*Primary Examiner* — Vanessa L. Ford
*Assistant Examiner* — Danaya L Middleton
(74) *Attorney, Agent, or Firm* — Wilson IP Law; M. Lisa Wilson

(57) ABSTRACT

The present invention relates to CD98hc binding moieties with high specificity and with ability to cross the blood brain barrier (BBB). Such moieties may be used alone or as components in specific conjugates that target the amino acid transporter complexes formed with a light chain and CD98hc. The invention relates more specifically to VNAR single chain antibodies derived from nurse shark that bind to CD98hc, compounds and compositions comprising a CD98hc-specific binding moiety, diagnostic and therapeutic methods of use in vitro or in vivo, e.g., to diagnose, treat and/or prevent a pathological condition, disorder or disease in which it is beneficial to deliver a heterologous biomolecule across the blood brain barrier by association with a CD98hc-specific VNAR binding moiety. The invention also includes Type IV semi-synthetic VNAR libraries derived from shark VNARs for selection of binding moieties that specifically bind to a molecular or cellular target of interest.

16 Claims, 14 Drawing Sheets
Specification includes a Sequence Listing.

(56) References Cited

OTHER PUBLICATIONS

Bork. Powers and Pitfalls in Sequence Analysis: The 70% Hurdle. Genome Research, 2000, 10:398-400 (Year: 2000).*
Vajdos et al., 2002, J. Mol. Biol. 320: 415-428 (Year: 2002).*
Paul, Fundamental Immunology, 2003, 5th Edition, Raven Press, New York, Chapter 3, pp. 109-147 (Year: 2003).*
Casset et al., 2003, Biochemical and Biophysical Research Communications 307:198-205 (Year: 2003).*
Sela-Culang et al., 2013, Frontiers in Immunology 4(302): 1-13 (Year: 2013).*
Feng et al., Antibody Therapeutics, 2019, vol. 2, No. 1 1-11 (Year: 2019).*
Ahmad, et al., "scFv Antibody: Principles and clinical application," Clinical and Developmental Immunology, vol. 2012, Article ID 980250, 15 pages, doi 10.155/2012/980250.
Boado, R.J., et al., "Selective expression of the large neutral amino acid transporter at the blood-brain barrier", Proc. Natl. Acad. Sci., 96(21): 12079-84 (1999).
Cantor, J.M., and Ginsberg, M. H., "CD98 at the crossroads of adaptive immunity and cancer", J Cell Sci. 125 (6):1373-1382 (2012).
Feng, M., et al., "Construction and next-generation sequencing analysis of a large phage-displaced VNAR single-domain antibody library for six naïve nurse sharks", Antibody Therapeutics 2(1):1-11 (2019).
Feral, C. C., et al., "CD98hc (SLC3A2) mediates integrin signaling", Proc. Natl. Acad. Sci. 102(2):355-360 (2005).
Fotiadis D, et al., "The SLC3 and SLC7 families of amino acid transporters", Mol Aspects Med. 34(2-3):139-58 (2013).
Gynther, M., et al., "Large neutral amino acid transporter enables brain drug delivery via prodrugs", J. Med. Chem. 51 (4): 932-936 (2008).
Hawkins, R. A., "Structure of the Blood-Brain Barrier and its Role in the Transport of Amino Acids", J. Nutr. 136: 218S-226S (2006).
Ip, H., and Sethi, T., "CD98 signals controlling tumorigenesis", Int J Biochem & Cell Biol. 81(Pt A):148-150 (2016).

Killian, D.M., et al., "Targeting the cerebrovascular large neutral amino acid transporter (LAT1) isoform using a novel disulfide-based brain drug delivery system", Drug Deliv 14:25-31 (2007).
Liu, J.L., et al., "Selection of cholera toxin specific IgNAR single-domain antibodies from a naïve shark library", Molecular Immunology 44(7):1775-1783 (2007).
Muller, M.R., et al., "Improving the pharmacokinetic properties of biologics by fusion to an anti-HSA shark VNAR domain", MAbs 4(6):673-685 (2012).
Niewoehner J, et al., "Increased brain penetration and potency of a therapeutic antibody using a monovalent molecular shuttle", Neuron 81(1):49-60 (2014).
Pardridge, W. M., ""Drug transport across the blood-brain barrier"", Journal of Cerebral Blood Flow & Metabolism 32:1959-1972 (2012).
Pardridge,W.M. "The Blood-Brain Barrier: Bottleneck in Brain Drug Development" vol. 2, Jan. 3-14, 2005, The American Society for Experimental Neuro Therapeutics, Inc.
Pardridge, W.M., "Re-engineering therapeutic antibodies for Alzheimer's disease as blood-brain barrier penetrating bi-specific antibodies", Expert Opinion on Biological Therapy 16(12): 1455-1468 (2016).
Streltsov, V.A., et al., "Structural evidence for evolution of shark Ig new antigen receptor variable domain antibodies from a cell-surface receptor", PNAS 101(34):12444-12449 (2004).
Weiner, et al., "Antibody-based immunotherapy of cancer," Cell, vol. 148, Mar. 16, 2012, pp. 1081-1084.
Yu, Y.J., et al., "Boosting brain uptake of a therapeutic antibody by reducing its affinity for a transcytosis target", Sci Transl Med 25(3):84ra44 (2011).
Zielonka, S., et al., "Structural insights and biomedical potential of IgNAR scaffolds from sharks", MAbs 7(1):15-25 (2015).
Zuchero, Y.J., et al., "Discovery of novel blood-brain barrier targets to enhance brain uptake of therapeutic antibodies", Neuron. 89(1):70-82 (2016).
Pardridge, W.M., "Drug Targeting to the Brain" Pharmaceutical Research, vol. 24, No. 9, Sep. 2007, 12 pages.
Pardridge, W.M., "Drug and Gene Delivery tot he Brain: The Vascular Route" Neuron, vol. 36, 555-558, Nov. 14, 2002, 4 pages.

* cited by examiner

A

ARVDQTPQTITKEEGESLTINCVLRVHGRALASTSWYRKKS
GSTREETISKGGRYVETVNSGSKSFSLRINDLTVEDSGTYR
CNVYGLSFGDIEGVKKIDVYGDGTAVTVNA

B

ARVDQTPQTITKEEGESLTINCVLRXXXXALASTSWYRKKS
GSTREETISKGGRYVETVNSGSKSFSLRINDLTVEDSGTYR
CNVYXXXXXXXXXXXXDVYGDGTAVTVNA

SEQUENCE LISTING

```
<160> NUMBER OF SEQ ID NOS: 376

<210> SEQ ID NO 1
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Thr Arg Glu Glu Thr Ile Ser Lys Gly
1               5

<210> SEQ ID NO 2
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ser Arg Glu Glu Thr Ile Ser Lys Gly
1               5

<210> SEQ ID NO 3
<211> LENGTH: 6
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 3

Asn Ser Gly Ser Lys Ser
1               5

<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="E" or "F" or "G" or "I"
<220> FEATURE:
<221> NAME/KEY: VARIANT
<222> LOCATION: (4)..(4)
<223> OTHER INFORMATION: /replace="F" or "I" or "L" or "R" or "Y"
<220> FEATURE:
<221> NAME/KEY: VARIANT
<222> LOCATION: (5)..(5)
<223> OTHER INFORMATION: /replace="L" or "P" or "R" or "S" or "V" or "Y"
<220> FEATURE:
<221> NAME/KEY: VARIANT
<222> LOCATION: (6)..(6)
<223> OTHER INFORMATION: /replace="E" or "F" or "I" or "S" or "Y"
<220> FEATURE:
<221> NAME/KEY: VARIANT
<222> LOCATION: (7)..(7)
<223> OTHER INFORMATION: /replace="G" or "I" or "P" or "S" or "V"
<220> FEATURE:
<221> NAME/KEY: VARIANT
<222> LOCATION: (8)..(8)
<223> OTHER INFORMATION: /replace="D" or "E" or "L" or "Q" or "S" or "T"
<220> FEATURE:
<221> NAME/KEY: VARIANT
<222> LOCATION: (9)..(9)
<223> OTHER INFORMATION: /replace="E" or "F" or "I" or "K" or "P" or "V"
<220> FEATURE:
<221> NAME/KEY: VARIANT
<222> LOCATION: (10)..(10)
<223> OTHER INFORMATION: /replace="E" or "K" or "N" or "T"
<220> FEATURE:
<221> NAME/KEY: VARIANT
<222> LOCATION: (11)..(11)
<223> OTHER INFORMATION: /replace="G" or "I" or "K" or "Q" or "V"
<220> FEATURE:
<221> NAME/KEY: VARIANT
<222> LOCATION: (12)..(12)
<223> OTHER INFORMATION: /replace="K" or "L" or "R" or "V" or "Y"
<220> FEATURE:
<221> NAME/KEY: VARIANT
<222> LOCATION: (13)..(13)
<223> OTHER INFORMATION: /replace="G" or "H" or "K" or "P" or "Q" or "Y"
<220> FEATURE:
<221> NAME/KEY: VARIANT
<222> LOCATION: (14)..(14)
<223> OTHER INFORMATION: /replace="E" or "F" or "G" or "K" or "P" or "S"
      or "T" or "Y"
<220> FEATURE:
<221> NAME/KEY: VARIANT
<222> LOCATION: (15)..(15)
<223> OTHER INFORMATION: /replace="H" or "I" or "N" or "Q" or "R"
<220> FEATURE:
<221> NAME/KEY: SITE
<222> LOCATION: (1)..(17)
<223> OTHER INFORMATION: /note="Variant residues given in the sequence
      have no preference with respect to those in the annotations
      for variant positions"
```

```
<400> SEQUENCE: 4

Val Tyr Ala Glu His Ala Phe Ala Cys Asp Ala Ala Glu Asp Phe Asp
1               5                   10                  15

Val

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="D" or "F" or "H" or "K" or "N" or "S"
      or "W"
<220> FEATURE:
<221> NAME/KEY: VARIANT
<222> LOCATION: (4)..(4)
<223> OTHER INFORMATION: /replace="V"
<220> FEATURE:
<221> NAME/KEY: VARIANT
<222> LOCATION: (5)..(5)
<223> OTHER INFORMATION: /replace="G" or "E" or "K" or "L" or "M" or "Q"
      or "R"
<220> FEATURE:
<221> NAME/KEY: VARIANT
<222> LOCATION: (6)..(6)
<223> OTHER INFORMATION: /replace="A" or "G" or "H" or "I" or "K" or "L"
      or "M" or "N" or "Q" or "R" or "S" or "T" or "W" or "Y"
<220> FEATURE:
<221> NAME/KEY: VARIANT
<222> LOCATION: (7)..(7)
<223> OTHER INFORMATION: /replace="E" or "K" or "L" or "M" or "V" or "W"
      or "Y"
<220> FEATURE:
<221> NAME/KEY: VARIANT
<222> LOCATION: (8)..(8)
<223> OTHER INFORMATION: /replace="A" or "G" or "H" or "K" or "M" or "P"
      or "S" or "T"
<220> FEATURE:
<221> NAME/KEY: VARIANT
<222> LOCATION: (9)..(9)
<223> OTHER INFORMATION: /replace="A" or "D" or "E" or "F" or "G" or "H"
      or "K" or "L" or "M" or "N" or "Q" or "S" or "Y"
<220> FEATURE:
<221> NAME/KEY: VARIANT
<222> LOCATION: (10)..(10)
<223> OTHER INFORMATION: /replace="A" or "G" or "H" or "K" or "L" or "M"
      or "Q" or "R" or "V" or "Y" or "W"
<220> FEATURE:
<221> NAME/KEY: VARIANT
<222> LOCATION: (11)..(11)
<223> OTHER INFORMATION: /replace="E" or "R" or "W"
<220> FEATURE:
<221> NAME/KEY: VARIANT
<222> LOCATION: (12)..(12)
<223> OTHER INFORMATION: /replace="L" or "P" or "W" or "Y"
<220> FEATURE:
<221> NAME/KEY: VARIANT
<222> LOCATION: (13)..(13)
<223> OTHER INFORMATION: /replace="G" or "N"
<220> FEATURE:
<221> NAME/KEY: VARIANT
<222> LOCATION: (14)..(14)
<223> OTHER INFORMATION: /replace="Q"
<220> FEATURE:
<221> NAME/KEY: VARIANT
<222> LOCATION: (15)..(15)
<223> OTHER INFORMATION: /replace="L"
<220> FEATURE:
<221> NAME/KEY: SITE
<222> LOCATION: (1)..(17)
<223> OTHER INFORMATION: /note="Variant residues given in the sequence
``` have no preference with respect to those in the annotations for variant positions"

<400> SEQUENCE: 5

Val Tyr Gly Leu Ser Phe Gly Asp Ile Glu Gly Val Lys Lys Ile Asp
1               5                   10                  15

Val

<210> SEQ ID NO 6
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 6x His tag"

<400> SEQUENCE: 6

His His His His His His
1               5

<210> SEQ ID NO 7
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

Ala Arg Val Asp Gln Thr Pro Gln Thr Ile Thr Lys Glu Glu Gly Glu
1               5                   10                  15

Ser Leu Thr Ile Asn Cys Val Leu Arg Val His Gly Arg Ala Leu Ala
            20                  25                  30

Ser Thr Ser Trp Tyr Arg Lys Lys Ser Gly Ser Thr Arg Glu Glu Thr
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Gly Leu Ser Ser Gly Asp Ile Glu Gly Val
                85                  90                  95

Lys Lys Ile Asp Val Tyr Gly Asp Gly Thr Ala Val Thr Val Asn Ala
            100                 105                 110

<210> SEQ ID NO 8
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

Ala Arg Val Asp Gln Thr Pro Gln Thr Ile Thr Lys Glu Glu Gly Glu
1               5                   10                  15

Ser Leu Thr Ile Asn Cys Val Leu Arg His Asn Tyr Ser Ala Leu Ala
            20                  25                  30

Ser Thr Ser Trp Tyr Arg Lys Lys Ser Gly Ser Thr Arg Glu Glu Thr
        35                  40                  45

```
Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Gly Ile Ser Phe Ile Glu Glu Lys Ile Arg
                85                  90                  95

Tyr Asp Phe Asp Val Tyr Gly Asp Gly Thr Ala Val Thr Val Asn Ala
                100                 105                 110
```

<210> SEQ ID NO 9
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Ala Leu
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Val Gln Asp Leu Arg Asp Asp Cys Phe Phe Arg
                85                  90                  95

Asp Val Tyr Gly Gly Gly Thr Ala Val Thr Val Asn Ala
                100                 105
```

<210> SEQ ID NO 10
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

```
Ala Arg Val Asp Gln Thr Pro Gln Thr Ile Thr Lys Glu Glu Gly Glu
1               5                   10                  15

Ser Leu Thr Ile Asn Cys Val Leu Arg Thr His Ser Asn Ala Leu Ala
                20                  25                  30

Ser Thr Ser Trp Tyr Arg Lys Lys Ser Gly Ser Thr Arg Glu Glu Thr
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Ala Phe Leu Glu Ile Gln Pro Asn Ile Tyr
                85                  90                  95

His Glu Phe Asp Val Tyr Gly Asp Gly Thr Ala Val Thr Val Asn Ala
                100                 105                 110
```

```
<210> SEQ ID NO 11
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Ala Arg Val Asp Gln Thr Pro Gln Thr Ile Thr Lys Glu Gly Glu
1               5                   10                  15

Ser Leu Thr Ile Asn Cys Val Leu Arg Tyr Asn Asn Pro Ala Leu Ala
            20                  25                  30

Ser Thr Ser Trp Tyr Arg Lys Lys Ser Gly Ser Thr Arg Glu Glu Thr
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Phe Phe Pro Ser Phe Leu Val Asp Lys Leu
                85                  90                  95

Gln Ser His Asp Val Tyr Gly Asp Gly Thr Ala Val Thr Val Asn Ala
            100                 105                 110

<210> SEQ ID NO 12
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asn Cys Ala Leu Ser
            20                  25                  30

Thr Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val His Phe Phe Pro Ser Phe Cys Asn Ser Thr Ser
                85                  90                  95

Ile Arg Ser Val Asp Val Tyr Gly Gly Gly Thr Val Val Thr Val Asn
            100                 105                 110

Ala

<210> SEQ ID NO 13
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13
```

```
Ala Arg Val Asp Gln Thr Pro Gln Thr Ile Thr Lys Glu Glu Gly Glu
1               5                   10                  15

Ser Leu Thr Ile Asn Cys Val Leu Arg Thr Gln Asp Pro Ala Leu Ala
            20                  25                  30

Ser Thr Ser Trp Tyr Arg Lys Lys Ser Gly Ser Thr Arg Glu Glu Thr
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Phe Leu Leu Ala Pro Thr Lys Thr Lys Leu
                85                  90                  95

Gln Gly Ile Asp Val Tyr Gly Asp Gly Thr Ala Val Thr Val Asn Ala
            100                 105                 110
```

<210> SEQ ID NO 14
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

```
Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Ala Arg Gly Trp Arg Thr Leu Asn Tyr Leu Cys
                85                  90                  95

Asp Val Arg Thr Gly Glu Trp Ser Cys Val Trp Arg Ala Ala Cys
            100                 105                 110

Gly Asp Gly Thr Ala Val Thr Val Asn Ala
            115                 120
```

<210> SEQ ID NO 15
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

```
Ala Arg Val Asp Gln Thr Pro Gln Thr Ile Ala Arg Glu Glu Gly Glu
1               5                   10                  15

Ser Val Thr Ile Asn Cys Val Val Arg Asp Ser Asn Arg Ala Leu Ala
            20                  25                  30

Ser Thr Ser Trp Cys Ser Glu Lys Tyr Val Ser Thr Arg Glu Glu Ser
        35                  40                  45

Ile Ser Lys Gly Gly Arg Tyr Val Glu Thr Val Asn Ser Gly Ser Lys
```

```
Ser Phe Ser Leu Arg Ile Asn Asp Leu Thr Val Glu Asp Ser Gly Thr
 65                  70                  75                  80

Tyr Arg Cys Asn Val Tyr Phe Phe Pro Ser Phe Glu Val Asp Val Leu
                     85                  90                  95

Gln Thr Asn Asp Val Tyr Gly Asp Gly Thr Ala Val Thr Val Asn Ala
                    100                 105                 110
```

<210> SEQ ID NO 16
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

```
Ala Arg Val Asp Gln Thr Pro Gln Thr Ile Thr Lys Glu Gly Glu
 1               5                  10                  15

Ser Leu Thr Ile Asn Cys Val Leu Arg Gly Glu Phe Tyr Ala Leu Ala
                20                  25                  30

Ser Thr Ser Trp Tyr Arg Lys Lys Ser Gly Ser Thr Arg Glu Glu Thr
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Tyr Gly Tyr Arg Ile Phe Ser Pro Glu Val Lys
                     85                  90                  95

Gly Pro Asn Asp Val Tyr Gly Asp Gly Thr Ala Val Thr Val Asn Ala
                    100                 105                 110
```

<210> SEQ ID NO 17
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

```
Ala Arg Val Asp Gln Thr Pro Gln Thr Ile Thr Lys Glu Gly Glu
 1               5                  10                  15

Ser Leu Thr Ile Asn Cys Val Leu Arg Arg Asn Phe Gln Leu Ala Ser
                20                  25                  30

Thr Ser Trp Tyr Arg Lys Lys Ser Gly Ser Thr Arg Glu Glu Thr Ile
            35                  40                  45

Ser Lys Gly Gly Arg Tyr Val Glu Thr Val Asn Ser Gly Ser Lys Ser
 50                  55                  60

Phe Ser Leu Arg Ile Asn Asp Leu Thr Val Glu Asp Ser Gly Thr Tyr
 65                  70                  75                  80

Arg Cys Asn Val Tyr Gly Phe Val Glu Phe Ala Lys Asn Ile Val Glu
                     85                  90                  95

Phe Ile Asp Val Tyr Gly Asp Gly Thr Ala Val Thr Val Asn Ala
                    100                 105                 110
```

<210> SEQ ID NO 18

```
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18
```

Ala Arg Val Asp Gln Thr Pro Gln Thr Ile Thr Lys Glu Glu Gly Glu
1               5                   10                  15

Ser Leu Thr Ile Asn Cys Val Leu Arg Val Glu Thr Arg Ala Leu Ala
            20                  25                  30

Ser Thr Ser Trp Tyr Arg Lys Lys Ser Gly Ser Thr Arg Glu Glu Thr
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Ile Arg His Tyr Ser Glu Phe Thr Gln Ala
                85                  90                  95

Pro Phe Arg Asp Val Tyr Gly Asp Gly Thr Ala Val Thr Val Asn Ala
            100                 105                 110

```
<210> SEQ ID NO 19
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19
```

Ala Arg Val Asp Gln Thr Pro Gln Thr Ile Thr Lys Glu Glu Gly Glu
1               5                   10                  15

Ser Leu Thr Ile Asn Cys Val Leu Arg Val His Gly Cys Ala Leu Ala
            20                  25                  30

Ser Thr Ser Trp Tyr Arg Lys Lys Ser Gly Ser Thr Arg Glu Glu Thr
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Gly Leu Ser Phe Val Asp Ile Glu Gly Val
                85                  90                  95

Lys Lys Ile Asp Val Tyr Gly Asp Gly Thr Ala Val Thr Val Asn Ala
            100                 105                 110

```
<210> SEQ ID NO 20
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20
```

Ala Arg Val Asp Gln Thr Pro Gln Thr Ile Thr Lys Glu Glu Gly Glu
1               5                   10                  15

```
Ser Leu Thr Ile Asn Cys Val Leu Arg Val His Gly Arg Ala Leu Ala
             20                  25                  30

Ser Thr Ser Trp Tyr Arg Lys Lys Ser Gly Ser Thr Glu Glu Thr
         35                  40                  45

Ile Ser Lys Gly Gly Arg Tyr Val Glu Thr Val Asn Ser Gly Ser Lys
     50                  55                  60

Ser Phe Ser Leu Arg Ile Asn Asp Leu Thr Val Glu Asp Ser Gly Thr
65                  70                  75                  80

Tyr Arg Cys Asn Val Tyr Gly Leu Ser Phe Gly Asp Ile Glu Gly Val
                 85                  90                  95

Lys Lys Ile Asp Val Tyr Gly Asp Gly Thr Ala Val Thr Val Asn Ala
            100                 105                 110
```

<210> SEQ ID NO 21
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

```
Pro Gly Val Asp Gln Thr Glu Gln Thr Ile Lys Lys Glu Glu Gly Glu
1               5                   10                  15

Ser Val Thr Ile Lys Cys Val Met Arg Val Lys Tyr Pro Ala Leu Ala
             20                  25                  30

Ser Thr Ser Arg Tyr Arg Lys Lys Ser Gly Ser Arg Glu Glu Thr Ile
         35                  40                  45

Ser Lys Gly Gly Arg Tyr Val Glu Thr Val Asn Tyr Ser Ser Lys Ser
     50                  55                  60

Ile Ser Val Arg Ile Asn Asp Met Thr Val Glu Asp Ser Gly Arg Tyr
65                  70                  75                  80

Arg Cys Asn Val Tyr Glu Glu Tyr Ala Val Asp Cys Asp Ala Leu Val
                 85                  90                  95

Tyr Gln Asp Val Tyr Gly Asp Gly Thr Ala Val Thr Val Asn Ala
            100                 105                 110
```

<210> SEQ ID NO 22
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
             20                  25                  30

Ser Thr Tyr Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
     50                  55                  60

Ser Phe Ser Leu Arg Ile Asn Asp Leu Val Val Glu Asp Ser Gly Thr
65                  70                  75                  80

Tyr Arg Cys Lys Val Gly Asn Tyr Cys Ile Arg Leu Cys Tyr Asp Met
```

```
                    85                  90                  95

Lys Phe Ala Val Asp Val Tyr Gly Gly Gly Thr Ala Val Thr Val Asn
                100                 105                 110

Ala

<210> SEQ ID NO 23
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Ala Leu
                35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Val Tyr Asp Leu Arg Asp Asp Cys Phe Phe Arg
                85                  90                  95

Asp Val Tyr Gly Gly Gly Thr Ala Val Thr Val Asn Ala
                100                 105

<210> SEQ ID NO 24
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Asn
                35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Lys Val Val Phe Lys Leu Phe Ser Gly Arg Ala Cys Ala
                85                  90                  95

Gly Glu Lys Asp Val Tyr Gly Gly Gly Thr Val Thr Val Asn Ala
                100                 105                 110

<210> SEQ ID NO 25
<211> LENGTH: 7
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 25

Val His Gly Arg Ala Leu Ala
1               5

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

His Asn Tyr Ser Ala Leu Ala
1               5

<210> SEQ ID NO 27
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Asp Ser Asn Cys Ala Leu Ser
1               5

<210> SEQ ID NO 28
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Thr His Ser Asn Ala Leu Ala
1               5

<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Tyr Asn Asn Pro Ala Leu Ala
1               5

<210> SEQ ID NO 30
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 30

Asp Asn Asn Cys Ala Leu Ser
1               5

<210> SEQ ID NO 31
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Thr Gln Asp Pro Ala Leu Ala
1               5

<210> SEQ ID NO 32
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Asp Ala Ser Tyr Ala Leu Gly
1               5

<210> SEQ ID NO 33
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Asp Ser Asn Arg Ala Leu Ala
1               5

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Glu Phe Tyr Ala Leu Ala
1               5

<210> SEQ ID NO 35
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Arg Asn Phe Gln Leu Ala
1               5
```

<210> SEQ ID NO 36
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Val Glu Thr Arg Ala Leu Ala
1               5

<210> SEQ ID NO 37
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Val His Gly Cys Ala Leu Ala
1               5

<210> SEQ ID NO 38
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Val His Gly Arg Ala Leu Ala
1               5

<210> SEQ ID NO 39
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Val Lys Tyr Pro Ala Leu Ala
1               5

<210> SEQ ID NO 40
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Asp Ser Asn Cys Ala Leu Pro
1               5

<210> SEQ ID NO 41
<211> LENGTH: 7

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Asp Ser Asn Cys Ala Leu Ser
1               5

<210> SEQ ID NO 42
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Asp Ser Asn Cys Ala Leu Ser
1               5

<210> SEQ ID NO 43
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Thr Arg Glu Glu Thr Ile Ser Lys Gly
1               5

<210> SEQ ID NO 44
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Thr Arg Glu Glu Thr Ile Ser Lys Gly
1               5

<210> SEQ ID NO 45
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Thr Asn Glu Ala Leu Ile Ser Lys Gly
1               5

<210> SEQ ID NO 46
<211> LENGTH: 9
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 46

Thr Arg Glu Glu Thr Ile Ser Lys Gly
1               5

<210> SEQ ID NO 47
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Thr Arg Glu Glu Thr Ile Ser Lys Gly
1               5

<210> SEQ ID NO 48
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Thr Asn Glu Glu Asn Ile Ser Lys Gly
1               5

<210> SEQ ID NO 49
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Thr Arg Glu Glu Thr Ile Ser Lys Gly
1               5

<210> SEQ ID NO 50
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Thr Asn Glu Glu Ser Ile Ser Lys Gly
1               5

<210> SEQ ID NO 51
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51
```

Thr Arg Glu Glu Ser Ile Ser Lys Gly
1               5

<210> SEQ ID NO 52
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Thr Arg Glu Glu Thr Ile Ser Lys Gly
1               5

<210> SEQ ID NO 53
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Thr Arg Glu Glu Thr Ile Ser Lys Gly
1               5

<210> SEQ ID NO 54
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Thr Arg Glu Glu Thr Ile Ser Lys Gly
1               5

<210> SEQ ID NO 55
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Thr Arg Glu Glu Thr Ile Ser Lys Gly
1               5

<210> SEQ ID NO 56
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Thr Arg Glu Glu Thr Ile Ser Lys Gly
1               5

```
<210> SEQ ID NO 57
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ser Arg Glu Glu Thr Ile Ser Lys Gly
1               5

<210> SEQ ID NO 58
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Thr Asn Glu Glu Ser Ile Ser Lys Gly
1               5

<210> SEQ ID NO 59
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Thr Asn Glu Ala Leu Ile Ser Lys Gly
1               5

<210> SEQ ID NO 60
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Thr Asn Glu Glu Asn Ile Ser Lys Gly
1               5

<210> SEQ ID NO 61
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Asn Ser Gly Ser Lys Ser
1               5

<210> SEQ ID NO 62
<211> LENGTH: 6
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Asn Ser Gly Ser Lys Ser
1               5

<210> SEQ ID NO 63
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Asn Ser Gly Ser Lys Ser
1               5

<210> SEQ ID NO 64
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Asn Ser Gly Ser Lys Ser
1               5

<210> SEQ ID NO 65
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Asn Ser Gly Ser Lys Ser
1               5

<210> SEQ ID NO 66
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Asn Ser Gly Ser Lys Ser
1               5

<210> SEQ ID NO 67
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

```
      Synthetic peptide"

<400> SEQUENCE: 67

Asn Ser Gly Ser Lys Ser
1               5

<210> SEQ ID NO 68
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Asn Ser Gly Ser Lys Ser
1               5

<210> SEQ ID NO 69
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Asn Ser Gly Ser Lys Ser
1               5

<210> SEQ ID NO 70
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Asn Ser Gly Ser Lys Ser
1               5

<210> SEQ ID NO 71
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Asn Ser Gly Ser Lys Ser
1               5

<210> SEQ ID NO 72
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72
```

Asn Ser Gly Ser Lys Ser
1               5

<210> SEQ ID NO 73
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Asn Ser Gly Ser Lys Ser
1               5

<210> SEQ ID NO 74
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Asn Ser Gly Ser Lys Ser
1               5

<210> SEQ ID NO 75
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Asn Tyr Ser Ser Lys Ser
1               5

<210> SEQ ID NO 76
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Asn Ser Gly Ser Lys Ser
1               5

<210> SEQ ID NO 77
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Asn Ser Gly Ser Lys Ser
1               5

```
<210> SEQ ID NO 78
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Asn Ser Gly Ser Lys Ser
1               5

<210> SEQ ID NO 79
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Val Tyr Gly Leu Ser Ser Gly Asp Ile Glu Gly Val Lys Lys Ile Asp
1               5                   10                  15

Val

<210> SEQ ID NO 80
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Val Tyr Gly Ile Ser Phe Ile Glu Glu Lys Ile Arg Tyr Asp Phe Asp
1               5                   10                  15

Val

<210> SEQ ID NO 81
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Val Val Gln Asp Leu Arg Asp Asp Cys Phe Phe Arg Asp Val
1               5                   10

<210> SEQ ID NO 82
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Val Tyr Ala Phe Leu Glu Ile Gln Pro Asn Ile Tyr His Glu Phe Asp
1               5                   10                  15

Val
```

```
<210> SEQ ID NO 83
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Val Tyr Phe Phe Pro Ser Phe Leu Val Asp Lys Leu Gln Ser His Asp
1               5                   10                  15

Val

<210> SEQ ID NO 84
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Val His Phe Phe Pro Ser Phe Cys Asn Ser Thr Ser Ile Arg Ser Val
1               5                   10                  15

Asp Val

<210> SEQ ID NO 85
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Val Tyr Phe Leu Leu Ala Pro Thr Lys Thr Lys Leu Gln Gly Ile Asp
1               5                   10                  15

Val

<210> SEQ ID NO 86
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Val Ala Arg Gly Trp Arg Thr Leu Asn Tyr Leu Cys Asp Val Arg Thr
1               5                   10                  15

Gly Glu Trp Ser Cys Val
            20

<210> SEQ ID NO 87
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 87

Val Tyr Phe Phe Pro Ser Phe Glu Val Asp Val Leu Gln Thr Asn Asp
1               5                   10                  15

Val

<210> SEQ ID NO 88
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Val Tyr Gly Tyr Arg Ile Phe Ser Pro Glu Val Lys Gly Pro Asn Asp
1               5                   10                  15

Val

<210> SEQ ID NO 89
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Val Tyr Gly Phe Val Glu Phe Ala Lys Asn Ile Val Glu Phe Ile Asp
1               5                   10                  15

Val

<210> SEQ ID NO 90
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Val Tyr Ile Arg His Tyr Ser Glu Phe Thr Gln Ala Pro Phe Arg Asp
1               5                   10                  15

Val

<210> SEQ ID NO 91
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Val Tyr Gly Leu Ser Phe Val Asp Ile Glu Gly Val Lys Lys Ile Asp
1               5                   10                  15

Val

<210> SEQ ID NO 92
<211> LENGTH: 17
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Val Tyr Gly Leu Ser Phe Gly Asp Ile Glu Gly Val Lys Lys Ile Asp
1               5                   10                  15
Val

<210> SEQ ID NO 93
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Val Tyr Glu Glu Tyr Ala Val Asp Cys Asp Ala Leu Val Tyr Gln Asp
1               5                   10                  15
Val

<210> SEQ ID NO 94
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Val Gly Asn Tyr Cys Ile Arg Leu Cys Tyr Asp Met Lys Phe Ala Val
1               5                   10                  15
Asp Val

<210> SEQ ID NO 95
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Val Val Tyr Asp Leu Arg Asp Asp Cys Phe Phe Arg Asp Val
1               5                   10

<210> SEQ ID NO 96
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Val Val Phe Lys Leu Phe Ser Gly Arg Ala Cys Ala Gly Glu Lys Asp
1               5                   10                  15
Val
```

```
<210> SEQ ID NO 97
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Gly Gly Gly Gly Ser
1               5

<210> SEQ ID NO 98
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Val Asn Gly Leu Ser Ser Gly Asp Lys Glu Gly Val Lys Lys Ile Asp
1               5                   10                  15

Val

<210> SEQ ID NO 99
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Val Asn Gly Leu Ser Ser Gly Asp Ile Glu Gly Val Lys Lys Leu Asp
1               5                   10                  15

Val

<210> SEQ ID NO 100
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Val Tyr Gly Leu Ser Ser Gly Asp Ser Glu Gly Val Lys Lys Ile Asp
1               5                   10                  15

Val

<210> SEQ ID NO 101
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101
```

```
Val Asn Gly Leu Ser Ser Gly Asp Gln Glu Gly Val Lys Lys Ile Asp
1               5                   10                  15

Val

<210> SEQ ID NO 102
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Val Tyr Gly Leu Met Asn Val Asp Ile Glu Gly Val Lys Lys Ile Asp
1               5                   10                  15

Val

<210> SEQ ID NO 103
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Val Asn Gly Leu Ser Ser Gly Asp Ile Glu Gly Val Lys Lys Ile Asp
1               5                   10                  15

Val

<210> SEQ ID NO 104
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Val Tyr Gly Leu Met Gln Gly Asp Ile Glu Gly Val Lys Lys Ile Asp
1               5                   10                  15

Val

<210> SEQ ID NO 105
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Val Asn Gly Arg Ser Phe Gly Asp Ile Glu Gly Val Lys Lys Ile Asp
1               5                   10                  15

Val

<210> SEQ ID NO 106
<211> LENGTH: 17
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 106

Val His Phe Leu Arg Phe Gly Asp Ile Glu Gly Val Lys Lys Ile Asp
1               5                   10                  15

Val

<210> SEQ ID NO 107
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Val Tyr Gly Gln Ser Phe Gly Asp Ile Glu Leu Val Lys Lys Ile Asp
1               5                   10                  15

Val

<210> SEQ ID NO 108
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Val Tyr Gly Leu Ser Phe Gly Leu Ile Glu Gly Val Lys Lys Ile Asp
1               5                   10                  15

Val

<210> SEQ ID NO 109
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Val Glu Gly Leu Ser Asn Gly Asp Ile Glu Glu Val Lys Lys Ile Asp
1               5                   10                  15

Val

<210> SEQ ID NO 110
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Val Trp Gly Leu Ser Phe Gly Asp Ile Glu Gly Val Lys Lys Ile Asp
1               5                   10                  15

Val
```

-continued

```
<210> SEQ ID NO 111
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Val Leu Gly Leu Ser Phe Gly Asp Trp Gly Val Lys Lys Ile Asp
1               5                   10                  15

Val

<210> SEQ ID NO 112
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Val Tyr Gly Leu Ser Tyr Gly Leu Phe Glu Gly Val Lys Lys Ile Asp
1               5                   10                  15

Val

<210> SEQ ID NO 113
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Val Tyr Gly Leu Ser Phe Gly Asp Phe Glu Gly Val Lys Lys Ile Asp
1               5                   10                  15

Val

<210> SEQ ID NO 114
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Val Tyr Gly Phe Ser Phe Gly Ser Ile Glu Gly Val Lys Lys Ile Asp
1               5                   10                  15

Val

<210> SEQ ID NO 115
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115
```

```
Val Arg Gly Leu Tyr Thr Gly Asp Ile Glu Gly Val Lys Lys Ile Asp
1               5                   10                  15

Val

<210> SEQ ID NO 116
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Val Tyr Gly Gln Ser Phe Gly Asp Ile Glu Gly Val Lys Lys Ile Asp
1               5                   10                  15

Val

<210> SEQ ID NO 117
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Val Tyr Gly Met Leu Phe Gly Asp Ile Glu Gly Val Lys Lys Ile Asp
1               5                   10                  15

Val

<210> SEQ ID NO 118
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Val Tyr Gly Leu Ser Tyr Gly Asp Ile Glu Gly Val Lys Lys Ile Asp
1               5                   10                  15

Val

<210> SEQ ID NO 119
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Val Tyr Gly Leu Ser Tyr Gly Asp Ile Gly Gly Val Lys Lys Ile Asp
1               5                   10                  15

Val

<210> SEQ ID NO 120
<211> LENGTH: 17
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 120

Val Tyr Gly Glu Ser Phe Gly Leu Ile Glu Gly Val Lys Lys Ile Asp
1               5                   10                  15

Val

<210> SEQ ID NO 121
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Val His Gly Leu Ser Phe Gln Asp Ile Glu Gly Val Lys Lys Ile Asp
1               5                   10                  15

Val

<210> SEQ ID NO 122
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Val Tyr Gly Leu Ser Phe Gly Asp Ile Ser Gly Val Lys Lys Ile Asp
1               5                   10                  15

Val

<210> SEQ ID NO 123
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Val Trp Gly Leu Ser Phe Gly Arg Ile Glu Gly Val Lys Lys Ile Asp
1               5                   10                  15

Val

<210> SEQ ID NO 124
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Val Tyr Gly Leu Gln Leu Gly Asp Ile Glu Gln Val Lys Lys Ile Asp
1               5                   10                  15

Val
```

```
<210> SEQ ID NO 125
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Val Tyr Gly Leu Ser Leu Gly Asp Ile Glu Gly Phe Lys Lys Ile Asp
1               5                   10                  15

Val

<210> SEQ ID NO 126
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Val Tyr Leu Leu Ser Phe Gly Asp Ile Glu Gly Val Gln Lys Ile Asp
1               5                   10                  15

Val

<210> SEQ ID NO 127
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Val Tyr Gly Leu Ser Phe Gly Asp Ile Leu Gly Val Lys Lys Ile Asp
1               5                   10                  15

Val

<210> SEQ ID NO 128
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Val Tyr Gly Leu Ser Val Gly Asp Ile Glu Gly Val Lys Lys Ile Asp
1               5                   10                  15

Val

<210> SEQ ID NO 129
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 129

Val Tyr Gly Gly Leu Phe Gly Asp Asn Glu Gly Val Lys Lys Ile Asp
1               5                   10                  15

Val

<210> SEQ ID NO 130
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Val Tyr Glu Leu Ser Ser Gly Asp Ile Glu Gly Val Lys Lys Ile Asp
1               5                   10                  15

Val

<210> SEQ ID NO 131
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Val Tyr Gly Leu Ser Phe Arg Asp Ile Gly Gly Val Lys Lys Ile Asp
1               5                   10                  15

Val

<210> SEQ ID NO 132
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Val Tyr Gly Leu Ser Leu Gly Asp Ile Glu Gly Val Lys Lys Ile Asp
1               5                   10                  15

Val

<210> SEQ ID NO 133
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Val Tyr Asp Glu Ser Phe Arg Asp Ile Glu Gly Val Lys Lys Ile Asp
1               5                   10                  15

Val

<210> SEQ ID NO 134
<211> LENGTH: 17
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

Val Tyr Gly Leu Ser Phe Arg Asp Ile Glu Gly Val Lys Lys Ile Asp
1               5                   10                  15
Val

<210> SEQ ID NO 135
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Val Tyr Gly Arg Ser Phe Gly Asp Ile Glu Lys Val Lys Lys Ile Asp
1               5                   10                  15
Val

<210> SEQ ID NO 136
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Val Phe Gly Trp Ser Phe Leu Asp Ile Glu Gly Val Lys Lys Ile Asp
1               5                   10                  15
Val

<210> SEQ ID NO 137
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Val Tyr Gly Leu Asp Phe Gly Asp Met Glu Gly Val Lys Lys Ile Asp
1               5                   10                  15
Val

<210> SEQ ID NO 138
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Val Tyr Gly Leu Ser Phe Gly Asp Lys Glu Lys Val Lys Lys Ile Asp
1               5                   10                  15
```

Val

<210> SEQ ID NO 139
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Val Tyr Gly Leu Ser Glu Gly Asp Tyr Glu Gly Val Lys Lys Ile Asp
1               5                   10                  15
Val

<210> SEQ ID NO 140
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Val Tyr Gly Met Ser Phe Gly Asp Val Glu Gly Val Lys Lys Ile Asp
1               5                   10                  15
Val

<210> SEQ ID NO 141
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Val Tyr Gly Leu Ser Phe Gly Ser Asn Glu Gly Val Lys Lys Ile Asp
1               5                   10                  15
Val

<210> SEQ ID NO 142
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Val Tyr Gly Val Ser Phe Gly Asp Ile Glu Gly Val Lys Lys Ile Asp
1               5                   10                  15
Val

<210> SEQ ID NO 143
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 143

Val Ile Gly Leu Ser Phe Gly Asp Leu Trp Gly Val Lys Lys Ile Asp
1               5                   10                  15
Val

<210> SEQ ID NO 144
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Val Tyr Gly Leu Phe Phe Gly Asp Ile Glu Gly Val Lys Lys Ile Asp
1               5                   10                  15
Val

<210> SEQ ID NO 145
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Val Tyr Gly Leu Ser Phe Gly Asp Ile Glu Gly Gln Lys Lys Ile Asp
1               5                   10                  15
Val

<210> SEQ ID NO 146
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Val Tyr Gly Leu Ser His Gly Asp Ile Gly Gly Val Lys Lys Ile Asp
1               5                   10                  15
Val

<210> SEQ ID NO 147
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Val Asn Gly Leu Ser Phe Lys Asp Ile Glu Gly Val Lys Asp Ile Asp
1               5                   10                  15
Val

<210> SEQ ID NO 148
<211> LENGTH: 17
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 148

Val Tyr Met Tyr Met Phe Gly Asp Ile Glu Gly Leu Lys Lys Ile Asp
1               5                   10                  15
Val

<210> SEQ ID NO 149
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 149

Val Phe Gly Leu Ser Phe Gly Asp Ile Glu Gly Val Lys Lys Ile Asp
1               5                   10                  15
Val

<210> SEQ ID NO 150
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Val Phe Gly Trp Ser Phe Gly Asp Ile Glu Gly Val Lys Lys Ile Asp
1               5                   10                  15
Val

<210> SEQ ID NO 151
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Val Leu Gly Met Ser Phe Gly Glu Ile Glu Gly Val Lys Lys Ile Asp
1               5                   10                  15
Val

<210> SEQ ID NO 152
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Val Asn Gly Trp Ser His Gly Asp Ile Glu Gly Val Lys Lys Ile Asp
1               5                   10                  15
```

Val

<210> SEQ ID NO 153
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Val Tyr Gly Leu Ser Phe Gly Asp Ile Met Gly Val Lys Lys Ile Asp
1               5                   10                  15

Val

<210> SEQ ID NO 154
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Val Tyr Gly Leu Ser Phe Lys Asp Ile Trp Gly Val Lys Lys Ile Asp
1               5                   10                  15

Val

<210> SEQ ID NO 155
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Val Tyr Glu Leu Ser Phe Gly Asp Ile Glu Gly Val Lys Tyr Ile Asp
1               5                   10                  15

Val

<210> SEQ ID NO 156
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Val Trp Gly Leu Ser Phe Gly Asp Phe Glu Gly Val Lys Lys Ile Asp
1               5                   10                  15

Val

<210> SEQ ID NO 157
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 157

Val Tyr Gly Trp Ser Phe Gly Asp Ile Leu Gly Val Lys Lys Ile Asp
1               5                   10                  15

Val

<210> SEQ ID NO 158
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Val Tyr Gly Trp Phe Phe Gly Asp His Glu Gly Val Lys Lys Ile Asp
1               5                   10                  15

Val

<210> SEQ ID NO 159
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Val Tyr Gly Leu Ser Phe Gly Asp Ile Glu Glu Val Lys Lys Ile Asp
1               5                   10                  15

Val

<210> SEQ ID NO 160
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

Val Tyr Gly Met Phe Phe Lys Asp Ile Glu Gly Val Lys Lys Ile Asp
1               5                   10                  15

Val

<210> SEQ ID NO 161
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Val Thr Gly Met Ser Phe Gly Asp Asp Glu Gly Val Lys Lys Ile Asp
1               5                   10                  15

Val

<210> SEQ ID NO 162

```
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 162

Val Tyr Lys Trp Ser Phe Met Asp Ile Glu Gly Val Lys Lys Ile Asp
1               5                   10                  15

Val

<210> SEQ ID NO 163
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

Val Tyr Gly Trp Ser Phe Gly Asp Asn Trp Gly Val Lys Lys Ile Asp
1               5                   10                  15

Val

<210> SEQ ID NO 164
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

Val Tyr Lys Leu Ser Lys Gly Asp Ile Glu Gly Val Lys Lys Ile Asp
1               5                   10                  15

Val

<210> SEQ ID NO 165
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Val Trp Lys Leu Ser Phe Gly Asp Ile Glu Gly Val Lys Lys Ile Asp
1               5                   10                  15

Val

<210> SEQ ID NO 166
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Val Tyr Leu Leu Ser Phe Phe Asp Leu Glu Gly Val Lys Lys Ile Asp
```

Val

<210> SEQ ID NO 167
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Val Tyr Gly Leu Val Tyr Ile Asp Ile Glu Gly Val Lys Lys Ile Asp
1               5                   10                  15

Val

<210> SEQ ID NO 168
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Val Phe Gly Leu Ser Phe Trp Asp Ile Glu Gly Val Lys Lys Ile Asp
1               5                   10                  15

Val

<210> SEQ ID NO 169
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Val Tyr Gly Leu Ser Ser Gly Asp Ile Glu Gly Met Lys Lys Ile Asp
1               5                   10                  15

Val

<210> SEQ ID NO 170
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Val Phe Asn Leu Val Phe Gly Asp Ile Glu Gly Val Lys Lys Ile Asp
1               5                   10                  15

Val

<210> SEQ ID NO 171
<211> LENGTH: 17
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 171

Val Asp Gly Leu Ser Phe Gly Asp Ile Glu Gly Val Lys Lys Ile Asp
1               5                   10                  15
Val

<210> SEQ ID NO 172
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Val Tyr Leu Thr Ser Phe Gly Asp Ile Glu Gly Val Lys Lys Ile Asp
1               5                   10                  15
Val

<210> SEQ ID NO 173
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Val Tyr Met Phe Ser Phe Gly Asp Ile Gly Gly Val Lys Lys Ile Asp
1               5                   10                  15
Val

<210> SEQ ID NO 174
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Val Tyr Gly Leu Ser Leu Gly Asp Ile Gln Gly Val Lys Lys Ile Asp
1               5                   10                  15
Val

<210> SEQ ID NO 175
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Val Asn Gly Leu Ser Ser Gly Asp Ile Glu Gly Val Lys Lys Ile Asp
1               5                   10                  15
Val
```

```
<210> SEQ ID NO 176
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Val Asn Gly Leu Ser Phe Gly Asp Ile Glu Gly Val Gly Lys Ile Asp
1               5                   10                  15

Val

<210> SEQ ID NO 177
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Val Trp Gly Leu Ser Phe Gly Asp Ile Glu Gly Arg Lys Lys Ile Asp
1               5                   10                  15

Val

<210> SEQ ID NO 178
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Val Tyr Gly Leu Val Phe Gly Asp Ile Glu Gly Arg Lys Lys Ile Asp
1               5                   10                  15

Val

<210> SEQ ID NO 179
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

Val Tyr Gly Leu Ser Phe Gly Thr Ile Gly Gly Val Lys Lys Ile Asp
1               5                   10                  15

Val

<210> SEQ ID NO 180
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180
```

```
Val Tyr Gly Leu Ser Phe Ser Lys Ile Glu Gly Val Lys Lys Ile Asp
1               5                   10                  15

Val

<210> SEQ ID NO 181
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

Val Leu Gly Leu Lys Phe Gly Gln Ile Glu Gly Val Lys Met Ile Asp
1               5                   10                  15

Val

<210> SEQ ID NO 182
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Val Tyr Gly Leu Ser Phe Gly Asp Asn Glu Gly Val Lys Lys Ile Asp
1               5                   10                  15

Val

<210> SEQ ID NO 183
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Val Phe Asn Leu Ser Phe Gly Asp Ile Glu Gly Val Lys Lys Ile Asp
1               5                   10                  15

Val

<210> SEQ ID NO 184
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Val Val Gly Leu Ser Leu Gly Asp Ile Glu Gly Val Lys Lys Ile Asp
1               5                   10                  15

Val

<210> SEQ ID NO 185
<211> LENGTH: 17
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 185

Val Tyr Gly Leu Lys Phe Gly Asp Ile Glu Gly Val Lys Lys Ile Asp
1               5                   10                  15
Val

<210> SEQ ID NO 186
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 186

Val Tyr Gly Leu Leu Phe Gly Asp Ile Glu Gly Val Lys Lys Ile Asp
1               5                   10                  15
Val

<210> SEQ ID NO 187
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Val Tyr Gly Leu Ser Ile Gly Asp Ile Glu Gly Val Lys Lys Ile Asp
1               5                   10                  15
Val

<210> SEQ ID NO 188
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Val Tyr Gly Leu Ser Phe Leu Asp Ile Glu Gly Val Lys Lys Ile Asp
1               5                   10                  15
Val

<210> SEQ ID NO 189
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

Val Tyr Gly Leu Ser Phe Gly Asp Ile Lys Gly Val Lys Lys Ile Asp
1               5                   10                  15
Val
```

```
<210> SEQ ID NO 190
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190

Val Thr Gly Leu Ser Phe Gly Asp Ile Glu Gly Val Lys Lys Ile Asp
1               5                   10                  15

Val

<210> SEQ ID NO 191
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

Val Ser Gly Met Ser Phe Gly Asp Ile Glu Gly Val Lys Lys Ile Asp
1               5                   10                  15

Val

<210> SEQ ID NO 192
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Val Lys Gly Leu Ser Phe Gly Asp Ile Glu Gly Val Lys Lys Ile Asp
1               5                   10                  15

Val

<210> SEQ ID NO 193
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Val Trp Gly Leu Ser Phe Gly Asp Ile Glu Gly Val Lys Lys Ile Asp
1               5                   10                  15

Val

<210> SEQ ID NO 194
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194
```

-continued

Val Tyr Gly Leu Ser Phe Gly Asp Ile Glu Glu Val Lys Lys Ile Asp
1               5                   10                  15
Val

<210> SEQ ID NO 195
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Val Tyr Gly Leu Ser Thr Gly Asp Ile Glu Gly Val Lys Lys Ile Asp
1               5                   10                  15
Val

<210> SEQ ID NO 196
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 196

Val Tyr Gly Leu Ser Phe Gly Arg Ile Glu Gly Val Lys Lys Ile Asp
1               5                   10                  15
Val

<210> SEQ ID NO 197
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 197

Val Phe Gln Leu Ser Phe Gly Asp Ile Glu Gly Val Lys Lys Ile Asp
1               5                   10                  15
Val

<210> SEQ ID NO 198
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Val Met Gly Leu Ser Phe Gly Asp Ile Glu Gly Val Lys Lys Ile Asp
1               5                   10                  15
Val

<210> SEQ ID NO 199
<211> LENGTH: 17
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 199

Val Tyr Gly Met Ser Phe Gly Asp Leu Glu Gly Val Lys Lys Ile Asp
1               5                   10                  15

Val

<210> SEQ ID NO 200
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Val Tyr Gly Leu Ser Phe Gly Asp Asp Ser Gly Val Lys Lys Ile Asp
1               5                   10                  15

Val

<210> SEQ ID NO 201
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Val Tyr Gly Leu Ser Phe Gly Asp Ile Glu Gly Gly Lys Lys Ile Asp
1               5                   10                  15

Val

<210> SEQ ID NO 202
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Val Tyr Gly Leu Ser Phe Gly Met Ile Trp Gly Val Lys Lys Ile Asp
1               5                   10                  15

Val

<210> SEQ ID NO 203
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Val Tyr Gly Leu Ser Phe Glu Asp Phe Glu Gly Val Lys Lys Ile Asp
1               5                   10                  15

Val
```

<210> SEQ ID NO 204
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Val Tyr Gly Leu Ser Phe Gly Asp Ile Glu Gly Val Gly Lys Ile Asp
1               5                   10                  15

Val

<210> SEQ ID NO 205
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Val Tyr Gly Leu Ser Phe Ser Asp Ile Glu Gly Val Lys Lys Ile Asp
1               5                   10                  15

Val

<210> SEQ ID NO 206
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Val Leu Gly Leu Ser Phe Gly Asp Ile Glu Gly Arg Lys Lys Ile Asp
1               5                   10                  15

Val

<210> SEQ ID NO 207
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Val Asn Gly Leu Ser Phe Lys Asp Ile Glu Gly Val Lys Lys Ile Asp
1               5                   10                  15

Val

<210> SEQ ID NO 208
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

```
<400> SEQUENCE: 208

Val Tyr Gly Leu Ser Phe Gly Asp Leu Trp Gly Val Lys Lys Ile Asp
1               5                   10                  15

Val

<210> SEQ ID NO 209
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Val Tyr Gly Met Ser Phe Gly Asp Ser Trp Gly Val Lys Lys Ile Asp
1               5                   10                  15

Val

<210> SEQ ID NO 210
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210

Val Tyr Gly Leu Ser Gly Gly Asp Ile Glu Gly Val Lys Lys Ile Asp
1               5                   10                  15

Val

<210> SEQ ID NO 211
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 211

Val Tyr Gly Leu Ser Leu Gly Arg Ile Glu Gly Val Lys Lys Ile Asp
1               5                   10                  15

Val

<210> SEQ ID NO 212
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 212

Val Tyr Gln Trp Leu Phe Gly Asp Ile Glu Gly Val Lys Lys Ile Asp
1               5                   10                  15

Val

<210> SEQ ID NO 213
<211> LENGTH: 17
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Val Phe Gly Lys Ser Phe Gly Glu Ile Glu Gly Val Lys Lys Ile Asp
1               5                   10                  15
Val

<210> SEQ ID NO 214
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Val Phe Gly Leu Ser Phe Gly Leu Ile Glu Gly Val Lys Lys Ile Asp
1               5                   10                  15
Val

<210> SEQ ID NO 215
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Val Asn Gly Leu Ser Ile Gly Asp Ile Glu Gly Tyr Lys Lys Ile Asp
1               5                   10                  15
Val

<210> SEQ ID NO 216
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Val Thr Gly Leu Ser Phe Gly Asp Ile Asn Gly Val Lys Lys Ile Asp
1               5                   10                  15
Val

<210> SEQ ID NO 217
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Val Tyr Gly Gly Ser Phe Gly Asp Ile Met Gly Val Lys Lys Ile Asp
1               5                   10                  15
```

Val

<210> SEQ ID NO 218
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Val Tyr Gly Leu Ser Phe Gly Asp Ile Glu Phe Val Lys Lys Ile Asp
1               5                   10                  15

Val

<210> SEQ ID NO 219
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Val Tyr Gly Leu Ser Phe Gly Asp Ile Pro Gly Val Lys Lys Ile Asp
1               5                   10                  15

Val

<210> SEQ ID NO 220
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Val Tyr Gly Leu Ser Phe Gly Pro His Glu Gly Val Lys Lys Ile Asp
1               5                   10                  15

Val

<210> SEQ ID NO 221
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Val Tyr Gly Leu Ser Met Gly Asp Ile Leu Gly Val Lys Lys Ile Asp
1               5                   10                  15

Val

<210> SEQ ID NO 222
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 222

Val Tyr Gly Leu Val Phe Gly Asp Ile Glu Gly Val Lys Thr Ile Asp
1               5                   10                  15

Val

<210> SEQ ID NO 223
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Val Tyr Leu Leu Ser Phe Gly Phe Ile Glu Gly Val Lys Lys Ile Asp
1               5                   10                  15

Val

<210> SEQ ID NO 224
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Val Phe Gly Leu Ser Phe Gly Asp Ile Arg Gly Val Lys Lys Ile Asp
1               5                   10                  15

Val

<210> SEQ ID NO 225
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Val Phe Gly Leu Ser Phe Gly Asp Ile Trp Gly Val Lys Lys Ile Asp
1               5                   10                  15

Val

<210> SEQ ID NO 226
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

Val Ile Gly Trp Ser Phe Trp Asp Ile Glu Gly Val Lys Lys Ile Asp
1               5                   10                  15

Val

<210> SEQ ID NO 227
<211> LENGTH: 17
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227

Val Ile Gln Leu Ser Phe Gly Asp Ile Glu Gly Val Lys Lys Ile Asp
1               5                   10                  15
Val

<210> SEQ ID NO 228
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Val Leu Gly Gly Ser Phe Gly Asp Ile Glu Gly Val Lys Lys Ile Asp
1               5                   10                  15
Val

<210> SEQ ID NO 229
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Val Arg Gly Leu Ser Phe Gly Asp Ile Glu Gly Val Arg Lys Ile Asp
1               5                   10                  15
Val

<210> SEQ ID NO 230
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Val Tyr Gly Leu Ser Asp Gly Asp Ile Trp Gly Val Lys Lys Ile Asp
1               5                   10                  15
Val

<210> SEQ ID NO 231
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Val Tyr Gly Leu Ser Phe Glu Gly Ile Glu Gly Ala Lys Lys Ile Asp
1               5                   10                  15
```

Val

<210> SEQ ID NO 232
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Val Tyr Gly Leu Ser Phe Gly Asp Tyr Trp Gly Val Lys Lys Ile Asp
1               5                   10                  15

Val

<210> SEQ ID NO 233
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Val Tyr Gly Leu Ser Phe Gly Trp Ile Trp Gly Val Lys Lys Ile Asp
1               5                   10                  15

Val

<210> SEQ ID NO 234
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Val Tyr Gly Leu Ser Phe Leu Trp Ile Glu Gly Val Lys Lys Ile Asp
1               5                   10                  15

Val

<210> SEQ ID NO 235
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Val Tyr Gly Leu Ser Asn Gly Asp Ile Glu Gly Val Lys Asp Ile Asp
1               5                   10                  15

Val

<210> SEQ ID NO 236
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 236

Val Tyr Leu Leu Leu Trp Gly Asp Ile Glu Gly Val Lys Lys Ile Asp
1               5                   10                  15

Val

<210> SEQ ID NO 237
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

Val His Gly Leu Ser Phe Leu Asp Ile Glu Gly Val Lys Lys Ile Asp
1               5                   10                  15

Val

<210> SEQ ID NO 238
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Val Tyr Gly Leu Ser Ile Gly Asp Tyr Glu Gly Val Lys Lys Ile Asp
1               5                   10                  15

Val

<210> SEQ ID NO 239
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Val Leu Gly Leu Ser Phe Gly Ala Ile Glu Gly Val Lys Lys Ile Asp
1               5                   10                  15

Val

<210> SEQ ID NO 240
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Val Trp Phe Leu Ser Phe Gly Trp Ile Glu Gly Val Lys Lys Ile Asp
1               5                   10                  15

Val

<210> SEQ ID NO 241

<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 241

Val Tyr Gly Leu Glu Phe Gly Asp Ile Glu Gly Val Lys Lys Ile Asp
1               5                   10                  15

Val

<210> SEQ ID NO 242
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 242

Val Tyr Ser Leu Ser Val Gly Asp Ile Glu Gly Val Ile Lys Ile Asp
1               5                   10                  15

Val

<210> SEQ ID NO 243
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 243

Val Val Tyr Gly Ser Phe Gly Asp Ile Glu Gly Val Lys Lys Ile Asp
1               5                   10                  15

Val

<210> SEQ ID NO 244
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 244

Val Ile Gly Leu Ser Phe Gly Asp Ile Glu Gly Val Lys Lys Ile Asp
1               5                   10                  15

Val

<210> SEQ ID NO 245
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 245

Val Tyr Gly Phe Phe Glu Gly Asp Ile Glu Gly Val Lys Lys Ile Asp

```
1               5                   10                  15
Val

<210> SEQ ID NO 246
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 246

Val Tyr Gly Leu Leu Tyr Gly Asp Phe Glu Gly His Lys Lys Ile Asp
1               5                   10                  15

Val

<210> SEQ ID NO 247
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 247

Val Tyr Gly Leu Ser Phe Gly Phe Asn Glu Gly Val Lys Lys Ile Asp
1               5                   10                  15

Val

<210> SEQ ID NO 248
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 248

Val Tyr Gly Leu Ser Lys Gly Asp Ile Arg Gly Val Lys Lys Ile Asp
1               5                   10                  15

Val

<210> SEQ ID NO 249
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 249

Val Tyr Gly Leu Ser Ser Gly Asp Leu Glu Gly Val Lys Lys Ile Asp
1               5                   10                  15

Val

<210> SEQ ID NO 250
<211> LENGTH: 17
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 250

Val Tyr Gln Leu Ser Ile Gly Asp Ile Glu Gly Val Lys Lys Ile Asp
1               5                   10                  15

Val

<210> SEQ ID NO 251
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

Val Phe Gly Leu Ser Phe Gly Arg Ile Glu Gly Val Lys Lys Ile Asp
1               5                   10                  15

Val

<210> SEQ ID NO 252
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

Val Tyr Gly Leu Ser Phe Gly Glu Ile Glu Gly Val Lys Lys Ile Asp
1               5                   10                  15

Val

<210> SEQ ID NO 253
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

Val Tyr Gly Leu Ser Leu Leu Asp Ile Glu Gly Val Lys Lys Ile Asp
1               5                   10                  15

Val

<210> SEQ ID NO 254
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 254

Val Tyr Gly Leu Trp Leu Gly Asp Ile Glu Gly Val Lys Lys Ile Asp
1               5                   10                  15

Val
```

-continued

```
<210> SEQ ID NO 255
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 255

Val Tyr Gly Glu Ser Phe Gly Asp Ile Glu Gly Val Lys Lys Ile Asp
1               5                   10                  15

Val

<210> SEQ ID NO 256
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 256

Val Tyr Gly Leu Ser Phe Gly Asp Ile Arg Gly Val Lys Arg Ile Asp
1               5                   10                  15

Val

<210> SEQ ID NO 257
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 257

Val Tyr Gly Leu Trp Phe Gly Asp Ile Glu Gly Val Asn Lys Ile Asp
1               5                   10                  15

Val

<210> SEQ ID NO 258
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 258

Val Tyr Gly Met Ser Phe Gly Asp Ile Glu Gly Trp Lys Lys Ile Asp
1               5                   10                  15

Val

<210> SEQ ID NO 259
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 259
```

```
Val Tyr Gly Met Ser Phe Gly Phe Ile Glu Gly Val Lys Lys Ile Asp
1               5                   10                  15

Val

<210> SEQ ID NO 260
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 260

Val Phe Gly Leu Ser Phe Gly Asp Ile Glu Gln Val Lys Lys Ile Asp
1               5                   10                  15

Val

<210> SEQ ID NO 261
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 261

Val Phe Gly Trp Phe Phe Gly Asp Ile Glu Gly Val Lys Lys Ile Asp
1               5                   10                  15

Val

<210> SEQ ID NO 262
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

Val His Gly Leu Ser Phe Arg Asp Met Glu Gly Val Lys Lys Ile Asp
1               5                   10                  15

Val

<210> SEQ ID NO 263
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 263

Val Ile Gly Ile Leu Phe Gly Asp Ile Glu Gly Val Lys Lys Ile Asp
1               5                   10                  15

Val

<210> SEQ ID NO 264
<211> LENGTH: 17
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 264

Val Tyr Glu Leu Phe Phe Gly Asp Gln Glu Gly Val Lys Lys Ile Asp
1               5                   10                  15
Val

<210> SEQ ID NO 265
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 265

Val Tyr Phe Leu Ser Phe Gly Asp Ser Glu Gly Val Lys Lys Ile Asp
1               5                   10                  15
Val

<210> SEQ ID NO 266
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 266

Val Tyr Gly Phe Ser Phe Gly Asp Trp Glu Gly Val Lys Lys Ile Asp
1               5                   10                  15
Val

<210> SEQ ID NO 267
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 267

Val Tyr Gly Leu Lys Trp Gly Asp Ile Glu Gly Val Lys Lys Ile Asp
1               5                   10                  15
Val

<210> SEQ ID NO 268
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 268

Val Tyr Gly Leu Gln Leu Gly Asp Ile Glu Gly Val Lys Lys Ile Asp
1               5                   10                  15
Val
```

```
<210> SEQ ID NO 269
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 269

Val Tyr Gly Leu Ser Phe Glu Asp Ile Met Gly Val Lys Lys Ile Asp
1               5                   10                  15

Val

<210> SEQ ID NO 270
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 270

Val Tyr Gly Leu Ser Phe Gly Asp Ile Glu Phe Met Lys Lys Ile Asp
1               5                   10                  15

Val

<210> SEQ ID NO 271
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 271

Val Tyr Gly Leu Ser Phe Gly Asp Ile Asn Gly Val Lys Lys Ile Asp
1               5                   10                  15

Val

<210> SEQ ID NO 272
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 272

Val Tyr Gly Ser Ser Phe Gly Asp Ile Glu Gly Arg Lys Lys Ile Asp
1               5                   10                  15

Val

<210> SEQ ID NO 273
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 273
```

```
Val Lys Gly Leu Ser Phe Gly Asp Leu Glu Gly Val Lys Lys Ile Asp
1               5                   10                  15
Val
```

<210> SEQ ID NO 274
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 274

```
Val Asn Gly Leu Ser Gln Gly Asp Ile Glu Trp Val Lys Lys Ile Asp
1               5                   10                  15
Val
```

<210> SEQ ID NO 275
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 275

```
Val Asn Gly Leu Ser Thr Gly Asp Gln Glu Gly Val Lys Lys Ile Asp
1               5                   10                  15
Val
```

<210> SEQ ID NO 276
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 276

```
Val Thr Gly Leu Ser Lys Gly Asp Ile His Gly Val Lys Lys Ile Asp
1               5                   10                  15
Val
```

<210> SEQ ID NO 277
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 277

```
Val Tyr Gly Ile Ile Glu Gly Asp Ile Glu Gly Val Lys Lys Ile Asp
1               5                   10                  15
Val
```

<210> SEQ ID NO 278
<211> LENGTH: 17
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 278

Val Tyr Gly Leu Ser Ser Gly Ser Ile Pro Gly Val Lys Lys Ile Asp
1               5                   10                  15

Val

<210> SEQ ID NO 279
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 279

Val Tyr Gly Leu Ser Tyr Arg Asp Ile Glu Gly Val Lys Lys Ile Asp
1               5                   10                  15

Val

<210> SEQ ID NO 280
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 280

Val Tyr Gly Leu Thr Tyr Lys Asp Ile Glu Gly Val Lys Lys Ile Asp
1               5                   10                  15

Val

<210> SEQ ID NO 281
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 281

Val Tyr Lys Leu Leu Val Gly Asp Ile Glu Gly Val Lys Lys Ile Asp
1               5                   10                  15

Val

<210> SEQ ID NO 282
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Val Tyr Lys Trp Met Phe Gly Asp Ile Glu Gly Val Lys Trp Ile Asp
1               5                   10                  15

Val
```

```
<210> SEQ ID NO 283
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

Val Tyr Met Leu Phe Phe Gly Asp Arg Glu Gly Val Lys Lys Ile Asp
1               5                   10                  15

Val

<210> SEQ ID NO 284
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 284

Val Tyr Gln Leu Val Leu Gly Asp Ile Glu Gly Val Lys Lys Ile Asp
1               5                   10                  15

Val

<210> SEQ ID NO 285
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 285

Val Phe Gly Leu Ser Phe Gly Asp Ile Met Gly Val Lys His Ile Asp
1               5                   10                  15

Val

<210> SEQ ID NO 286
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 286

Val Phe Gly Leu Ser Phe Gly Ser Ile Glu Gly Val Lys Lys Ile Asp
1               5                   10                  15

Val

<210> SEQ ID NO 287
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

```
<400> SEQUENCE: 287

Val Lys Gln Leu Ser Leu Gly Asp Ile Glu Gly Val Lys Lys Ile Asp
1               5                   10                  15
Val

<210> SEQ ID NO 288
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 288

Val Tyr Gly Leu Ala Tyr Gly Phe Ile Glu Gly Val Lys Lys Ile Asp
1               5                   10                  15
Val

<210> SEQ ID NO 289
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 289

Val Tyr Gly Leu Lys Phe Gly Asp Ile Glu Arg Val Lys Lys Ile Asp
1               5                   10                  15
Val

<210> SEQ ID NO 290
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 290

Val Tyr Gly Leu Met Met Gly Asp Ile Glu Gly Val Lys Lys Ile Asp
1               5                   10                  15
Val

<210> SEQ ID NO 291
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 291

Val Tyr Gly Leu Ser Phe Gly Asp Phe Glu Gly Val Lys Gln Ile Asp
1               5                   10                  15
Val

<210> SEQ ID NO 292
<211> LENGTH: 17
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 292

Val Tyr Gly Leu Ser Phe Gly Asp His Phe Thr Val Lys Lys Ile Asp
1               5                  10                  15

Val

<210> SEQ ID NO 293
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 293

Val Tyr Gly Leu Ser Phe Gly Asp Ile Glu Leu Val Ala Lys Ile Asp
1               5                  10                  15

Val

<210> SEQ ID NO 294
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 294

Val Tyr Gly Leu Ser Val Met Asp Ile Glu Gly Val Lys Lys Ile Asp
1               5                  10                  15

Val

<210> SEQ ID NO 295
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 295

Val Tyr Gly Leu Val Phe Gly Asp Asp Glu Gly Val Lys Lys Ile Asp
1               5                  10                  15

Val

<210> SEQ ID NO 296
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 296

Val Tyr Gly Leu Val Ile Gly Asp Ile Gln Gly Val Lys Lys Ile Asp
1               5                  10                  15
```

```
<210> SEQ ID NO 297
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 297

Val Tyr Gly Met Ser Phe Gly Glu Ile Glu Gly Val Lys Lys Ile Asp
1               5                   10                  15
Val

<210> SEQ ID NO 298
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 298

Val Tyr Gly Met Ser Leu Gly Asp Ile Glu Gly Glu Lys Lys Ile Asp
1               5                   10                  15
Val

<210> SEQ ID NO 299
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

Val Tyr Gln Leu Ser Leu Gly Asp Ile Glu Gly Val Lys Lys Ile Asp
1               5                   10                  15
Val

<210> SEQ ID NO 300
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Val Phe Gly Leu Ser Phe Met Asp Leu Glu Gly Val Lys Lys Ile Asp
1               5                   10                  15
Val

<210> SEQ ID NO 301
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

```
<400> SEQUENCE: 301

Val Phe Ser Leu Ser Tyr Trp Asp Ile Glu Gly Val Lys Lys Ile Asp
1               5                   10                  15

Val

<210> SEQ ID NO 302
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 302

Val Lys Gln Pro Ser Phe Gly Asp Ile Glu Gly Val Lys Lys Ile Asp
1               5                   10                  15

Val

<210> SEQ ID NO 303
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

Val Gln Gly Leu Ser Asp Gly Asp Ile Glu Gly Val Lys Lys Ile Asp
1               5                   10                  15

Val

<210> SEQ ID NO 304
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 304

Val Ser Gly Met Leu Phe Gly Asp Ile Asn Gly Val Lys Gly Ile Asp
1               5                   10                  15

Val

<210> SEQ ID NO 305
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 305

Val Tyr Gly Lys Ser Phe Gly Asp Met Trp Gly Val Lys Lys Ile Asp
1               5                   10                  15

Val

<210> SEQ ID NO 306
<211> LENGTH: 17
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 306

Val Tyr Gly Leu Gly Phe Gly Asp Ile Glu Gly Tyr Lys Lys Ile Asp
1               5                   10                  15
Val

<210> SEQ ID NO 307
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 307

Val Tyr Gly Leu Leu Asn Gly Asp Ile Glu Gly Asn Lys Lys Ile Asp
1               5                   10                  15
Val

<210> SEQ ID NO 308
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 308

Val Tyr Gly Leu Ser Phe Gly Asp His Asn Gly Trp Lys Lys Ile Asp
1               5                   10                  15
Val

<210> SEQ ID NO 309
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 309

Val Tyr Gly Leu Ser Phe Gly Asp Tyr Arg Gly Val Lys Lys Ile Asp
1               5                   10                  15
Val

<210> SEQ ID NO 310
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 310

Val Tyr Gly Leu Ser Phe Gly Phe Thr Glu Gly Val Lys Lys Ile Asp
1               5                   10                  15
```

Val

<210> SEQ ID NO 311
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Val Tyr Gly Leu Ser Phe Gly Trp Ile Arg Gly Val Lys Lys Ile Asp
1               5                   10                  15

Val

<210> SEQ ID NO 312
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312

Val Tyr Gly Leu Ser Phe Gly Trp Tyr Ala Gly Val Lys Lys Ile Asp
1               5                   10                  15

Val

<210> SEQ ID NO 313
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 313

Val Tyr Gly Leu Ser Phe Trp Asp Ile Gly Gly Val Lys Lys Ile Asp
1               5                   10                  15

Val

<210> SEQ ID NO 314
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 314

Val Tyr Gly Leu Ser Ile Leu Asp Ile Glu Gly Val Lys Lys Ile Asp
1               5                   10                  15

Val

<210> SEQ ID NO 315
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 315

Val Tyr Gly Leu Ser Leu Met Asp Leu Glu Gly Val Lys Lys Ile Asp
1               5                   10                  15

Val

<210> SEQ ID NO 316
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 316

Val Tyr Gly Leu Ser Met Gly Asp Ile Glu Gly Val Lys Asp Ile Asp
1               5                   10                  15

Val

<210> SEQ ID NO 317
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 317

Val Tyr Gly Leu Ser Trp Gly Asp Ile Glu Gly Gly Lys Lys Ile Asp
1               5                   10                  15

Val

<210> SEQ ID NO 318
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 318

Val Tyr Gly Val Phe Phe Lys Asp Ile Glu Gly Val Lys Lys Ile Asp
1               5                   10                  15

Val

<210> SEQ ID NO 319
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 319

Val Tyr Val Leu Ser Phe Met Asp Ile Glu Gly Val Lys Lys Ile Asp
1               5                   10                  15

Val

<210> SEQ ID NO 320

```
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 320

Val Phe Gly Leu Ser Phe Gly Asp Ile Glu Lys Val Lys Lys Ile Asp
1               5                   10                  15

Val

<210> SEQ ID NO 321
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 321

Val Thr Gly Leu Ser Phe Gly Asp Ile Glu Gly Val Asn Lys Ile Asp
1               5                   10                  15

Val

<210> SEQ ID NO 322
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 322

Val Tyr Gly Ile Ser Phe Gly Trp Ile Glu Gly Val Lys Lys Ile Asp
1               5                   10                  15

Val

<210> SEQ ID NO 323
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 323

Val Tyr Gly Leu Glu Phe Gly Asp Ile Asp Gly Val Lys Lys Ile Asp
1               5                   10                  15

Val

<210> SEQ ID NO 324
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 324

Val Tyr Gly Leu Ser Glu Gly Asp Ile Lys Gly Val Lys Lys Ile Asp
```

```
1               5                   10                  15
Val

<210> SEQ ID NO 325
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 325

Val Tyr Gly Leu Ser Phe Gly Asp Ile Glu Gly Val Lys Gly Ile Asp
1               5                   10                  15

Val

<210> SEQ ID NO 326
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 326

Val Tyr Gly Leu Ser Phe Gly Leu Ile Met Gly Val Lys Lys Ile Asp
1               5                   10                  15

Val

<210> SEQ ID NO 327
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 327

Val Tyr Gly Leu Ser Phe Gly Val Ile Glu Gly Val Lys Thr Ile Asp
1               5                   10                  15

Val

<210> SEQ ID NO 328
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 328

Val Tyr Gly Leu Ser Phe Ile Asp Ile Tyr Gly Val Lys Lys Ile Asp
1               5                   10                  15

Val

<210> SEQ ID NO 329
<211> LENGTH: 17
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 329

Val Tyr Gly Leu Ser Leu Gly Asp Ile Glu Gly Val Val Lys Ile Asp
1               5                   10                  15

Val

<210> SEQ ID NO 330
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 330

Val Tyr Gly Leu Ser Leu Gly Asp Tyr Glu Gly Ile Lys Lys Ile Asp
1               5                   10                  15

Val

<210> SEQ ID NO 331
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 331

Val Tyr Gly Leu Ser Leu Gly Gln Ile Glu Gly Val Lys Lys Ile Asp
1               5                   10                  15

Val

<210> SEQ ID NO 332
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 332

Val Tyr Gly Leu Ser Pro Leu Asp Ile Glu Gly Val Lys Lys Ile Asp
1               5                   10                  15

Val

<210> SEQ ID NO 333
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 333

Val Tyr Gly Leu Thr Ala Gly Leu Ile Glu Gly Val Lys Lys Ile Asp
1               5                   10                  15

Val

<210> SEQ ID NO 334
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 334

Val Tyr Gly Leu Tyr Phe Gly Gln Ile Glu Lys Val Lys Lys Ile Asp
1               5                   10                  15

Val

<210> SEQ ID NO 335
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 335

Val Tyr Leu Leu Phe Phe Gly Asp Ser Glu Gly Val Lys Lys Ile Asp
1               5                   10                  15

Val

<210> SEQ ID NO 336
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 336

Val Tyr Asn Leu Phe Phe Gly Asp Phe Glu Gly Val Lys Lys Ile Asp
1               5                   10                  15

Val

<210> SEQ ID NO 337
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 337

Val Tyr Gln Leu Ser Phe Gly Asp Phe Glu Gly Val Lys Lys Ile Asp
1               5                   10                  15

Val

<210> SEQ ID NO 338
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 338

-continued

Val Phe Lys Leu Ser Phe Gly Asp Ile Glu Gly Val Lys Lys Ile Asp
1               5                   10                  15

Val

<210> SEQ ID NO 339
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 339

Val Leu Phe Leu Ser Phe Gly Asp Ile Glu Gly Val Lys Lys Ile Asp
1               5                   10                  15

Val

<210> SEQ ID NO 340
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 340

Val Ser Gly Leu Ser Phe Gly Asp Ile Pro Gly Val Lys Lys Ile Asp
1               5                   10                  15

Val

<210> SEQ ID NO 341
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 341

Val Tyr Phe Leu Ser Phe Gly Asp Ile Ala Gly Val Lys Lys Ile Asp
1               5                   10                  15

Val

<210> SEQ ID NO 342
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 342

Val Tyr Phe Leu Ser Phe Leu Asp Ile Glu Gly Val Lys Lys Ile Asp
1               5                   10                  15

Val

<210> SEQ ID NO 343
<211> LENGTH: 17
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic peptide"

<400> SEQUENCE: 343

Val Tyr Gly Phe Ser Met Gly Asp Ile Glu Gly Val Lys Lys Ile Asp
1               5                   10                  15
Val

<210> SEQ ID NO 344
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 344

Val Tyr Gly Leu Ser Phe Gly Trp Asp Glu Gly Val Lys Lys Ile Asp
1               5                   10                  15
Val

<210> SEQ ID NO 345
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 345

Val Tyr Gly Leu Thr Phe Gly Leu Ile Met Gly Val Lys Lys Ile Asp
1               5                   10                  15
Val

<210> SEQ ID NO 346
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 346

Val Tyr Gly Arg Ser Phe Gly Asp Ile Glu His Val Lys Lys Ile Asp
1               5                   10                  15
Val

<210> SEQ ID NO 347
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 347

Val Tyr Gln Leu Ser Leu Gly Thr Ile Glu Gly Val Lys Lys Ile Asp
1               5                   10                  15
Val

<210> SEQ ID NO 348
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 348

Val Tyr Gln Leu Ser Met Gly Asp Ile Glu Gly Leu Lys Lys Ile Asp
1               5                   10                  15
Val

<210> SEQ ID NO 349
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 349

Val Asp Gly Leu Ser Phe Trp Asp Trp Glu Gly Val Lys Lys Ile Asp
1               5                   10                  15
Val

<210> SEQ ID NO 350
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 350

Val Glu Gly Leu Ser Phe Gly Asp Ile Trp Gly Val Lys Lys Ile Asp
1               5                   10                  15
Val

<210> SEQ ID NO 351
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 351

Val Ile Gly Arg Ser Phe Gly Asp Ile Glu Gly Val Lys Lys Ile Asp
1               5                   10                  15
Val

<210> SEQ ID NO 352
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 352

```
Val Gln Trp Leu Ser Phe Gly Asp Ile Glu Gly Val Lys Glu Ile Asp
1               5                   10                  15

Val

<210> SEQ ID NO 353
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 353

Val Tyr Gly Leu Pro Phe Gly Phe Thr Glu Gly Val Lys Lys Ile Asp
1               5                   10                  15

Val

<210> SEQ ID NO 354
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 354

Val Tyr Gly Leu Ser Phe Gly Ser Phe Phe Gly Val Lys Lys Ile Asp
1               5                   10                  15

Val

<210> SEQ ID NO 355
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 355

Val Tyr Gly Leu Thr Phe Gly Met Ile Met Gly Val Lys Lys Ile Asp
1               5                   10                  15

Val

<210> SEQ ID NO 356
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 356

Val Tyr Gly Arg Ser Phe Gly Asp Lys Gly Val Lys Lys Ile Asp
1               5                   10                  15

Val

<210> SEQ ID NO 357
<211> LENGTH: 17
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 357

Val Tyr Gly Val Ser Phe Gly Asp Ile Glu Gly Met Lys Lys Ile Asp
1               5                   10                  15

Val

<210> SEQ ID NO 358
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 358

Val Tyr Gly Trp Ser Tyr Gly Asp Ile Glu Gly Val Lys Lys Ile Asp
1               5                   10                  15

Val

<210> SEQ ID NO 359
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 359

Val Tyr Lys Leu Ser Tyr Leu Asp Ile Glu Gly Val Lys Lys Ile Asp
1               5                   10                  15

Val

<210> SEQ ID NO 360
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 360

Val Tyr Leu Gln Ser Phe Gly Asp Ile Glu Gly Val Met Lys Ile Asp
1               5                   10                  15

Val

<210> SEQ ID NO 361
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 361

Val Tyr Gly Phe Ser Phe Gly Ser Ile Glu Gly Val Lys Lys Ile Asp
1               5                   10                  15

Val
```

```
<210> SEQ ID NO 362
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 362

Thr Arg Glu Glu Thr Ile Ser
1               5

<210> SEQ ID NO 363
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 363

Ser Arg Glu Glu Thr Ile Ser
1               5

<210> SEQ ID NO 364
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (26)..(29)
<223> OTHER INFORMATION: Any amino acid except Cys
<220> FEATURE:
<221> NAME/KEY: MOD_RES
<222> LOCATION: (87)..(99)
<223> OTHER INFORMATION: Any amino acid except Cys

<400> SEQUENCE: 364

Ala Arg Val Asp Gln Thr Pro Gln Thr Ile Thr Lys Glu Glu Gly Glu
1               5                   10                  15

Ser Leu Thr Ile Asn Cys Val Leu Arg Xaa Xaa Xaa Xaa Ala Leu Ala
            20                  25                  30

Ser Thr Ser Trp Tyr Arg Lys Lys Ser Gly Ser Thr Arg Glu Glu Thr
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Xaa Xaa Xaa Xaa Xaa Xaa Xaa Xaa Xaa Xaa
                85                  90                  95

Xaa Xaa Xaa Asp Val Tyr Gly Asp Gly Thr Ala Val Thr Val Asn Ala
            100                 105                 110

<210> SEQ ID NO 365
<211> LENGTH: 14
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid except Cys

<400> SEQUENCE: 365

Tyr Xaa Leu Ser Phe Gly Asp Ile Glu Gly Val Lys Lys Ile
1               5                   10

<210> SEQ ID NO 366
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: Any amino acid except Cys

<400> SEQUENCE: 366

Tyr Gly Leu Ser Phe Gly Asp Xaa Glu Gly Val Lys Lys Ile
1               5                   10

<210> SEQ ID NO 367
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Any amino acid except Cys

<400> SEQUENCE: 367

Tyr Gly Leu Ser Phe Xaa Asp Ile Glu Gly Val Lys Lys Ile
1               5                   10

<210> SEQ ID NO 368
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(8)
<223> OTHER INFORMATION: Any amino acid except Cys

<400> SEQUENCE: 368

Tyr Gly Leu Ser Phe Gly Xaa Xaa Glu Gly Val Lys Lys Ile
1               5                   10

<210> SEQ ID NO 369
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

<221> NAME/KEY: MOD_RES
<222> LOCATION: (1)..(1)
<223> OTHER INFORMATION: Any amino acid except Cys
<220> FEATURE:
<221> NAME/KEY: MOD_RES
<222> LOCATION: (3)..(3)
<223> OTHER INFORMATION: Any amino acid except Cys

<400> SEQUENCE: 369

Xaa Gly Xaa Ser Phe Gly Asp Ile Glu Gly Val Lys Lys Ile
1               5                   10

<210> SEQ ID NO 370
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid except Cys
<220> FEATURE:
<221> NAME/KEY: MOD_RES
<222> LOCATION: (12)..(12)
<223> OTHER INFORMATION: Any amino acid except Cys

<400> SEQUENCE: 370

Tyr Xaa Leu Ser Phe Gly Asp Ile Glu Gly Val Xaa Lys Ile
1               5                   10

<210> SEQ ID NO 371
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid except Cys
<220> FEATURE:
<221> NAME/KEY: MOD_RES
<222> LOCATION: (8)..(8)
<223> OTHER INFORMATION: Any amino acid except Cys
<220> FEATURE:
<221> NAME/KEY: MOD_RES
<222> LOCATION: (13)..(13)
<223> OTHER INFORMATION: Any amino acid except Cys

<400> SEQUENCE: 371

Tyr Gly Xaa Ser Phe Gly Asp Xaa Glu Gly Val Lys Xaa Ile
1               5                   10

<210> SEQ ID NO 372
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(7)
<223> OTHER INFORMATION: Any amino acid except Cys

<400> SEQUENCE: 372

-continued

Tyr Gly Leu Ser Xaa Xaa Xaa Ile Glu Gly Val Lys Lys Ile
1               5                   10

<210> SEQ ID NO 373
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(3)
<223> OTHER INFORMATION: Any amino acid except Cys
<220> FEATURE:
<221> NAME/KEY: MOD_RES
<222> LOCATION: (14)..(14)
<223> OTHER INFORMATION: Any amino acid except Cys

<400> SEQUENCE: 373

Tyr Xaa Xaa Ser Phe Gly Asp Ile Glu Gly Val Lys Lys Xaa
1               5                   10

<210> SEQ ID NO 374
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 374

Val His Gly Arg Ala Leu Ala Ser
1               5

<210> SEQ ID NO 375
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(4)
<223> OTHER INFORMATION: Any amino acid except Cys

<400> SEQUENCE: 375

Xaa Xaa Xaa Xaa Ala Leu Ala
1               5

<210> SEQ ID NO 376
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(23)
<223> OTHER INFORMATION: Any amino acid except Cys
<220> FEATURE:
<221> NAME/KEY: SITE
<222> LOCATION: (3)..(23)
<223> OTHER INFORMATION: /note="This region may encompass 3-21 residues"

<400> SEQUENCE: 376

```
Val Tyr Xaa Xaa Xaa Xaa Xaa Xaa Xaa Xaa Xaa Xaa Xaa Xaa Xaa
1               5                   10                  15

Xaa Xaa Xaa Xaa Xaa Xaa Asp Val
            20              25
```

ANTI-CD98hc VNARs FOR CROSSING THE BLOOD BRAIN BARRIER AND TYPE IV VNAR LIBRARIES

CROSS REFERENCE TO RELATED APPLICATION

This PCT application claims the benefit of provisional application U.S. Ser. No. 62/688,966, filed on Jun. 22, 2018, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 19, 2019, is named OSX1802-WO1_SL.txt and is 135,468 bytes in size.

FIELD OF THE INVENTION

The present invention relates to CD98hc binding moieties with high specificity and with ability to cross the blood brain barrier (BBB). Such moieties may be used alone or as components in specific conjugates that target the amino acid transporter complexes formed with a light chain and CD98hc. The invention relates more specifically to VNAR domains, based on the nurse shark scaffold, that bind to CD98hc, compounds and compositions comprising a CD98hc-specific binding moiety, diagnostic and therapeutic methods of use in vitro or in vivo, e.g., to diagnose, treat and/or prevent a pathological condition, disorder or disease in which it is beneficial to deliver a heterologous biomolecule across the blood brain barrier by association with a CD98hc-specific VNAR binding moiety. The invention also includes Type IV semi-synthetic VNAR libraries derived from shark VNARs for selection of binding moieties that specifically bind to a molecular or cellular target of interest.

BACKGROUND OF THE INVENTION

One of the most significant challenges in pharmaceutical drug development is the targeting of drugs to the central nervous system (CNS). Despite recent advances, effective drug therapies against many CNS disorders such as Alzheimer's disease, Parkinson's disease, and brain tumors have yet to be developed. Successful treatment of the CNS disease requires not only the development of drugs to specific targets within the CNS, but also strategies to improve the passage of therapeutics across the relatively impermeable blood-brain barrier (BBB) to achieve efficacious levels in the CNS. It is estimated that not more than 2% of the small molecular weight drugs and practically none of the large molecular weight drugs developed for the CNS disorders cross the BBB at adequate levels (1).

The BBB expresses a number of specific carrier-mediated transporters, ensuring an adequate nutrient supply for the brain (2). These BBB transporters carry nutrients, such as amino acids, glucose, and vitamins, which cannot pass the BBB by passive diffusion due to their unfavorable physicochemical properties. Of the various solute transporter systems at the BBB, the large neutral amino acid transporter (LAT1/CD98) is highly expressed in brain capillaries that form the BBB and acts as an amino acid exchanger for the high-affinity transport of large neutral amino acids such as phenylalanine, tyrosine, leucine, arginine and tryptophan into the brain (3,4). The LAT1/CD98 complex appears to have one of the highest transport capacities (5) and may hold promise for delivering drugs to the brain.

LAT1/CD98 is a heterodimeric complex composed of two proteins: a light chain, LAT1 (also known as 4F2LC, CD981c, MPE16, hLAT1) encoded by the SLC7A5 gene and a heavy chain, CD98hc (also known as 4F2, 4F2HC, CD98, FRP-1) encoded by the SLC3A2 gene (6). The light chain functions as the catalytic subunit of the complex and is linked to the heavy chain by a disulfide bridge. CD98hc acts as a stabilizing chaperone to facilitate LAT1 translocation to the plasma membrane. Besides its role in amino acid transport, CD98hc acts as a co-receptor for integrin signaling, which mediates cell survival, proliferation and migration of T-lymphocytes required during clonal expansion in adaptive immunity (7, 8). LAT1/CD98 expression also is highly upregulated in many human cancers and it contributes to formation of tumors in experimental models (9).

In addition to its other endogenous functions, LAT1/CD98 also plays a role in drug transport to the brain. A number of small molecule drugs were found to cross the BBB via LAT1/CD98 transporter including L-DOPA, gabapentin, paraquat, and melphalan thus enabling their pharmacologic activity in the CNS (5). This semi-selective transport activity at the BBB has been further exploited by conjugating a small-molecule drug to a LAT1 substrate to significantly enhance BBB penetration (10,11). Using a different approach, a large molecule has been carried across the BBB by targeting the extracellular domain of the CD98hc with monoclonal antibodies (12). However, the doses required to achieve pharmacologic concentrations in the brain (50 mg/kg) are considerably higher than desirable for therapeutic use (13).

The same issue was encountered with using monoclonal antibodies to target transferrin receptors in the BBB for drug delivery. Monoclonal antibodies that bind the transporter with high affinity and avidity appear unable to dissociate from the receptor or are targeted to the lysosomes for degradation and thus fail to cross the BBB (14,15). By reducing the affinity (through mutation of the binding site) and the avidity (using a monovalent format), significant brain uptake could be achieved. However, lowering affinity/avidity antibodies also reduces antibody binding potency and will require considerably higher doses to achieve efficacy in vivo.

The variable domain of the immunoglobulin new antigen receptor (IgNAR), a homodimeric heavy chain-only antibody from cartilaginous fish (16), which binds antigens in unique ways, has been used to develop BBB-crossing shuttles (WO2015/200883; WO2018/031424; and U.S. Ser. Nos. 62/580,453, 62/580,934, and 62/624,107.)

With a molecular mass of ~12 kDa, the IgNAR variable domain (VNAR) is the smallest known antibody-like antigen binding domain (17). While most mammalian V domains have three CDR loops, VNARs have only CDRs 1 and 3 plus two additional regions that undergo a high rate of somatic mutation called HV2 and HV4 (18). Co-crystallization of a VNAR-antigen complex showed that all of 4 of these hypervariable regions can participate in binding (19). Additionally, non-canonical cysteine residues, which are not found in classical Ig variable domains, create disulfides bridges that stabilize and spatially orient the CDR3 loops (20). Based on the number of these non-canonical cysteine residues, VNAR molecules have been categorized into 4 different isotypes (21). These isotypes lead to a hugely expanded repertoire of available paratopes capable of binding with high affinities to chemical spaces on the surface of antigens that are inaccessible to classical antibodies.

With the need to produce more effective CNS therapeutics that can deliver molecules across the BBB at therapeutically-acceptable doses, VNARs directed against BBB transporters provide another source of BBB-crossing shuttles, particularly the LAT1/CD98hc transporter which takes advantage of its high abundance in brain capillaries. To capture the higher degree of structural diversity of the VNAR, a series of isotype specific phage display libraries was screened against BBB transporters (WO2015/200883). For this invention, such libraries were screened against the ectodomain of CD98hc and identified species cross-reactive epitopes in CD98hc that bind with high affinity and which can be fused to larger molecules in monovalent and bivalent formats to transport them into the brain at relevant therapeutic doses (<4 mg/kg of a bispecific VNAR-IgG fusion).

SUMMARY OF THE INVENTION

The present invention addresses the needs described above by providing specific binding moieties which bind selectively to a mammalian carrier transporter and particularly to CD98hc, and preferably to the ectodomain of CD98hc. Semi-synthetic VNAR phage libraries (separate type I, type II, and type IV isotypes) were used to select clones that bind to CD98hc. As provided herein, the CD98hc specific binding moieties of the invention comprise a VNAR domain capable of specifically binding to human CD98hc and murine CD98hc, wherein said VNAR domain is represented by the formula, from N to C terminus,

FW1-CDR1-FW2-HV2-FW2'-HV4-FW3-CDR3-FW4, and wherein CDR3 comprises an amino acid sequence as shown in Table 1A (the underlined portion) or as set out in Table 1B. In some embodiments, the VNAR domain comprises or consists essentially of an amino acid sequence as shown for the clones in Table 1A. In some embodiments, the VNAR domains comprise or consist essentially of amino acid sequences in Table 1B and Tables 5-9 for CDR1, HV2, HV4, CDR3, or any combinations thereof, that form a VNAR capable of binding to human CD98hc, and preferably both human and mouse CD98hc. The embodiments of the invention also include any CD98hc VNAR binding moiety of the invention disclosed in any of the tables herein (i.e., in Tables 1A, 1B and 5-9).

Additionally, in some embodiments, the isolated CD98hc-specific binding moiety comprises a Type IV VNAR domain capable of specifically binding to human CD98hc and murine CD98hc, wherein said VNAR domain is represented by the formula, from N to C terminus,

FW1-CDR1-FW2-HV2-FW2'-HV4-FW3-CDR3-FW4, wherein CDR1 comprises an amino acid sequence as shown in Table 1B, HV2 comprises an amino acid sequence of TREETISKG (SEQ ID NO. 1) or SREETISKG (SEQ ID NO. 2), HV4 comprises an amino acid sequence of NSGSKS (SEQ ID NO. 3) and wherein the CDR3 region comprises an amino acid sequence of formula $$V-Y-X_1-X_2-X_3-X_4-X_5-X_6-X_7-X_8-X_9-X_{10}-X_{11}-X_{12}-X_{13}-D-V, \quad \text{(SEQ ID NO. 4)}$$

wherein
$X_1$ is A, E, F, G or I,
$X_2$ is E, F, I, L, R or Y,
$X_3$ is H, L, P, R, S, V or Y,
$X_4$ is A, E, F, I, S or Y
$X_5$ is F, G, I, P, S or V,
$X_6$ is A, D, E, L, Q, S or T,
$X_7$ is C, E, F, I, K, P or V,
$X_8$ is D, E, K, N or T
$X_9$ is A, G, I, K, Q or V
$X_{10}$ is A, K, L, R, V or Y
$X_{11}$ is E, G, H, K, P, Q or Y
$X_{12}$ is D, E, F, G, K, P, S, T or Y, and
$X_{13}$ is F, H, I, N, Q or R.

The CDR1, CDR3, HV2 and HV4 regions can be combined in any manner provided that the VNAR domain retains its CD98hc specificity for human and murine CD98hc. In some embodiments, the CD98hc-binding moiety has an EC50 for human CD98hc ranging from about 0.1 nM to about 10 UM and preferably ranging from about 1 nM to about 800 nM. In other embodiments, the CD98hc-binding moiety is capable of crossing the blood brain barrier and when formatted as an Fc fusion protein and injected into mice at 1.875 mg/kg, the CD98hc-binding moiety can reach a concentration in murine brain homogenates of at least about 0.8 nM. Such concentration ranges may further span from about 0.8 nM to about 15 nM, from about 1 nM to about 12 nM, or from about 2.5 nM to about 10 nM.

In another embodiment, the isolated CD98hc-specific binding moiety is clone F12 or a variant of clone F12 and comprises a Type IV VNAR domain capable of specifically binding to human CD98hc and murine CD98hc, wherein said VNAR domain is represented by the formula, from N to C terminus,

FW1-CDR1-FW2-HV2-FW2'-HV4-FW3-CDR3-FW4, wherein CDR1 has an amino acid sequence of VHGRALAS (SEQ ID NO. 374), HV2 comprises an amino acid sequence of TREETISKG (SEQ ID NO. 1), HV4 comprises an amino acid sequence of NSGSKS (SEQ ID NO. 3), and CDR3 comprises an amino acid sequence of formula $$V-X_1-G-X_2-X_3-X_4-X_5-X_6-X_7-X_8-X_9-X_{10}-X_{11}-X_{12}-X_{13}-D-V, \quad \text{(SEQ ID NO. 5)}$$

wherein
$X_1$ is Y, D, F, H, K, N, S or W,
$X_2$ is L or V,
$X_3$ is S, G, E, K, L, M, Q or R,
$X_4$ is F, A, G, H, I, K, L, M, N, Q, R, S, T, W or Y,
$X_5$ is G, E, K, L, M, V, W or Y,
$X_6$ is D, A, G, H, K, M, P, S or T,
$X_7$ is I, A, D, E, F, G, H, K, L, M, N, Q, S or Y,
$X_8$ is E, A, G, H, K, L, M, Q, R, V, W or Y,
$X_9$ is G, E, R or W,
$X_{10}$ is V, L, P, W or Y,
$X_{11}$ is K, G or N,
$X_{12}$ is K or Q, and
$X_{13}$ is I or L.

In some embodiments, a CD98c-binding moiety of the invention forms all or part of a single variable domain antibody, a bi-or tri-functional VNAR, a part of a conventional antibody, or any fragment or fusion protein of said antibody. Such single variable domain antibody can be a shark antibody, a camelid antibody or a nanobody. The VNAR domain of the invention can also be part of a conventional antibody such as an immunoglobin having both heavy and light chains such as IgM, IgA, IgG or IgE, a single chain Fv, an Fab fragment, or any fragment or fusion protein of said antibody or fragment. For example, such antibodies may be prepared by grafting the CDR and HV regions of the VNAR onto the corresponding regions of the Ig.

Another aspect of the invention is directed to an CD98hc-binding moiety of the invention conjugated to a heterologous molecule which differs in biological activity from the moiety. For example, the conjugate may be operably linked to the CD98hc-binding moiety by a covalent or non-covalent linkage. Exemplary heterologous molecules, include but are not limited to, growth factors, cytokines, lymphokines, cell surface antigens, antibodies or antibody fragments for any of the foregoing. Further exemplary heterologous molecules include, but are not limited to, small molecule drugs, especially those for treating a CNS disorder or disease; other therapeutic agents or drugs; diagnostic agents such as a fluorescent molecule, phosphorescent, radionuclide or other molecular marker; or a nucleic acid molecule with regulatory properties or which encodes a regulatory molecule for a cell; as well as DNA, RNA, or hybrid DNA-RNA.

A further aspect of the invention relates to nucleic acid molecules encoding at least one CD98hc-binding moiety or conjugate of the invention, as well as vectors capable of introducing those nucleic acid molecules into a host cell. Vectors of the invention may further comprise expression control sequences to enable expression of the nucleic acid molecule in the host cell to thereby produce at least one binding moiety or conjugate. Host cells of the invention comprise one or more vectors of the invention.

In accordance with the invention, another aspect provides methods of producing at least one CD98hc binding moiety or conjugate by culturing host cells of the invention for a time and under conditions in a growth medium which enables the host cells to express the at least one CD98hc binding moiety or conjugate. In a preferred embodiment, the at least one binding moiety or conjugate produced by the host cell is secreted into the growth medium.

In yet another aspect, the invention relates to pharmaceutical compositions comprising a CD98hc binding moiety or conjugate of the invention in admixture with a pharmaceutically acceptable carrier.

The invention also relates to methods of medical treatment by administering a therapeutically-effective amount of a pharmaceutical composition of the invention to deliver a diagnostic or therapeutic agent to the brain of a mammalian subject in need thereof.

In some embodiments, the CD98hc binding moieties of the invention are used in a method of targeting delivery of a payload to brain parenchymal tissue in a mammal by administering that moiety or a conjugate thereof. For example, the complex with the payload is endocytosed into the cell and then released.

The present invention also provides kits for detecting or quantifying CD98hc in a sample which comprise at least one CD98hc binding moiety or conjugate of the invention.

In some embodiments, compound for use as a diagnostic or therapeutic agent in a subject, comprise a diagnostic or therapeutic agent operably linked to a CD98hc binding moiety of the invention, such that the binding moiety is endocytosed to thereby deliver said diagnostic or therapeutic agent across the cell membrane. The operable linkage of the agent allows dissociation to occur after endocytosis and to thereby release the said diagnostic or therapeutic agent into the cell. In preferred embodiments, the cell membrane is part of the blood brain barrier or one or more tissues, cells or organs selected from the group consisting of a tumor, a lymphocyte, a lymph node, a parathyroid gland, a kidney, a pancreatic s tissue, an esophageal tissue and a placenta.

Another aspect of the invention provides a method of delivering a therapeutic or diagnostic molecule across the blood brain barrier which comprises administering to a subject in need thereof a CD98hc binding moiety of the invention which has a therapeutic molecule conjugated thereto for a time and in an amount effective to treat or diagnose a CNS disease or condition.

Still another aspect of the invention provides a method of delivering a therapeutic or diagnostic molecule across the blood brain barrier which comprises administering a CD98hc binding moiety of the invention which has a therapeutic molecule conjugated thereto, to a subject for a time and in an amount effective to treat or diagnose a GI disease or condition.

In some embodiments, the invention provides a method of increasing the oral bioavailability of a drug which comprises associating the drug with a CD98hc-binding moiety the invention and administering such a complex to a subject in need thereof.

In a further aspect, the instant invention provides a composition comprising a plurality of 50 or more semi-synthetic polypeptides comprising Type IV VNAR framework (FW), hypervariable (HV) and complementary determining region (CDR) regions having a domain structure, from N- to C-terminus of

FW1-CDR1-FW2-HV2-FW2'-HV4-FW3-CDR3-FW4, wherein the framework regions FW1, FW2, FW2', FW3 and FW4 are from a Type IV VNAR domain or a structurally equivalent variant thereof, CDR1 comprises XXXXALA (SEQ ID NO. 375), and CDR3 comprises VY[X]$_z$DV (SEQ ID NO. 376), wherein X is any amino acid except for cysteine and z ranges from 3 to 21.

In some embodiments of the library, the Type IV VNAR domain comprises an amino acid sequence of:

```
ARVDQTPQTITKEEGESLTINCVLRXXXXAL

ASTSWYRKKSGSTREETISKGGRYVETVNSG

SKSFSLRINDLTVEDSGTYRCNVY[X]_zDV

YGDGTAVTVNA
(from SEQ ID NO. 364 when z is 13),
``` wherein X is any amino acid except for cysteine.

The foregoing embodiment include those wherein the CDR3 of each synthetic polypeptide is from 7 to 25, from 9 to 20 or from 11 to 18 amino acid residues in length as well as CDR3s wherein is 13.

Similarly, in some embodiments, the semi-synthetic polypeptides are encoded by a phage display library.

Any of the polypeptide libraries of the invention can be prepared as the corresponding nucleic acid library. Such libraries can have from 50 to $2\times10^{12}$ or from 50 to $2\times10^{10}$, or more molecules, having theoretically distinct nucleic acid sequences. In some embodiments the nucleic acid libraries of the invention are phage display libraries.

In a further aspect, the libraries of the invention can be used in methods of identifying a polypeptide that binds selectively to a target molecule of interest which comprises: (a) exposing a target molecule of interest to polypeptides of a polypeptide composition of the invention or to polypeptides produced by expression of a nucleic acid library of the invention; and (b) separating polypeptides that selectively bind from those that do not selectively bind the target molecule.

In some embodiment of this method, the target molecule of interest is expressed on the surface of a phage, bacterium or cell, or is attached to, tethered to or otherwise associated with a solid support. In some embodiments, the method further comprises (c) identifying high affinity binders from the polypeptide binders, wherein high affinity binders have an affinity of from about 0.1 nM to 250 nM, 1 nM to 250 nM, 10 nM to 250 nM, 50 nM to 250 nM, 100 nM to 250 nM, 0.1 nM to 100 nM, 1 nM to 100 nM, 10 nM to 100 nM, 50 nM to 100 nM, 0.1 nM to 50 nM, 1 nM to 50 nM, 5 nM to 50 nM, 10 nM to 50 nM, 0.1 nM to 25 nM, 1 nM to 25 nM, 5 nM to 25 nM, or 10 nM to 25 nM.

Additional methods for using the libraries of the invention include a method of screening a library for a polypeptide that selectively binds with high affinity to a target molecule of interest, the library comprising a plurality of polypeptides of the invention, wherein the method comprises (a) incubating a sample of the library with a concentration of a target molecule under conditions suitable for specific binding of the polypeptides to the molecule; (b) incubating a second sample of the library under the same conditions but without target molecule; (c) contacting each of the first and second sample with immobilized target molecule under conditions suitable for binding of the polypeptide to the immobilized target antigen; (d) detecting the polypeptide bound to immobilized target molecule for each sample; and (e) determining the affinity of the polypeptide for the target molecule by calculating the ratio of the amounts of bound polypeptide from the first sample over the amount bound polypeptide from the second sample.

In yet another embodiment, the invention is directed to a method of identifying one or more polypeptides that selectively bind to a target molecule of interest which comprises: (a) contacting said target molecule with a phage display library encoding a polypeptide composition of the invention; (b) separating phage that selectively bind said target molecule from those that do not selectively bind said target molecule to produce an enriched phage library; (c) repeating steps (a) and (b) with the enriched phage library to produce a further enriched phage library; (d) repeating step (c) until the further enriched phage library is enriched from at least about 10- to about $10^6$-fold or more relative to the original phage library; and (e) plating this last, even further enriched phage library to obtain single colonies that can be isolated and characterized to thereby identifying one or more polypeptides that selectively bind to a target molecule of interest. In some embodiments, the target molecule or the phage display library is bound to or attached to a solid support. The foregoing methods are useful to isolate any target molecule of interest, including but not limited to, CD98hc, BAFF, TfR or myostatin, and may be especially useful to obtain species cross reactive VNARs.

BRIEF DESCRIPTION OF THE DRAWINGS

FIG. 1. Type IV pilot library. (A) A VNAR scaffold was selected based on stability and expression level and (B) a pilot library was generated by randomizing 4 amino acids in the CDR1 and 13 amino acids in CDR3 using any amino acid except cysteine. The amino acid sequence of the VNAR domain in (A) is SEQ ID NO. 20 and in (B) is SEQ ID NO. 364.

DETAILED DESCRIPTION OF THE INVENTION

Figure 2:
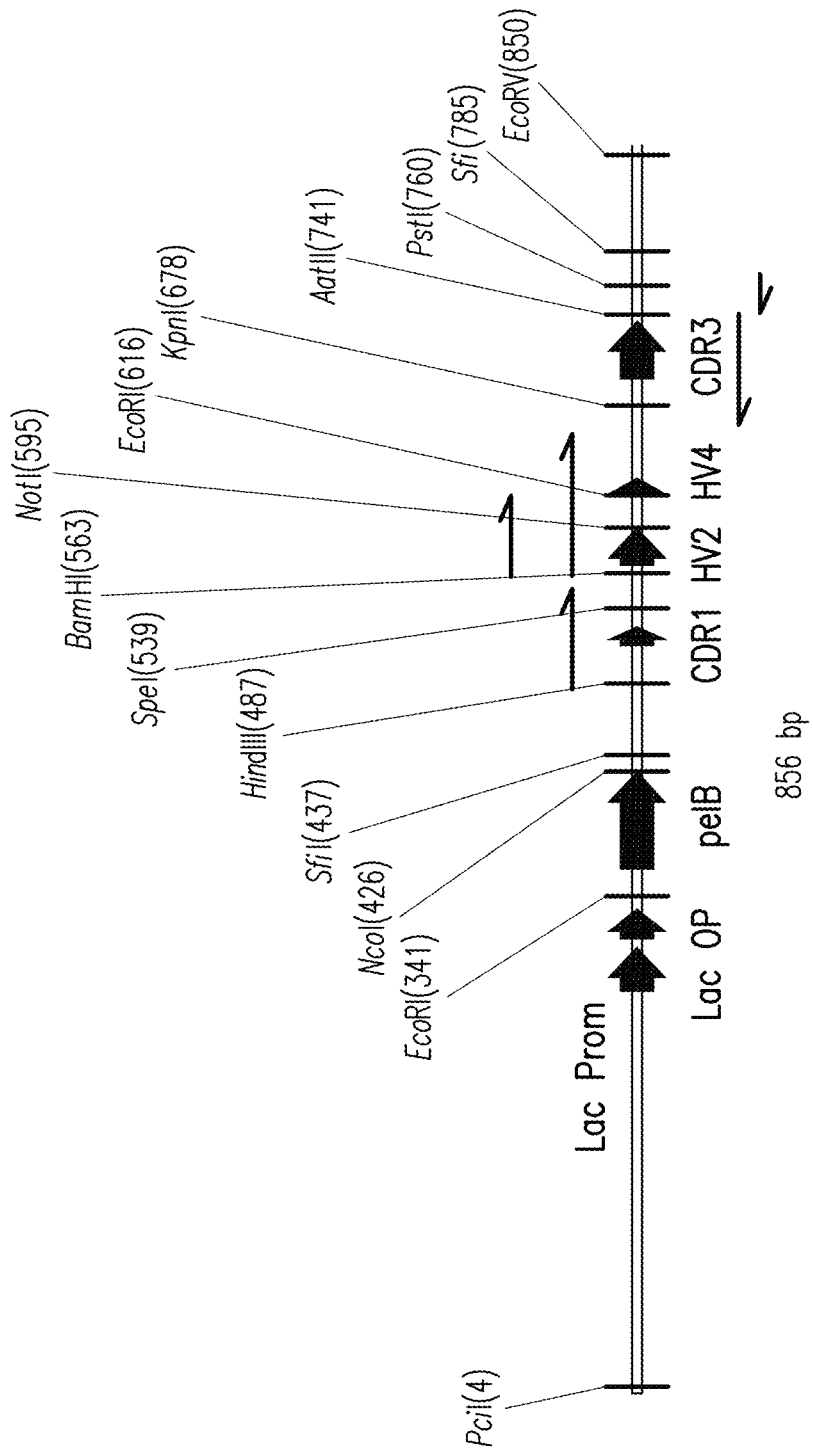
FIG. 2. Universal Type IV VNAR scaffold for library generation. The modular structure defined by restriction sites allows modifications to each variable site (CDR1, CDR3, HV2 and HV4) either alone or in combination to create a series of libraries that can be combined or used independently. Additionally, the modular scaffold simplifies the process of affinity maturation of binders to a particular antigen identified after library selection and screening.

In order that the present invention may be more readily understood, certain terms are defined below. Additional definitions may be found within the detailed description of the invention.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "plurality" as used herein refers to the number of members of a collection, which minimum is at least 10, 20, 30, 50, 75, 100, 1000 or more, and which minimum or maximum number may not be readily ascertainable but which may be indicated by type of collection or the context of its use. For example, a phage display library contains a plurality of phage equal to its titer (which may be the same or different), and by extension encodes a plurality of polypeptides.

The term "including" is used to mean "including but not limited to." "Including" and "including but not limited to" are used interchangeably.

The symbol "#" when used as the column header in any table depicting amino acid or nucleic acid sequences is short hand notation for "SEQ ID NO." and the number thereunder is the actual SEQ ID NO. in the Sequence Listing for the given sequence (unless indicated differently in a specific table).

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

The term "non-human mammal" means a mammal which is not a human and includes, but is not limited to, a mouse, rat, rabbit, pig, cow, sheep, goat, dog, primate, or other non-human mammals typically used in research.

As used herein, "treating" or "treatment" and grammatical variants thereof refer to an approach for obtaining beneficial or desired clinical results. The term may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (i.e., not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g., a human) in need of treatment may thus be a subject already afflicted with the disease or disorder in question. The term "treatment" includes inhibition or reduction of an increase in severity of a pathological state or symptoms relative to the absence of treatment and is not necessarily meant to imply complete cessation of the relevant disease, disorder or condition.

As used herein, the terms "preventing" and grammatical variants thereof refer to an approach for preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g., a human) in need of prevention may thus be a subject not yet afflicted with the disease or disorder in question. The term "prevention" includes slowing the onset of disease relative to the absence of treatment and is not necessarily meant to imply permanent prevention of the relevant disease, disorder or condition. Thus "preventing" or "prevention" of a condition may in certain contexts refer to reducing the risk of developing the condition or preventing or delaying the development of symptoms associated with the condition.

As used herein, an "effective amount," "therapeutically-effective amount" or "effective dose" is an amount of a composition (e.g., a therapeutic composition or agent) that produces at least one desired therapeutic effect in a subject, such as preventing or treating a target condition or beneficially alleviating a symptom associated with the condition.

A physiologically-acceptable solution for use in an amount and for a time sufficient to effectively reduce a circulating concentration of the plurality of polypeptides is also referred to herein as a perfusate. The amount of perfusate and time of perfusion depends on the non-human mammal and can be readily determined by those of skill in the art. For example, with a mouse, using a volume of perfusate approximately 10× the blood volume of the mouse is effective at reducing the circulating concentration of polypeptides. Likewise, any volume of perfusate that reduces the circulating concentration of the plurality of polypeptides by about 10%, 25%, 50% or more (relative to the theoretical concentration of the plurality of polypeptides) being delivered is considered effective at reducing the circulating concentration of that plurality.

As used herein, a "VNAR domain" has the general structure, from N to C terminus, given by the formula FW1-CDR1-FW2-HV2-FW2'-HV4-FW3-CDR3-FW4, wherein the FWs are framework regions, CDRs are complementarity determining regions and HVs are hypervariable regions that form the variable domain of a shark IgNAR ("VNAR"). The CDR3 region in naturally-occurring VNARs is of heterogeneous size, ranging from about 7 to about 32 amino acid residues in length. The VNAR domains of the invention can optionally have a His-Tag (or other convenient tag for purification purposes). In some cases, such tags are removable.

As used herein, binding to the target of interest is called specific binding, while binding to other sites is called nonspecific binding. As used herein, a binding moiety, specific binding moiety, antibody or VNAR domain that "specifically binds" to its target does so selectively or preferentially. Such moieties, antibodies and VNARS can exhibit specific binding to multiple targets such as occurs when one of these entities exhibits species cross reactivity.

The term "CD98 heavy chain" or "CD98hc" as used herein, refers to any native CD98hc from any vertebrate source, including mammals such as primates (e.g., humans) and rodents (e.g., mice and rats), unless otherwise indicated. CD98hc is also known by the names, inter alia, SLC3A2, 4F2, 4F2hc, Mdu1, LyIO, Mdvl, Frp1, Mgp2, Mgp2hc, NACAE, 4T2, 4T2hc, and TROP4. The amino acid sequence of human CD98hc is provided in GenBank® sequence database ("GenBank") Accession Nos. NP_001012680.1 (isoform b), NP_002385.3 (isoform c), NP_001012682.1 (e), and NP_001013269.1 (isoform f), respectively, and for murine CD98hc ("mCD98hc"), in GenBank® Accession No.: NP_001154885.1 (isoform a) and NP_032603.3 (isoform b).

Type IV VNAR Semi-Synthetic Library Construction

The VNAR domain has the basic structure of an Ig variable domain with two sheets held together by two canonical cysteine residues that stabilize the framework. Unlike Ig variable domains, however, VNARs typically have one or two additional disulfide bonds and are classified into four isoforms based on the number and position of these non-canonical cysteines (21). Semi-synthetic VNAR libraries based on the Type I and Type II VNAR isoforms are available (WO2015/200883, published Dec. 30, 2015). The Type I VNAR contains non-canonical cysteines in CDR3 that form two disulfide bonds with cysteine in the framework and has only been reported in the nurse shark (*Ginglymostoma cirratum*) to date. The Type II VNAR, which is the most predominant isoform among the various shark species, is distinguished by a disulfide bond between a cysteine in CDR3 and another cysteine in CDR1.

The additional disulfide bonds in both Type I and Type II VNARs serve to stabilize and orient the CDR3 such that it can protrude into binding pockets and grooves (22). In addition to Types I and II, rarer VNAR variants can be found in the natural repertoire, namely Type IIb (23, 24) and, more recently reported, Type IV (19). Type IV VNARs contain the framework cysteines that form the Ig fold but lack any additional cysteines. Therefore, the CDR3 of the Type IV VNAR domain is not physically constrained by a disulfide bridge, allowing more conformational freedom and flexibility in its interaction with antigen. Despite being underrepresented relative to other isoforms (25), Type IV VNARs that bind with high affinity to target antigens have been isolated from naïve or immune libraries (24, 26).

To further characterize and exploit the properties of this unique structure, a dedicated Type IV VNAR phage display library was designed. The scaffold was chosen based on the favourable properties of a particular Type IV VNAR, including high monomer expression and secretion, high monomer stability (>3 months at 4° C.) and low number of post translational modification sites (FIG. 1A). This library, as well as all the libraries of the invention, can be designed for assembly via a modular structure which allows modifications to each variable site (CDR1, CDR3, HV2 & HV4). For example, the portion of the vector depicted in FIG. 2, shows a restriction map that provides the modular structure and restriction sites for assembling Type IV libraries of the invention. This modular structure is also useful in constructing libraries for VNAR domains of other isoforms. Hence, one embodiment of the invention is directed to a vector comprising a VNAR domain operably linked to a heterologous promoter, wherein the VNAR domain can be assembled from one or more modular fragments independently encoding at least one of the CDR1, HV2, HV4 or CDR3 regions of the VNAR. In a preferred embodiment, that vector comprises the VNAR domain obtained from the modular design depicted in FIG. 2, i.e., by having at least the VNAR domain coding nucleic acid sequence include the indicated restriction sites. Similar modularity can be used to operably join a heterologous promoter. To be clear, since various methods of assembling nucleic acids are known in the art (PCR, joining restriction fragments and the like), the modular fragments need not be on a single nucleic acid fragment before assembly. Further design considerations to produce a vector of the invention are within the skill of one of ordinary skill in the art.

In one embodiment, a library can be generated by randomizing four amino acid residues in CDR1 and 13 amino acid residues in CDR3 using any amino acid except cysteine (FIG. 1B). Methods to make this library and all libraries of the invention include focused NNK mutagenesis, site-directed mutagenesis, trimer technology, and for peptide libraries, direct chemical synthesis. It should be noted that the focused NNK mutagenesis can introduce both cysteine residues and stop codons but use of this method still produces useful Type IV VNAR libraries of the invention, because there is a low likelihood of simultaneously having two cysteines positioned to form a disulfide bridge, and because, like with truncations, the size of the library is sufficiently large enough and diverse enough to produce many suitable VNARs to bind to targets of interest during the screening process. For example, a library formed by focused NNK mutagenesis had a size estimated at $10^8$-$10^9$ unique clones with 70% of sequences in frame and >70% of clones displaying at >15% of phage PIII protein as determined by ELISA or Western blot.

Accordingly, one aspect of the present invention relates to new semi-synthetic Type IV VNAR libraries based on nurse shark framework sequences. In some embodiments the frameworks are naturally occurring sequences and, in some embodiments, such frameworks can incorporate substitutions (or other small insertions or deletions) so that the framework retains the structural properties of a Type IV VNAR. Useful frameworks include, for example, the one in FIG. 1A, the Type IV framework regions in the VNAR domain in Table 1A, and framework changes disclosed in WO2015/200883, generally (as discussed the preceding paragraph) excluding any change that could introduce a cysteine residue in a manner that would not preserve the Type IV domain structure.

Hence, libraries of the invention comprise synthetic polypeptide compositions and/or nucleic acid molecules encoding them and may be used in assays, e.g., in phage display libraries, to identify and select sequences within the synthetic library which bind selectively to one or more molecular mammalian target molecules of interest. Libraries of the invention enable the generation of novel therapeutic products, in particular, specific binding moieties which bind selectively and with high affinity to a select cellular target, thereby producing a target antagonist compound or mimicking the activity of a native molecule. Exemplary binding moieties and molecular target antagonist compounds which may be identified and isolated using the semi-synthetic libraries of the invention include, inter alia, high affinity polypeptide binding domains specific for species cross reactive proteins, such as those described herein against human and mouse CD98hc, as well as use for other targets of interest such as human BAFF, human transferrin receptor hTrR-1, myostatin and other antigens.

Accordingly, in certain embodiments, the present invention provides a library composition comprising a plurality of semi-synthetic polypeptides which encode a Type IV VNAR framework (FW), hypervariable (HV) and complementary determining region (CDR) regions having a domain structure, from N- to C-terminus of

FW1-CDR1-FW2-HV2-FW2'-HV4-FW3-CDR3-FW4, wherein the framework regions FW1, FW2, FW2', FW3 and FW4 are from a Type IV VNAR domain or a structurally equivalent variant thereof, CDR1 comprises XXXXALA (SEQ ID NO. 375), and CDR3 comprises VY[X]$_z$DV (SEQ ID NO. 376), wherein X is any amino acid except for cysteine and z ranges from 3 to 21. In some embodiments, z is 6, 8, 10, 12, 14, 16, 18 or 20. In a preferred embodiment, z is 13.

In some embodiments, the library is a polypeptide composition comprising a plurality of semi-synthetic polypeptides whose members encode a Type IV VNAR domain comprising the amino acid sequence of:

```
                                        (SEQ ID NO. 364)
ARVDQTPQTITKEEGESLTINCVLRXXXXALASTSWYRKKS

GSTREETISKGGRYVETVNSGSKSFSLRINDLTVEDSGTYR

CNVYXXXXXXXXXXXXXXDVYGDGTAVTVNA,
``` wherein X is any amino acid except for cysteine.

The libraries of the invention include the foregoing polypeptide libraries as well as nucleic acid libraries encoding such polypeptide compositions, and the phage display libraries encoding such polypeptides. In some embodiments, a plurality is 50 or more or as defined herein (see above). In those embodiments of the polypeptide compositions produced by a phage display library, the composition can have from 100 to $10^{10}$ polypeptides as determined by the phage titer.

In any of the above embodiments, the CDR3 region of each synthetic polypeptide may vary in length from 7 to 25 amino acid residues, from 9 to 20 amino acid residues and often from 11 to 18 amino acid residues in length.

In certain embodiments, polypeptide compositions of the invention may further comprise at least one engrafted HV2, HV4, CDR1 or CDR3 domain obtained from a heterologous antibody directed to a select mammalian molecular target. In such a case, the structural integrity of the engrafted molecule can maintain the Type IV domain structure by deleting cysteine residues in either CDR1 or CDR3 to ensure a cysteine bridge does not form. Similarly, synthetic polypeptides within compositions of the invention may comprise at least one engrafted domain FW1, FW2, FW2', FW3 or FW4 obtained from a heterologous antibody directed to a select molecular target. In certain embodiments, one or more heterologous antibody domain engraftments are designed into a VNAR domain template in the process of generating a library of the invention. In certain embodiments, one or more heterologous antibody domains are engrafted into polypeptide(s) after such polypeptides are identified, selected or isolated from a semi-synthetic VNAR library of the invention to further refine characteristics of the binding moiety, e.g., to increase affinity or selectively of the moiety for a molecular target. Embodiments relating to heterologous antibody domain grafting may be performed individually or in any combination and are not intended to be mutually exclusive.

In another embodiment, the present invention provides a nucleic acid composition, e.g., a nucleic acid library, comprising a plurality of nucleic acid molecules encoding any polypeptide library or polypeptide composition of the invention. In certain embodiments, the invention provides a library of phage or phagemid particles displaying a plurality of polypeptides of the invention. In certain embodiments, a nucleic acid library of the invention comprises from $0.5 \times 10^2$ to $2 \times 10^{10}$ or more molecules having distinct nucleic acid sequences (the upper limit being based on obtainable phage titers). A nucleic acid molecule of the invention or a fragment thereof may be inserted into or used to engineer a vector, e.g., an expression vector which is capable of producing in an appropriate host cell a polypeptide or polypeptide composition of the invention. In yet another embodiment, the invention provides a composition of vectors such as expression vectors comprising a plurality of nucleic acid molecules encoding a plurality of polypeptides of the invention. Host cells comprising a vector or composition of vectors of the invention are also provided.

Accordingly, the present invention further provides a method of identifying a polypeptide that binds selectively to a target molecule of interest, the method comprising the steps of: a) exposing a target molecule of interest to a composition comprising a plurality of polypeptides of the invention (or by expression of a nucleic acid molecule or composition of the invention); and b) separating polypeptides that selectively bind from those that do not selectively bind the target molecule. In certain embodiments, a target molecule of interest is expressed on the surface of a phage, bacterium or cell, or is attached to, tethered to or otherwise associated with a solid support.

In certain embodiments, a method of the invention may further comprise a step of: c) identifying high affinity binders from the polypeptide binders, wherein high affinity binders have an affinity of from about 0.1 nM to 250 nM, 1 nM to 250 nM, 10 nM to 250 nM, 50 nM to 250 nM, 100 nM to 250 nM, 0.1 nM to 100 nM, 1 nM to 100 nM, 10 nM to 100 nM, 50 nM to 100 nM, 0.1 nM to 50 nM, 1 nM to 50 nM, 5 nM to 50 nM, 10 nM to 50 nM, 0.1 nM to 25 nM, 1 nM to 25 nM, 5 nM to 25 nM, or 10 nM to 25 nM.

In certain embodiments, the present invention further provides a method of screening a library of the invention for a polypeptide that selectively binds with high affinity to a target molecule of interest, the method comprising the steps of: a) incubating a sample of the library with a concentration of a target molecule under conditions suitable for specific binding of the polypeptides to the molecule; b) incubating a second sample of the library under the same conditions but without target molecule; c) contacting each of the first and second sample with immobilized target molecule under conditions suitable for binding of the polypeptide to the immobilized target antigen; d) detecting the polypeptide bound to immobilized target molecule for each sample; and e) determining the affinity of the polypeptide for the target molecule by calculating the ratio of the amounts of bound polypeptide from the first sample over the amount bound polypeptide from the second sample.

Yet a further example of an embodiment of the invention provides a method of identifying one or more polypeptides that selectively bind to a target molecule of interest which comprises (a) contacting a target molecule with a phage display library encoding the polypeptides of the composition of the invention or with any other phage display library of the invention, (b) separating phage that selectively bind said target molecule from those that do not selectively bind said target molecule to produce an enriched phage library; (c) repeating steps (a) and (b) with the enriched phage library to produce a further enriched phage library; (d) repeating step (c) until the further enriched phage library is enriched from at least about 10- to about $10^6$-fold or more relative to the original phage library; and (e) plating the further enriched phage library, isolating and characterizing individual clones therefrom and thereby identifying one or more polypeptides that selectively bind to a target molecule of interest. The number of cycles needed to obtain a sufficiently further enriched phage library to readily isolate the desired, individual clones typically ranges from three to eight rounds of selection and more typically can be done with 3-4 rounds of selection. In this method, either the target molecule or the phage display library can be bound to or attached to a solid support to facilitate selective binding (and simplify wash conditions, which stringency can be varied in successive rounds (see, the Examples). Any method known in the art for eluting and recovering bound phage can be used.

Polypeptide Sequences and Compounds Comprising a CD98hc Specific VNAR

The present invention provides a CD98hc-specific binding moiety, e.g., a polypeptide comprising a CD98hc-binding VNAR domain; CDR98hc mediated drug vehicles that can carry heterologous molecules across the membrane of a CD98hc-positive cell; and CD98hc antagonist compounds comprising at least one CD98hc-specific binding moiety. Isolated CD98hc-binding VNAR domains are also provided. In certain embodiments, the CD98hc-specific binding moiety is specific for a mammalian CD98hc. In certain embodiments, the CD98hc-binding moiety is specific for human CD98hc. In certain embodiments, the CD98hc-specific binding moiety is a component of a BBB vehicle and mediates endocytosis of an associated heterologous molecule across a cell membrane, and in particular, across the BBB. In certain embodiments, the CD98hc-specific binding moiety mediates endocytosis without blocking ligand binding.

Hence, in accordance with the invention, certain embodiments of CD98hc-specific binding moieties comprise a VNAR domain capable of specifically binding to human CD98hc and murine CD98hc, wherein said VNAR domain is represented by the formula, from N to C terminus,

FW1-CDR1-FW2-HV2-FW2'-HV4-FW3-CDR3-FW4, and wherein CDR3 has an amino acid sequence as shown in Table 1B. In some embodiments, the VNAR domain has an amino acid sequence as shown in Table 1A.

In some embodiments, the isolated CD98hc-specific binding moiety comprises a Type IV VNAR domain capable of specifically binding to human CD98hc and murine CD98hc and is represented by the formula, from N to C terminus, FW1-CDR1-FW2-HV2-FW2'-HV4-FW3-CDR3-FW4, wherein CDR1 has an amino acid sequence as shown in Table 1B, HV2 has an amino acid sequence of TREETISKG (SEQ ID NO. 1) or SREETISKG (SEQ ID NO. 2), HV4 has an amino acid sequence of NSGSKS (SEQ ID NO. 3) and wherein the CDR3 region consists of an amino acid sequence of formula (SEQ ID NO. 4)
V-Y-$X_1$-$X_2$-$X_3$-$X_4$-$X_5$-$X_6$-$X_7$-$X_8$-
$X_9$-$X_{10}$-$X_{11}$-$X_{12}$-$X_{13}$-D-V, wherein
$X_1$ is A, E, F, G or I,
$X_2$ is E, F, I, L, R or Y,
$X_3$ is H, L, P, R, S, V or Y,
$X_4$ is A, E, F, I, S or Y
$X_5$ is F, G, I, P, S or V,
$X_6$ is A, D, E, L, Q, S or T,
$X_7$ is C, E, F, I, K, P or V,
$X_8$ is D, E, K, N or T
$X_9$ is A, G, I, K, Q or V
$X_{10}$ is A, K, L, R, V or Y $X_{11}$ is E, G, H, K, P, Q or Y
$X_{12}$ is D, E, F, G, K, P, S, T or Y, and
$X_{13}$ is F, H, I, N, Q or R.

In some embodiments, the CD98hc-specific binding moiety has an EC50 for human CD98hc ranging from about 0.1 nM to about 10 µM and preferably ranging from about 1 nM to about 800 nM. In some embodiments, the CD98hc-specific binding moieties of the invention are capable of crossing the blood brain barrier.

In another embodiment, the isolated CD98hc-specific binding moiety is clone F12 or a variant of clone F12 and comprises a Type IV VNAR domain capable of specifically binding to human CD98hc and murine CD98hc, wherein said VNAR domain is represented by the formula, from N to C terminus,

FW1-CDR1-FW2-HV2-FW2'-HV4-FW3-CDR3-FW4, wherein CDR1 has an amino acid sequence of VHGRALAS (SEQ ID NO. 374), HV2 comprises an amino acid sequence of TREETISKG (SEQ ID NO. 1), HV4 comprises an amino acid sequence of NSGSKS (SEQ ID NO. 3), and CDR3 comprises an amino acid sequence of formula (SEQ ID NO. 5)
V-$X_1$-G-$X_2$-$X_3$-$X_4$-$X_5$-$X_6$-$X_7$-$X_8$-
$X_9$-$X_{10}$-$X_{11}$-$X_{12}$-$X_{13}$-D-V, wherein
$X_1$ is Y, D, F, H, K, N, S or W,
$X_2$ is L or V,
$X_3$ is S, G, E, K, L, M, Q or R,
$X_4$ is F, A, G, H, I, K, L, M, N, Q, R, S, T, W or Y,
$X_5$ is G, E, K, L, M, V, W or Y,
$X_6$ is D, A, G, H, K, M, P, S or T,
$X_7$ is I, A, D, E, F, G, H, K, L, M, N, Q, S or Y,
$X_8$ is E, A, G, H, K, L, M, Q, R, V, W or Y,
$X_9$ is G, E, R or W,
$X_{10}$ is V, L, P, W or Y,
$X_{11}$ is K, G or N,
$X_{12}$ is K or Q, and
$X_{13}$ is I or L.

In this formula, the CDR3 for clone F12 is given by the first residue for each X. In some embodiments, F12 and its variants are also capable of crossing the blood brain barrier.

In yet another aspect of the invention, any of the CD98hc-specific binding moieties can form all or part of the variable domain of a single variable domain antibody, a bi- or tri-functional VNAR, a conventional antibody, or any fragment or fusion protein of said antibody as well as variable domains with antibody-like backbones.

Examples of single variable domain antibodies include, but are not limited to, a shark or other cartilaginous fish antibodies, camelid antibodies and nanobodies. Examples conventional antibodies include, but are not limited to, immunoglobins having both heavy and light chains, such as IgM's, IgA's, IgG's, IgE's, single chain Fv's, Fab fragments, or any fragment or fusion protein of such antibodies or fragments.

Non-limiting examples of antibody-like backbones that may be used according to the invention include monospecific and bispecific such as multimerizing scFv fragments (diabodies, triabodies, tetrabodies), disulfide stabilized antibody variable (Fv) fragments, disulfide stabilized antigen-binding (Fab) fragments consisting of the $V_L$, $V_H$, $C_L$ and $C_H$1 domains, bivalent F(ab')2 fragments, Fd fragments consisting of the heavy chain and $C_H1$ domains, dimeric $C_H2$ domain fragments ($C_H2D$), Fc antigen binding domains (Fcabs), single chain Fv-$C_H3$ minibodies, bispecific minibodies, isolated complementary determining region 3 (CDR3) fragments, constrained FR3-CDR3-FR4 polypeptides, SMIP domains, and any genetically manipulated counterparts of the foregoing that retain CD98hc-1 binding function (see e.g., references 27 and 28 for reviews).

Therefore, in one aspect, the invention provides a CD98hc-selective compound comprising or consisting essentially of a VNAR derived CD98hc-specific binding moiety which binds selectively to a CD98hc polypeptide, preferably to human CD98hc.

In certain embodiments, a CD98hc-specific binding moiety of the invention binds to any of the CD98hc complexes, including the LAT1/CD98hc complex on the membrane of a mammalian cell and CD98hc-specific binding mediates transport of the CD98hc-specific binding moiety and at least one associated heterologous molecule across the cell membrane. Any CD98hc-positive cell or cell type (i.e., one with the transferrin receptor localized at the cell membrane) may thus be used to target delivery of heterologous molecules across its membrane by association (e.g., a complex or conjugate) with a CD98hc specific binding moiety of the invention. As described in more detail below, heterologous molecules may be selected from an enormously wide variety of agents, limited only by the target cell requiring a cell surface CD98hc which can internalize upon binding.

In certain embodiments of the invention, the cell membrane is part of the blood brain barrier (BBB) and CD98hc-mediated transport across the BBB of a heterologous molecule may be accomplished. In certain other embodiments of the invention, the cell membrane is from other tissues and cells, including tumors cells, lymphocytes, lymph nodes, the parathyroid gland, kidneys, pancreatic tissue, esophageal tissue and the placenta. In some embodiments, CD98hc-mediated transport of a heterologous molecule may be accomplished, enabling oral drug delivery routes, especially advantageous for previously non-orally bioavailable drugs or molecules for therapeutics and/or diagnostics.

Associated heterologous molecules which may be used in conjunction with any one of the above embodiments may comprise, e.g., one or more biologically active molecules and/or imaging agents. Exemplary biologically active molecules which may be transported into a CD98hc-positive cell in association with a CD98hc-specific binding moiety of the invention include, e.g., toxins for targeted CD98hc-positive cell death (useful e.g., in certain hyperproliferative diseases or disorders such as cancers or aberrant proliferative conditions). Other exemplary biologically active molecules which may be transported in association with a CD98hc-specific binding moiety include, e.g., polypeptides, such as an antibody or antibody fragment; a therapeutic peptide such as a hormone, cytokine, growth factor, enzyme, antigen or antigenic peptide, transcription factor, or any functional domain thereof. Other exemplary biologically active molecules which may be transported into a CD98hc-positive cell in association with a CD98hc specific binding moiety include, e.g., nucleic acid molecules, such as an oligonucleotide (e.g., single, double or more stranded RNA and/or DNA molecules, and analogs and derivatives thereof); small regulatory RNA such as shRNA, miRNA, siRNA and the like; and a plasmid or fragment thereof.

Exemplary polypeptides which may be therapeutically beneficial when administered as a heterologous molecule for CD98hc-mediated transport across the BBB or other CD98hc-containing cell membrane include but are not limited to: a brain derived neurotrophic factor (BDNF), a bone morphogenic protein (e.g., BMP-1 through BMP-7, BMP8a, BMP8b, BMP10 and BMP15), a ciliary neurotrophic factor (CNF), an epidermal growth factor (EGF), erythropoietin, a fibroblast growth factor (FGF), a glial derived neurotrophic factor (GDNF), a heptocyte growth factor, an interleukin (e.g., IL-1, IL-4, IL-6, IL-10, IL-12, IL-13, IL-17), a nerve growth factor (NGF), a neurotrophin (e.g., NT-3 and NT-4/5), a neurturin, a neuregulin, a platelet derived growth factor (PDGF), a transforming growth factor (e.g., TGF-alpha and TGF-beta), a vasoactive intestinal peptide, artemin, persephin, netrin, cardiotrophin-1, stem cell factor, midkine, pleiotrophin, a saposin, a semaporin, leukemia inhibitory factor, and the like.

Exemplary therapeutic antibodies or fragments that may be transported across the BBB or other CD98hc-containing cell membrane as a heterologous biologically active molecule of the invention include but are not limited to: anti-Abeta, anti-Tau, anti-alpha-synuclein anti-Trem2, anti-C9orf7 dipeptides, anti-TDP-43, anti-prion protein C, anti-huntingtin, anti-nogo A, anti-TRAIL (tumor necrosis factor-related apoptosis-inducing ligand); antibodies for neuro-oncology including anti-HER2, anti-EGF, anti-PDGF, anti-PD1/PDL1, anti-CTLA-4, anti-IDO, anti-LAG-3, anti-CD20, anti-CD19, anti-CD40, anti-OX40, anti-TIM3, anti-toll-like receptors; antibodies for neuroinflammation including anti-TNF, anti-CD138, anti-IL-21, anti-IL-22; antibodies to viral diseases of the brain including anti-West Nile virus, anti-Zika, anti-HIV, anti-CMV, anti-HSV and the like.

Exemplary enzymes that may be transported across the BBB or other CD98hc-containing cell membrane as a heterologous biologically active molecule of the invention include but are not limited to: alpha-L-iduronidase, iduronate-2-sulfatase, N-acetyl-galactosamine-6-sulfatase, arylsulfatase B, acid alpha-glucosidase, and acid sphingomyelinase.

Also included as exemplary biologically active molecules are small molecules comprising chemical moieties (such as a therapeutic small molecule drugs); carbohydrates; polysaccharides; lipids; glycolipids and the like. Exemplary embodiments of such small molecule therapeutic agents include certain cancer drugs, such as daunorubicin, doxorubicin, and other cytotoxic chemical agents including microtubule inhibitors, topoisomerase inhibitors, platins, alkylating agents, and anti-metabolites all of which may beneficially be administered across the BBB at lower overall systemic doses than by IV administration. Other small molecule therapeutic agents may include corticosteroids, NSAIDs, COX-2 inhibitors, small molecule immunomodulators, non-steroidal immunosuppressants, 5-amino salicylic acid, DMARDs, hydroxychloroquine sulfate, and penicillamine. 1-D-ribofuranosyl-1,2,4-triazole-3 carboxamide, 9-2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir, among others. Small molecule therapeutic agents which may be used according to the invention also include bevacizumab, cisplatin, irinotecan, methotrexate, temozolomide, taxol and zoledronate. Certain anti-inflammatory agents may be useful biologically active molecules. Fluoxetine, for example, reportedly inhibits MMP-2, MMP-9 and MMP-12 expression associated with blood-brain barrier disruption and inflammatory reactions after spinal cord injury, may be used according to the invention to protect blood-brain barrier and to inhibit deleterious inflammatory responses in spinal cord injury and central nervous system disease.

Exemplary embodiments of an imaging agent as an associated heterologous molecule include agents that comprise at least one of a metal such as a paramagnetic metal, a radionuclide such as a radioisotope, a fluorochrome or fluorophor, an energy emitting particle, a detectable dye, and an enzyme substrate.

Further examples of biologically active molecules include small molecules, including therapeutic agents, in particular those with low blood-brain barrier permeability. Some examples of these therapeutic agents include cancer drugs, such as daunorubicin, doxorubicin, and toxic chemicals which, because of the lower dosage that can be administered by this method, can now be more safely administered. For example, a therapeutic agent can include bevacizumab, irinotecan, zoledronate, temozolomide, taxol, methotrexate, and cisplatin.

In another embodiment, the therapeutic agent can include a broad-spectrum antibiotic (e.g., cefotaxime, ceftriaxone, ampicillin and vancomycin); an antiviral agent (e.g., acyclovir); acetazolamide; carbamazepine; clonazepam; clorazepate dipotassium; diazepam; divalproex sodium; ethosuximide; felbamate; fosphenytoin sodium; gabapentin; lamotrigine; levetiracetam; lorazepam; oxcarbazepine; phenobarbital; phenytoin; phenytoin sodium; pregabalin; primidone; tiagabine hydrochloride; topiramate; trimethadione; valproic acid; zonisamide; copaxone; tysabri; novantrone; donezepil HCL; rivastigmine; galantamine; memantine; levodopa; carbidopa; parlodel, permax, requip, mirapex; Symmetrel; artane; cogentin; eldepryl; and deprenyl. Antiviral compounds are also beneficial therapeutic agents that can be delivered using a CD98hc-specific binding moiety of the invention, especially for cases in which the virus uses CD98hc transport as its route of entry into infected cells.

Numerous other examples of biologically active molecules may be used in association with a CD98hc-specific binding moiety of the invention, appropriate selection of which will be apparent to the skilled artisan depending on the condition, disease or disorder to be treated.

Yet other examples of a biologically active molecule which may be used according to the present invention is an antigenic peptide. Antigenic peptides may provide immunological protection when imported by cells involved in an immune response. Other examples include immunosuppressive peptides (e.g., peptides that block autoreactive T cells, such peptides being known in the art).

An imaging agent, as used herein, may be any chemical substance which may be used to provide a signal or contrast in imaging. A signal enhancing domain may be an organic molecule, metal ion, salt or chelate, a particle (e.g., iron particle), or a labeled peptide, protein, glycoprotein, polymer or liposome. For example, an imaging agent may include one or more of a radionuclide, a paramagnetic metal, a fluorochrome, a dye, and an enzyme substrate.

For x-ray imaging, the imaging agent may comprise iodinated organic molecules or chelates of heavy metal ions of atomic numbers 57 to 83. In certain embodiments, the imaging agent is $I^{125}$ labeled IgG (see, e.g., M. Sovak, ed., "Radiocontrast Agents," Springer-Verlag, pp. 23-125 (1984).

For ultrasound imaging, an imaging agent may comprise gas-filled bubbles or particles or metal chelates where the metal ions have atomic numbers 21-29, 42, 44 or 57-83. See e.g., Tyler et al., Ultrasonic Imaging, 3, pp. 323-29 (1981) and D. P. Swanson, "Enhancement Agents for Ultrasound: Fundamentals," Pharmaceuticals in Medical Imaging, pp. 682-87. (1990) for other suitable compounds.

For nuclear radiopharmaceutical imaging or radiotherapy, an imaging agent may comprise a radioactive molecule. In certain embodiments, chelates of Tc, Re, Co, Cu, Au, Ag, Pb, Bi, In and Ga may be used. In certain embodiments, chelates of Tc-99m may be used. See e.g., Rayudu G V S, Radiotracers for Medical Applications, I, pp. 201 and D. P. Swanson et al., ed., Pharmaceuticals in Medical Imaging, pp. 279-644 (1990) for other suitable compounds.

For ultraviolet/visible/infrared light imaging, an imaging agent may comprise any organic or inorganic dye or any metal chelate.

For MRI, an imaging agent may comprise a metal-ligand complex of a paramagnetic form of a metal ion with atomic numbers 21-29, 42, 44, or 57-83. In certain embodiments, the paramagnetic metal is selected from: Cr(III), Cu(II), Dy(III), Er(III) and Eu(III), Fe(III), Gd(III), Ho(III), Mn(II and III), Tb(III). A variety of chelating ligands useful as MRI agents are well known in the art.

In sum, the invention includes CD98hc-specific conjugate comprising a CD98hc-specific binding moiety of the invention operably linked to a heterologous molecule which differs in biological activity from said moiety. Such operable linkages can be a covalent or non-covalent linkage and the heterologous molecule can be a growth factor, cytokine, lymphokine, cell surface antigen or an antibody or antibody fragment which binds to any of the foregoing; a chimeric antigen receptor; a cytotoxic small molecule; a biochemical pathway agonist or antagonist; a therapeutic agent or drug; a diagnostic agent such as a fluorescent molecule or other molecular marker; or a nucleic acid molecule with targeting or other regulatory properties (e.g., silencers) or which encodes a regulatory molecule for a cell.

For the avoidance of doubt, a CD98hc-selective binding compound includes CD98hc-specific binding moieties alone, as part of antibodies (or fragments thereof as described herein) or as part of conjugates.

Monitoring CD98hc Binding and Cell Internalization

CD98hc-binding activity (also referred to herein as "CD98hc bioactivity") may be determined by one or more assays described in the Examples herein, or by any other suitable method in the art, including well-known immunoassays, such as for example the ELISAs or variations thereon described in the Examples. Any other binding assay which directly or indirectly measures the binding of the CD98hc-specific binding moiety to a cell surface CD98hc or CD98hc complex, or alternatively, which measures the ability of a CD98hc-specific binding moiety, conjugate or compound comprising such a moiety of the invention to compete for binding to CD98hc in the presence of a different CD98hc binding compound (such amino acids) such as by a competitive inhibition assay, may be used. Preferably, a selected assay measures the effect of a CD98hc-specific binding moiety or compound comprising such a moiety on its ability to transport a heterologous molecule or biomolecule across the membrane of a CD98hc-positive cell. In certain embodiments, the CD98hc-positive cell is one which transports a heterologous molecule across the blood brain barrier (BBB). In certain embodiments, the CD98hc-positive cell is one which transports a heterologous molecule across cells of the gastrointestinal tract. In certain embodiments, binding of the CD98hc binding moiety to CD98hc is measured by monitoring internalization of the CD98hc binding moiety into CD98hc-positive cells or cell type. In vivo assays of CD98hc bioactivity include but are not limited to those described in the Examples herein.

Other test systems to assess CD98hc binding and functional activity include, for example: Surface plasmon resonance to determine affinity and off-rates; using radiolabeled or fluorescent tagged molecule or GFP fusion proteins in in vitro or in vivo animal studies including binding and internalization in tumor cell lines, immortalized endothelial cell lines or primary cells expressing CD98hc; in vitro transcytosis in capillary endothelial cells and cells lines; and permeability assay using Caco-2 and MDCK epithelial cell lines; in situ perfusion models and immunohistochemical or immunofluorescent staining of tissue sections; optical or PET animal imaging; standard PK and tissue distribution assays; and measuring one or more biological effects of a heterologous molecule (drug cargo or payload) in normal animals or disease animal models.

According to another embodiment, a CD98hc-specific binding moiety, conjugate or compound of the invention binds to human CD98hc in a standard ELISA or other similar assay with an EC50 of 300 nM or less, 100 nM or less, 10 nM or less, or 1 nM or less. Thus, a CD98hc selective binding compound of the invention binds to CD98hc, e.g., hCD98hc, in a standard ELISA or other similar assay with an EC50 in a range of 0.1 nM to 300 nM, 0.5 nM to 300 nM, 1 nM to 300 nM, 10 nM to 300 nM, 50 nM to 300 nM, 100 nM to 300 nM, 0.1 nM to 100 nM, 0.5 nM to 100 nM, 1 nM to 100 nM, 5 nM to 100 nM, 10 nM to 100 nM, 0.1 nM to 50 nM, 0.5 nM to 50 nM, 1 nM to 50 nM, 5 nM to 50 nM, 10 nM to 50 nM. It should be noted that strong selective binding may subsequently hinder transport across the membrane and/or release of the CD98hc-specific binding moiety and heterologous molecule(s) inside the CD98hc-positive cell. Hence, it should not be assumed that the tightest binding moieties are always ideal. One of skill in the art will be able to select an appropriate level of binding for desired transport and release of the therapeutic or diagnostic use envisioned. For example, in certain embodiments of the invention, the CD98hc-specific binding moiety binds to human CD98hc with an EC50 in a range of about 0.1 nM to about 10 µM, or in a preferred embodiment, in a range of about 1 nM to about 800 nM.

In certain embodiments, the CD98hc compound of the invention binds to hCD98hc with a 5-fold, 10-fold, 20-fold, 50-fold, 100-fold, 500-fold or more higher affinity compared to its binding affinity to a cross reactive ligand. In some embodiments, a CD98hc selective binding compound of the invention is specific to human CD98hc but also binds to or cross-reacts with one or more other mammalian CD98hcs.

Therapeutic versions of compounds with CD98hc-specific binding moieties of the invention include other molecular configurations, e.g., a VNAR monomer (i.e., a CD98hc-binding moiety) fused to stabilizing heterologous peptide regions, e.g., the Fc domain of an IgG or other immunoglobulin molecule, which may be expressed and then further purified as multimers, such as covalent dimers, allowing the activity of certain such therapeutic molecules to have even greater potency, preferably by at least 2-10 fold higher potencies and different binding affinities. Any of the antibody or antibody-like structures contemplated by the invention can be used as therapeutics.

When a polypeptide is produced in a recombinant cell other than one of human origin, it is typically free of polypeptides of human origin. In certain embodiments, it is advantageous to separate a polypeptide away from other recombinant cell components such as host cell polypeptides to obtain preparations that are of high purity or substantially homogeneous. As a first step, culture medium or cell lysates may be centrifuged to remove particulate cell debris and suitable protein purification procedures may be performed. Such procedures include, inter alia, fractionation (e.g., size separation by gel filtration or charge separation by ion-exchange column); ethanol precipitation; Protein A Sepharose® columns to remove contaminants such as IgG; hydrophobic interaction chromatography; reverse phase HPLC; chromatography on silica or on cation-exchange resins such as DEAE and the like; chromatofocusing; electrophoretic separations; ammonium sulfate precipitation; gel filtration using, for example, Sephadex beads such as G-75. Any number of biochemical purification techniques may be used to increase the purity of a CD98hc-specific binding moiety, conjugate or compound of the invention.

Pharmaceutically acceptable salts or solvates of any of the CD98hc-specific binding compounds of the invention are likewise within the scope of the present invention. As used herein, the term "pharmaceutically acceptable salt" refers to a salt that is not harmful to a patient or subject to which the salt in question is administered. It may be a salt chosen, e.g., among acid addition salts and basic salts. Examples of acid addition salts include chloride salts, citrate salts and acetate salts. Examples of basic salts include salts wherein the cation is selected from alkali metal cations, such as sodium or potassium ions, alkaline earth metal cations, such as calcium or magnesium ions, as well as substituted ammonium ions, such as ions of the type N(R1)(R2)(R3)(R4)+, wherein R1, R2, R3 and R4 independently will typically designate hydrogen, optionally substituted $C_{1-6}$-alkyl groups or optionally substituted $C_{2-6}$-alkenyl groups. Examples of relevant $C_{1-6}$-alkyl groups include methyl, ethyl, 1-propyl and 2-propyl groups. Examples of $C_{2-6}$-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977).

The term "solvate" in the context of the present invention refers to a complex of defined stoichiometry formed between a solute (in casu, a peptide compound or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

In each of the sequences described above, and in each sequence described herein, a C-terminal "—OH" moiety may be substituted for a C-terminal "—NH$_2$" moiety, and vice-versa.

Each of the specific compounds of the invention (e.g., CD98hc binding moieties, CD98hc antagonist peptides and compounds), and pharmaceutically acceptable salts and solvates thereof, constitutes an individual embodiment of the invention.

Derivatives, Variants, Conjugates

The invention further provides variants of a CD98hc-specific binding moiety of the invention, wherein the variant differs from the recited amino acid sequence by up to 1, 2, 3, 4, 5, 6, 7, 8, 9, 10 or more amino acid residues (but by no more than that which retains 85%, 90%, 95%, 99% or more amino acid sequence identity) and/or retains CD98hc bioactivity. CD98hc bioactivity can be measured, for example, by CD98hc binding affinity, using any of a number of assays know in the art. In certain embodiments, a compound of the invention binds to CD98hc with an affinity constant in a range of 0.1 nM to 500 nM, 0.5 nM to 500 nM, or 1 nM to 500 nM, 0.1 nM to 250 nM, 0.5 nM to 250 nM, or 1 nM to 250 nM as measured, e.g., by surface plasmon resonance such as in a BIACore assay. It will be understood by one of skill in the art that amino acid residues outside of the conserved FW, CDR1 and CDR3 motifs are in general regions in which amino acid modifications may be tolerated more readily without deleteriously depleting CD98hc binding activity. And it will also be understood by one of skill in the art that in certain embodiments, the binding affinity to CD98hc is less important than the ability of the binding moiety to transport a heterologous molecule across the membrane of a CD98hc-positive cell, and to release a molecular cargo or a so-called drug or molecular payload within the cell.

A biologically active fragment of any of the foregoing sequences which retains CD98hc bioactivity is also encompassed by the present invention. Thus, in further aspects, the invention further comprises compounds having an amino acid sequence that is truncated (shortened), from the N- or C-terminus, relative to the full-length sequence of compounds of the invention. In some embodiments, the truncated compounds are truncated by up to 1, 2, 3, 4, 5, 6, 7, 8, 9, 10, 11, 12, 13, 14, 15, 16, 17, 18, 19, 20, 21, 22, 23, 24, 25 or more amino acid residues, counting from the C-terminus of a compound of the invention as disclosed above. Amino acid residue outside of the conserved VNAR framework motifs are regions in which amino acid modifications may be better tolerated without deleteriously depleting CD98hc binding activity.

In some embodiments, the compounds of the invention may have at least 40%, e.g., at least 45%, 50%, 55%, 60%, 65%, 70%, 75%, 80%, 85%, 90%, 95%, 96%, 97%, 98%, or 99%, 99.5%, or 99.9% amino acid sequence identity to one of the CD98hc selective binding compounds disclosed herein, as long as the compound retains a CD98hc biological activity (as measured by CD98hc binding affinity, EC50 or IC50) within a range described herein.

Thus in certain embodiments, CD98hc specific binding compounds of the invention may comprise the amino acid sequence of any one of the compounds shown in Table 1 (see below), or a functional variant thereof that has at least about 70%, 75%, 80%, 85%, 90%, 95%, 97%, 98%, 99% or 99.5% sequence identity to any one of the compounds in Table 1. A functional variant of a polypeptide of the invention may inhibit at least one CD98hc bioactivity by any one of the assays disclosed herein by at least 50%, 55%, 60%, 65%, 70%, 75%, 80%, 85%, 90%, 95%, 97%, 98%, 99%, 99.5%, or 100%. In some embodiments, a CD98hc selective binding compound of the invention may comprise one or more amino acid substitutions, e.g., conservative amino acid substitutions, and retain CD98hc binding activity of at least 50%, 55%, 60%, 65%, 70%, 75%, 80%, 85%, 90%, 95%, 97%, 98%, 99%, 99.5%, or 100% compared to the binding by an unmodified CD98hc selective binding compound of the invention, and/or compared to binding of any other available anti-CD98hc antibody, such as anti-human CD98hc monoclonal antibody belimumab.

Throughout the present specification, unless naturally occurring amino acids are referred to by their full name (e.g. alanine, arginine, etc.), they are designated by their conventional three-letter or single-letter abbreviations (e.g. Ala or A for alanine, Arg or R for arginine, etc.). Unless otherwise indicated, reference is made to the L-isomeric forms of the amino acids in question. Where appropriate, the D-isomeric form of an amino acid is indicated in the conventional manner by the prefix "D" before the conventional three-letter code (e.g. DAsp, DPhe). Non-traditional amino acid residues and analogs are also included within the scope of the present invention (e.g., homoserine, norleucine, norvaline, ornithine and the like; and methods for making them are well known in the art.

In certain embodiments, the invention further provides a CD98hc specific binding moiety or CD98hc selective binding compound comprising said binding moiety, in which there are one or more conservative amino acid substitutions introduced into the polypeptide sequence. As used herein, the term "conservative substitution" denotes that one or more amino acids are replaced by another, biologically similar amino acid residue. Examples include substitution of amino acid residues with similar characteristics, e.g. small amino acids, acidic amino acids, polar amino acids, basic amino acids, hydrophobic amino acids and aromatic amino acids. See, for example, the table below. An example of a conservative substitution with a residue normally not found in endogenous, mammalian peptides and proteins is the conservative substitution of Arg or Lys with, for example, ornithine, canavanine, aminoethylcysteine or another basic amino acid. For further information concerning phenotypically silent substitutions in peptides and proteins, see, e.g., Bowie et al., Science 247, 1306-1310, 1990. In the scheme below are conservative substitutions of amino acids grouped by physicochemical properties. I: neutral, hydrophilic, II: acids and amides, III: basic, IV: hydrophobic, V: aromatic, bulky amino acids.

| I | II | III | IV | V |
| --- | --- | --- | --- | --- |
| A | N | H | M | F |
| S | D | R | L | Y |
| T | E | K | I | W |
| P | Q |   | V |   |
| G |   |   | C |   |

In some embodiments, a polypeptide of the invention may comprise functional fragments or variants of a CD98hc-specific binding moiety of the invention that have, at most, 20, 15, 10, 9, 8, 7, 6, 5, 4, 3, 2, or 1 amino acid substitutions compared to a polypeptide sequence recited herein, as long as it retains measurable biological activity alone or as a component of a CD98hc-selective binding compound. A polypeptide of the invention may further be with or without a signal sequence. In certain embodiments, the retained activity is at least 50% that of the CD98hc binding moiety of Table 1.

In some embodiments, a polypeptide of the invention shares at least 85%, 90%, 95%, 96%, 97%, 98%, 99% or more amino acid sequence identity to any one of the amino acid sequences of FW1, FW2-3, FW4, CDR1 or CDR3 of Table 1, as long as it retains measurable biological activity alone or as a component of a CD98hc selective binding compound. In certain embodiments, the retained activity is at least 50% that of a CD98hc binding moiety of Table 1.

CD98hc specific VNAR domains comprising compounds of the invention may optionally be conjugated (e.g., using linkers such as chemical linkers and/or linker peptides which are not usually associated with the domains being associated) to one or more additional agents which may include therapeutic and/or diagnostic agents. Such agents include but are not limited to chemotherapeutics such as cytostatic drugs, cytotoxins, radioisotopes, chelators, enzymes, nucleases, nucleic acids such as DNA, RNA or mixed nucleic acid oligonucleotides, including siRNAs, shRNAs, microRNAs, aptamers and the like; immunomodulators such as therapeutic antibodies, antibody and antibody-like fragments, inflammatory and anti-inflammatory cytokines, anti-inflammatory agents, radiotherapeutics, photoactive agents, diagnostic markers and the like. In certain embodiments, the pharmaceutically active moieties of the invention comprise at least one scFv molecule that is operably linked via a linker peptide to the C-terminus and/or N-terminus of an Fc region.

In certain embodiments, a compound of the invention comprising a CD98hc-specific binding moiety is multispecific, i.e., has at least one binding site that binds to a first molecule or epitope of a molecule (e.g., human CD98hc) and one or more other binding sites that bind to at least one heterologous molecule. Multispecific binding molecules of the invention may comprise at least two binding sites, three binding sites, four binding sites or more. In certain embodiments, at least two binding site of a multispecific binding molecule of the invention are capable of transporting a linked molecule across the BBB.

The invention thus further provides methods of making derivatives of CD98hc specific VNARs of the invention using biochemical engineering techniques well known to those of skill in the art. Such derivatives include, inter alia, multivalent or multispecific molecules comprising a CD98hc-specific binding moiety, including immunoconjugates. A large body of art is available relating to how to make and use antibody drug conjugates. Such knowledge and skill in the art may be adapted for use with the CD98hc specific binding moieties and CD98hc selective binding compounds of the invention. See, e.g., WO2007/140371; WO2006/068867. Methods relating to making and/or using different ligand conjugates may be applied. In certain embodiments, the CD98hc selective binding moieties and CD98hc selective binding compounds of the present invention include covalently modified and conjugated polypeptides forms of the polypeptides (e.g., immunoadhesins, radiolabeled or fluorescently labeled compounds, and the like). Methods for peptide conjugation and for labeling polypeptides and conjugating molecules are well known in the art.

Nucleic Acid Sequences that Encode a CD98hc Selective Binding Moiety or CD98hc Antagonist Compound In one aspect, the invention provides an isolated nucleic acid which encodes a CD98hc specific binding moiety or compound of the invention, or a fragment or derivative thereof. The nucleic acid may include, e.g., nucleic acid sequence encoding a polypeptide at least 50%, 55%, 60%, 65%, 70%, 75%, 80%, 85%, 90%, 95%, 99% or more, identical to a polypeptide comprising one of the amino acid sequences of Table 1. The invention also provides an isolated nucleic acid molecule comprising a sequence that hybridizes under stringent conditions to a nucleic acid sequence which encodes a CD98hc specific binding moiety or compound of the invention, or a fragment or derivative thereof, or the antisense or complement of any such sequence.

In another aspect, the invention provides an isolated nucleic acid molecule encoding a fusion protein comprising at least two segments, wherein one of the segments comprises a polypeptide or fragment thereof having CDR 1, CDR3 or framework amino acid sequences shown in Table 1, and variants thereof according to the invention. In certain embodiments, a second segment comprises a heterologous signal polypeptide, a heterologous binding moiety, an immunoglobulin fragment such as a Fc domain, or a detectable marker.

One aspect of the invention provides isolated nucleic acid molecules that encode CD98hc specific binding moiety proteins or biologically active portions thereof. Also included are nucleic acid fragments sufficient for use as hybridization probes to identify CD98hc binding moiety encoding nucleic acids and fragments for use as polymerase chain reaction (PCR) primers for the amplification or mutation of CD98hc specific binding moiety encoding nucleic acid molecules.

As used herein, the term "nucleic acid molecule" is intended to include DNA molecules, RNA molecules (e.g., mRNA, shRNA, siRNA, microRNA), analogs of the DNA or RNA generated using nucleotide analogs, and derivatives, fragments and homologs thereof. The nucleic acid molecules of the invention may be single-, double-, or triple-stranded. A nucleic acid molecule of the present invention, e.g., a nucleic acid molecule encoding any one of the amino acid sequences disclosed in Table 1, or a complement of any of these nucleotide sequences, may be isolated using sequence information provided herein and well known molecular biological techniques (e.g., as described in Sambrook et al., Eds., MOLECULAR CLONING: A LABORATORY MANUAL 2ND ED., Cold Spring Harbor Laboratory Press, Cold Spring Harbor, N.Y., 1989; and Ausubel, et al., Eds., CURRENT PROTOCOLS IN MOLECULAR BIOLOGY, John Wiley & Sons, New York, N.Y., 1993).

A nucleic acid molecule of the invention may be amplified using any form of nucleic acid template and appropriate oligonucleotide primers according to standard PCR amplification techniques. Amplified nucleic acid may be cloned into an appropriate vector and characterized, e.g., by restriction analysis or DNA sequencing. Furthermore, oligonucleotides corresponding to nucleotide sequences that encode a CD98hc selective binding moiety or compound of the invention may be prepared by standard synthetic techniques, e.g., using an automated DNA synthesizer.

The term "oligonucleotide" as used herein refers to a series of covalently linked nucleotide (or nucleoside residues, including ribonucleoside or deoxyribonucleoside residues) wherein the oligonucleotide has a sufficient number of nucleotide bases to be used in a PCR reaction. Oligonucleotides comprise portions of a nucleic acid sequence having at least about 10 nucleotides and as many as 50 nucleotides, preferably about 15 nucleotides to 30 nucleotides. Oligonucleotides may be chemically synthesized and may be used as probes. A short oligonucleotide sequence may be used to amplify, confirm, or reveal the presence of an identical, similar or complementary DNA or RNA in a particular cell or tissue.

Derivatives or analogs of the nucleic acid molecules (or proteins) of the invention include, inter alia, nucleic acid (or polypeptide) molecules having regions that are substantially homologous to the nucleic acid molecules or proteins of the invention, e.g., by at least about 45%, 50%, 70%, 80%, 95%, 98%, or even 99% identity (with a preferred identity of 80-99%) over a nucleic acid or amino acid sequence of the same size or when compared to an aligned sequence in which the alignment is done by a computer homology program known in the art. A percent identity for any candidate nucleic acid or polypeptide relative to a reference nucleic acid or polypeptide may be determined by aligning a reference sequence to one or more test sequences using, for example, the computer program ClustalW (version 1.83, default parameters), which enable nucleic acid or polypeptide sequence alignments across their entire lengths (global alignment) or across a specified length. The number of identical matches in such a ClustalW alignment is divided by the length of the reference sequence and multiplied by 100.

Also included are nucleic acid molecules capable of hybridizing to the complement of a sequence encoding the proteins of the invention under stringent or moderately stringent conditions. See e.g. Ausubel, et al., CURRENT PROTOCOLS IN MOLECULAR BIOLOGY, John Wiley & Sons, New York, N.Y., 1993, and below. An exemplary program is the GAP program (Wisconsin Sequence Analysis Package, Version 8 for UNIX, Genetics Computer Group, University Research Park, Madison, Wis.) using the default settings, which uses the algorithm of Smith and Waterman (1981) Adv. Appl. Math. 2:482489). Derivatives and analogs may be full length or other than full length, if the derivative or analog contains a modified nucleic acid or amino acid, as described below.

Stringent conditions are known to those skilled in the art and may be found in CURRENT PROTOCOLS IN MOLECULAR BIOLOGY, John Wiley & Sons, N.Y. (1989), 6.3.1-6.3.6. In certain embodiments, stringent conditions typically permit sequences at least about 65%, 70%, 75%, 85%, 90%, 95%, 98%, or 99% homologous to each other to remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. The term "stringent hybridization conditions" as used herein refers to conditions under which a nucleic acid probe, primer or oligonucleotide will hybridize to its target sequence, but only negligibly or not at all to other nucleic acid sequences. Stringent conditions are sequence- and length-dependent and depend on % (percent)-identity (or %-mismatch) over a certain length of nucleotide residues. Longer sequences hybridize specifically at higher temperatures than shorter sequences. Generally, stringent conditions are selected to be about 5° C. lower than the thermal melting point (Tm) for the specific sequence at a defined ionic strength and pH. Stringent conditions may also be achieved with the addition of destabilizing agents, such as formamide.

Methods of Producing CD98hc Specific VNAR Binding Moieties and Compounds Comprising them.

The compounds of the invention may be manufactured by standard synthetic methods, by use of recombinant expression systems, or by any other suitable method. Thus, the compounds may be synthesized in a number of ways, including, e.g., methods comprising: (1) synthesizing a polypeptide or polypeptide component of a CD98hc specific binding compound using standard solid-phase or liquid-phase methodology, either stepwise or by fragment assembly, and isolating and purifying the final peptide compound product; (2) expressing a nucleic acid construct that encodes a polypeptide or polypeptide component of a CD98hc specific binding compound in a host cell and recovering the expression product from the host cell or host cell culture; or (3) cell-free in vitro expression of a nucleic acid construct encoding a polypeptide or polypeptide component of a CD98hc specific binding compound, and recovering the expression product; or by any combination of the methods of (1), (2) or (3) to obtain fragments of the peptide component, subsequently joining (e.g., ligating) the fragments to obtain the peptide component, and recovering the peptide component.

It may be preferable to synthesize a polypeptide or polypeptide component of a CD98hc-specific binding compound of the invention by means of solid-phase or liquid-phase peptide synthesis. Compounds of the invention may suitably be manufactured by standard synthetic methods. Thus, peptides may be synthesized by, e.g., methods comprising synthesizing the peptide by standard solid-phase or liquid-phase methodology, either stepwise or by fragment assembly, and isolating and purifying the final peptide product. In this context, reference may be made to WO1998/11125 or, inter alia, Fields, G. B. et al., "Principles and Practice of Solid-Phase Peptide Synthesis"; in: Synthetic Peptides, Gregory A. Grant (ed.), Oxford University Press (2nd edition, 2002) and the synthesis examples herein.

Accordingly, the present invention also provides methods for producing a CD98hc specific binding compound of the invention according to above recited methods; a nucleic acid molecule encoding part or all of a polypeptide of the invention, a vector comprising at least one nucleic acid of the invention, expression vectors comprising at least one nucleic acid of the invention capable of producing a polypeptide of the invention when introduced into a host cell, and a host cell comprising a nucleic acid molecule, vector or expression vector of the invention.

CD98hc specific binding compounds of the invention may be prepared using recombinant techniques well known in the art. In general, methods for producing polypeptides by culturing host cells transformed or transfected with a vector comprising the encoding nucleic acid and recovering the polypeptide from cell culture are described in, e.g., Sambrook et al., Molecular Cloning: A Laboratory Manual (New York: Cold Spring Harbor Laboratory Press, 1989); Dieffenbach et al., PCR Primer: A Laboratory Manual (Cold Spring Harbor Laboratory Press, 1995).

A nucleic acid encoding a desired polypeptide may be inserted into a replication vector for further cloning (amplification) of the DNA or for expression of the nucleic acid into RNA and protein. A multitude of cloning and expression vectors are publicly available. Expression vectors capable of directing transient or stable expression of genes to which they are operably linked are well known in the art. The vector components generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

Any suitable host cell may be used to produce CD98hc specific binding compounds of the invention. Host cells may be cells stably or transiently transfected, transformed, transduced or infected with one or more expression vectors which drive expression of a polypeptide of the invention. Suitable host cells for cloning or expressing nucleic acids of the invention include prokaryote, yeast, or higher eukaryote cells. Eukaryotic microbes such as filamentous fungi yeast, *Arabidopsis*, and other plant and animal eukaryotic host cells that may be grown in liquid culture are suitable cloning or expression hosts for vectors. Suitable host cells for the expression of glycosylated polypeptides may also be derived from multicellular organisms.

Creation and isolation of host cell lines producing a CD98hc-specific binding moiety, conjugate or compound of the invention can be accomplished using standard techniques known in the art. Mammalian cells are preferred host cells for expression of peptides. Particularly useful mammalian cells include, inter alia, HEK 293, NSO, DG-44, and CHO cells, but any other suitable host cell may be used according to the invention. Preferably, the CD98hc-specific moieties, conjugates or compounds are secreted into the medium in which the host cells are cultured, from which the CD98hc-specific binding moieties, conjugates or compounds may be recovered or purified.

When a polypeptide is produced in a recombinant cell other than one of human origin, it is typically free of polypeptides of human origin. In certain embodiments, it is advantageous to separate a polypeptide away from other recombinant cell components such as host cell polypeptides to obtain preparations that are of high purity or substantially homogeneous. As a first step, culture medium or cell lysates may be centrifuged to remove particulate cell debris and suitable protein purification procedures may be performed. Such procedures include, inter alia, fractionation (e.g., size separation by gel filtration or charge separation by ion-exchange column); ethanol precipitation; Protein A Sepharose columns to remove contaminants such as IgG; hydrophobic interaction chromatography; reverse phase HPLC; chromatography on silica or on cation-exchange resins such as DEAE and the like; chromatofocusing; electrophoretic separations; ammonium sulfate precipitation; gel filtration using, for example, Sephadex beads such as G-75. Any number of biochemical purification techniques may be used to increase the purity of a CD98hc-specific binding moiety, conjugate or compound of the invention.

Methods of Detection

In certain embodiments, the CD98hc specific binding compounds of the invention may be used to detect and quantify levels of CD98hc, or cells that express CD98hc. This can be achieved, for example, by contacting a test sample (such as an in vitro sample) and a control sample with a CD98hc specific binding moiety of the invention, or a compound comprising it, under conditions which permit formation of a complex between the compound and CD98hc, or between CD98hc and an anti-CD98hc antibody, or both. Any bound CD98hc complexes are detected and/or quantified in CD98hc specific VNAR containing samples and control samples.

Accordingly, the invention further provides methods for detecting the presence of CD98hc or CD98hc antibodies in a sample, or measuring the amount of either of the foregoing, comprising contacting the sample, and preferably a control sample, with a CD98hc-binding compound of the invention under conditions that permit complex formation between the CD98hc binding moiety of the compound and CD98hc, e.g., human CD98hc. Formation or inhibition of formation of a CD98hc-binding compound/CD98hc complex is then detected and/or quantified. A variety of tests can be designed based on features of binding or competition for binding. For example, the presence of CD98hc in a test sample may be detected directly, or may be detected and quantified based on the ability to compete for binding of CD98hc by a CD98hc-binding moiety, conjugate or compound. In general, the difference in complex formation between a test sample and a control sample is indicative of a binding interaction.

Methods of Treatment Using CD98hc Binding Moieties and Compositions

The present invention provides a CD98hc binding moiety or CD98hc specific binding compound for use, alone or in combination with one or more additional therapeutic agents in a pharmaceutical composition, for treatment or prophylaxis of conditions, diseases and disorders responsive to modulation (such as inhibiting or blocking) of the interaction between CD98hc and its in vivo ligands.

In certain embodiments, a CD98hc specific binding moiety or a conjugate or drug delivery vehicle comprising such a binding moiety is administered in combination with at least one additional agent that mediates blood-brain barrier transport, such as an agent comprising a receptor binding domain of an apolipoprotein such as a receptor binding domain of ApoA, ApoB, ApoC, ApoD, ApoE, ApoE2, ApoE3 or ApoE4, and any combination thereof. Any one of a number of other molecules which mediate transport of heterologous molecules across the blood brain barrier may be used in combination with the CD98hc specific binding moiety comprising agents of the invention, including, e.g., IgG, YY (PYY), neuropeptide Y (NPY), corticotropin releasing factor (CRF), and urocortin. Certain viral glycoproteins (e.g., rabies virus glycoprotein (RVG) peptide) and antibodies and antibody fragments may also be used in this regard.

Combination therapies may include co-administration of agents or alternate administrations which result in a combination therapy within the patient based on duration of the therapeutic agent(s) or their biological effects in the patient.

In certain embodiments, a therapeutic agent transported across the BBB in association with a CD98hc-specific binding moiety of the invention is effective in treating a brain or CNS disease, condition, injury or disorder, such as, for example, neurodegenerative diseases, neuronal injury, inflammation or damage, and brain cancers, spinal cord injury (SCI) and traumatic brain injury (TBI). In certain embodiments, a brain disorder is selected from epilepsy, meningitis, encephalitis including HIV Encephalitis, progressive multifocal leukoencephalopathy, neuromyelitis optica, multiple sclerosis, late-stage neurological trypanosomiasis, amyotrophic lateral sclerosis (ALS), progressive bulbar palsy (PBP), primary lateral sclerosis (PLS), progressive muscular atrophy (PMA), Alzheimer's disease, Parkinson's disease, Huntington's disease, De Vivo disease, and any type of tumor, cancer or hyperproliferative disease in the brain or CNS.

In certain embodiments, a therapeutic agent transported across a hCD98hc-containing membrane in association with a CD98hc-specific binding moiety of the invention is effective in treating a condition, disease or disorder associated with the GI tract or one which will otherwise benefit from drug delivery across an epithelial membrane of the gut mediated by hCD98hc transport.

The invention in certain embodiments provides methods of treatment or prevention of a CD98hc associated disorder, the method comprising the step of administering to a subject (e.g., a patient) in need thereof a therapeutically effective amount of the CD98hc specific binding compound or pharmaceutical composition comprising a CD98hc binding compound of the invention, as described herein. As used herein, an "effective amount," a "therapeutically effective amount" or an "effective dose" is an amount of a composition (e.g., a therapeutic composition or agent) that produces at least one desired therapeutic effect in a subject, such as preventing or treating a target condition or beneficially alleviating a symptom associated with the condition.

The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. See, e.g., Remington: The Science and Practice of Pharmacy 21st Ed., Univ. of Sciences in Philadelphia (USIP), Lippincott Williams & Wilkins, Philadelphia, PA, 2005.

Additionally, for some embodiments specificity for CD98hc is an important feature for a BBB carrier because off target binding could have undesirable safety and/or PK consequences.

Pharmaceutical Compositions

The present invention further provides pharmaceutical compositions comprising a CD98hc-specific binding moiety of the invention or compound, or a pharmaceutically acceptable salt or solvate thereof, according to the invention, together with a pharmaceutically acceptable carrier, excipient or vehicle.

Accordingly, the present invention further provides a pharmaceutical composition comprising a CD98hc-specific binding moiety of the invention or compound comprising a CD98hc-specific binding moiety, as well as variant and derivative compounds comprising a CD98hc-specific binding moiety of the invention. Certain embodiments of the pharmaceutical compositions of the invention are described in further detail below.

The present invention also provides pharmaceutical compositions comprising a CD98hc-specific binding moiety or a CD98hc-specific binding compound for use in treating, ameliorating or preventing one or more diseases, conditions, disorders or symptoms relating to B cells and immunoglobulin production, as described in further detail below. Each such disease, condition, disorder or symptom is envisioned to be a separate embodiment with respect to uses of a pharmaceutical composition according to the invention.

Formulations, Administration and Dosing

CD98hc specific binding compounds of the present invention, or salts thereof, may be formulated as pharmaceutical compositions prepared for storage or administration, which typically comprise a therapeutically effective amount of a compound of the invention, or a salt thereof, in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person. The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl) aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. The term further encompasses any agents listed in the US Pharmacopeia for use in animals, including humans.

The term "pharmaceutically acceptable salt" refers to the salt of the compounds. Salts include pharmaceutically acceptable salts such as acid addition salts and basic salts. Examples of acid addition salts include hydrochloride salts, citrate salts and acetate salts. Examples of basic salts include salts where the cation is selected from alkali metals, such as sodium and potassium, alkaline earth metals such as calcium, and ammonium ions $^+N(R^3)_3(R^4)$, where $R^3$ and $R^4$ independently designate optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, Pa., U.S.A., 1985 and more recent editions, and in the Encyclopaedia of Pharmaceutical Technology.

"Treatment" is an approach for obtaining beneficial or desired clinical results. For the purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms when compared to the absence of treatment and is not necessarily meant to imply complete cessation of the relevant condition.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration.

Pharmaceutically acceptable carriers or diluents include those used in formulations suitable for oral, rectal, nasal or parenteral (including subcutaneous, intramuscular, intravenous, intradermal, and transdermal) administration. The formulations may conveniently be presented in unit dosage form and may be prepared by any of the methods well known in the art of pharmacy. Subcutaneous or transdermal modes of administration may be particularly suitable for the compounds described herein.

An acceptable route of administration may refer to any administration pathway known in the art, including but not limited to aerosol, enteral, nasal, ophthalmic, oral, parenteral, rectal, vaginal, or transdermal (e.g., topical administration of a cream, gel or ointment, or by means of a transdermal patch). "Parenteral administration" is typically associated with injection at or in communication with the intended site of action, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

In another aspect, the present invention provides a composition, e.g., a pharmaceutical composition, comprising one or a combination of different CD98hc specific binding compounds of the invention, or a VNAR sequence containing, CD98hc specific binding region thereof, or an ester, salt or amide of any of the foregoing, and at least one pharmaceutically acceptable carrier. Such compositions may include one or more different BAFF specific binding moieties or compounds in combination to produce an immunoconjugate or multi-specific molecule comprising at least one CD98hc specific binding moiety. For example, a pharmaceutical composition of the invention may comprise a combination of CD98hc specific binding moieties which bind to different epitopes of CD98hc or which otherwise have complementary biological activities.

Pharmaceutical compositions of the invention may be administered alone or in combination with one or more other therapeutic or diagnostic agents. A combination therapy may include a CD98hc specific binding compound of the present invention combined with at least one other therapeutic agent selected based on the particular patient, disease or condition to be treated. Examples of other such agents include, inter alia, a cytotoxic, anti-cancer or chemotherapeutic agent, an anti-inflammatory or anti-proliferative agent, an antimicrobial or antiviral agent, growth factors, cytokines, an analgesic, a therapeutically active small molecule or polypeptide, a single chain antibody, a classical antibody or fragment thereof, or a nucleic acid molecule which modulates one or more signaling pathways, and similar modulating therapeutics which may complement or otherwise be beneficial in a therapeutic or prophylactic treatment regimen.

As used herein, "pharmaceutically acceptable carrier" includes any and all physiologically acceptable, i.e., compatible, solvents, dispersion media, coatings, antimicrobial agents, isotonic and absorption delaying agents, and the like. In certain embodiments, the carrier is suitable for intravenous, intramuscular, subcutaneous, parenteral, spinal or epidermal administration (e.g., by injection or infusion). Depending on selected route of administration, the CD98hc specific binding moiety comprising compound or component may be coated in a material or materials intended to protect the compound from the action of acids and other natural inactivating conditions to which the active CD98hc binding moiety may encounter when administered to a subject by a particular route of administration.

As above, a compound of the invention may encompass one or more pharmaceutically acceptable salts. As used herein a "pharmaceutically acceptable salt" retains qualitatively a desired biological activity of the parent compound without imparting any undesired effects relative to the compound. Examples of pharmaceutically acceptable salts include acid addition salts and base addition salts. Acid addition salts include salts derived from nontoxic inorganic acids, such as hydrochloric, nitric, phosphorous, phosphoric, sulfuric, hydrobromic, hydroiodic and the like, or from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include salts derived from alkaline earth metals, such as sodium, potassium, magnesium, calcium and the like, as well as from nontoxic organic amines, such as N, N'-dibenzylethylenediamine, N-methylglucamine, chloroprocaine, choline, diethanolamine, ethylenediamine, procaine and the like.

A pharmaceutical composition of the invention also optionally includes a pharmaceutically acceptable antioxidant. Exemplary pharmaceutically acceptable antioxidants are water soluble antioxidants such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propylgallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of the required particle size in the case of dispersions, and by the use of surfactants.

CD98hc selective binding moieties and compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. Isotonic agents, such as sugars, sodium chloride, and the like into the compositions, may also be desirable. In addition, prolonged absorption of the injectable pharmaceutical form may be brought about by the inclusion of agents which delay absorption such as, aluminum monostearate and gelatin.

Exemplary pharmaceutically acceptable carriers include sterile aqueous solutions or dispersions and sterile powders for the extemporaneous preparation of sterile injectable solutions or dispersion. Such media and reagents for pharmaceutically active substances are known in the art. The pharmaceutical compositions of the invention may include any conventional media or agent unless any is incompatible with the active CD98hc specific binding compound. Supplementary active compounds may further be incorporated into the compositions.

Therapeutic compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g., glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g., sugars, polyalcohols such as mannitol, sorbitol, or sodium chloride may be desirable in the composition. Prolonged absorption of injectable compositions may be brought about by including in the composition an agent that delays absorption for example, monostearate salts and gelatin.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a CD98hc specific binding moiety (or a CD98hc binding compound comprising such a moiety) in the required amount in an appropriate solvent with one or a combination of ingredients described above, as required, followed by sterilization microfiltration. Dispersions may be prepared by incorporating the active compound into a sterile vehicle that contains a dispersion medium and other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a CD98hc selective binding moiety or composition of the invention is administered by, e.g., intravenous, cutaneous or subcutaneous injection, the binding agent will be in the form of a pyrogen-free, parenterally acceptable aqueous solution. Methods for preparing parenterally acceptable protein solutions, taking into consideration appropriate pH, isotonicity, stability, and the like, are within the skill in the art. A preferred pharmaceutical composition for intravenous, cutaneous, or subcutaneous injection will contain, in addition to binding agents, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

The amount of active ingredient which can be combined with a carrier material to produce a single dosage form will vary depending on a variety of factors, including the subject being treated, and the particular mode of administration. In general, it will be an amount of the composition that produces an appropriate therapeutic effect under the particular circumstances. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens may be adjusted to provide the optimum desired response (e.g., a therapeutic response). For example, a single bolus may be administered, several divided doses may be administered over time, or the dose may be proportionally reduced or increased as indicated by the particular circumstances of the therapeutic situation, on a case by case basis. It is especially advantageous to formulate parenteral compositions in dosage unit forms for ease of administration and uniformity of dosage when administered to the subject or patient. As used herein, a dosage unit form refers to physically discrete units suitable as unitary dosages for the subjects to be treated; each unit containing a predetermined quantity of active compound calculated to produce a desired therapeutic effect in association with the required pharmaceutical carrier. The specification for the dosage unit forms of the invention depend on the specific characteristics of the active compound and the particular therapeutic effect(s) to be achieved, taking into consideration and the treatment and sensitivity of any individual patient.

For administration of a CD98hc selective binding moiety or compound, the dosage range will generally be from about 0.0001 to 100 mg/kg, and more usually 0.01 to 5 mg/kg, of the host body weight. Exemplary dosages may be 0.25 mg/kg body weight, 1 mg/kg body weight, 3 mg/kg body weight, 5 mg/kg body weight or 10 mg/kg body weight or within the range of 1-10 mg/kg. An exemplary treatment regime is a once or twice daily administration, or a once or twice weekly administration, once every two weeks, once every three weeks, once every four weeks, once a month, once every two or three months or once every three to 6 months. Dosages may be selected and readjusted by the skilled health care professional as required to maximize therapeutic benefit for a particular subject, e.g., patient. CD98hc specific binding compounds will typically be administered on multiple occasions. Intervals between single dosages can be, for example, 2-5 days, weekly, monthly, every two or three months, every six months, or yearly. Intervals between administrations can also be irregular, based on regulating blood levels of CD98hc specific binding compound to the target CD98hc ligand in the subject or patient. In some methods, dosage is adjusted to achieve a plasma antagonist concentration of about 1-1000 μg/ml and in some methods about 25-300 μg/ml. Dosage regimens for a CD98hc specific binding compound of the invention include intravenous administration of 1 mg/kg body weight or 3 mg/kg body weight with the compound administered every two to four weeks for six dosages, then every three months at 3 mg/kg body weight or 1 mg/kg body weight.

In certain embodiments, two or more CD98hc specific binding compounds with different binding properties may be administered simultaneously or sequentially, in which case the dosage of each administered compound may be adjusted to fall within the ranges described herein.

In certain embodiments, a CD98hc specific binding compound of the invention may be administered as a sustained release formulation, in which case less frequent administration is required. Dosage and frequency vary depending on the half-life of the CD98hc specific binding compound in the subject or patient. The dosage and frequency of administration may vary depending on whether the treatment is therapeutic or prophylactic (e.g., preventative), and may be adjusted during the course of treatment. In certain prophylactic applications, a relatively low dosage is administered at relatively infrequent intervals over a relatively long period of time. Some subjects may continue to receive treatment over their lifetime. In certain therapeutic applications, a relatively high dosage at relatively short intervals is sometimes required until progression of the disease is reduced or until the patient shows partial or complete amelioration of symptoms of disease. Thereafter, the patient may be switched to a suitable prophylactic dosing regimen.

Actual dosage levels of the CD98hc specific binding compound alone or in combination with one or more other active ingredients in the pharmaceutical compositions of the present invention may be varied so as to obtain an amount of the active ingredient which is effective to achieve the desired therapeutic response for a particular patient, composition, and mode of administration, without causing deleterious side effects to the subject or patient. A selected dosage level will depend upon a variety of factors, such as pharmacokinetic factors, including the activity of the particular CD98hc specific binding compound or composition employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject or patient being treated, and similar factors well known in the medical arts.

Administration of a "therapeutically effective dosage" of a CD98hc-binding compound of the invention may result in a decrease in severity of disease symptoms, an increase in frequency and duration of disease symptom-free periods, or a prevention of impairment or disability due to the disease affliction.

A CD98hc specific binding compound or composition of the present invention may be administered via one or more routes of administration, using one or more of a variety of methods known in the art. As will be appreciated by the skilled worker, the route and/or mode of administration will vary depending upon the desired results. Routes of administration for CD98hc specific binding compounds or compositions of the invention include, e.g., intravenous, intramuscular, intradermal, intraperitoneal, subcutaneous, spinal or other parenteral routes of administration, for example by injection or infusion. The phrase "parenteral administration" as used herein refers to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

In other embodiments, a CD98hc specific binding compound or composition of the invention may be administered by a non-parenteral route, such as a topical, epidermal or mucosal route of administration, for example, intranasally, orally, vaginally, rectally, sublingually or topically.

As described elsewhere herein, an active CD98hc specific binding compound may be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compounds or compositions of the invention may be administered with one or more of a variety of medical devices known in the art. For example, in one embodiment, a therapeutic CD98hc specific binding composition of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

In certain embodiments, the CD98hc specific binding compound or composition of the invention may be formulated to ensure a desired distribution in vivo. For example, the blood-brain barrier (BBB) excludes many highly hydrophilic compounds. To target a therapeutic compound or composition of the invention to a particular in vivo location, they can be formulated, for example, in liposomes which may comprise one or more moieties that are selectively transported into specific cells or organs, thus enhancing targeted drug delivery. Exemplary targeting moieties include folate or biotin; mannosides; antibodies; surfactant protein A receptor; p120 and the like.

Kits for Detecting or Quantifying CD98hc in a Sample

Also, within the scope of the invention are kits comprising at least one CD98hc specific binding moiety or CD98hc specific binding compound or composition of the invention, and optionally, instructions for use. Kits may be useful for quantifying CD98hc or CD98hc specific antibodies in a sample, or may be useful for detection of CD98hc, such as in diagnostics methods. The kit may further or alternatively comprise at least one nucleic acid encoding a CD98hc specific binding moiety of the invention. A kit of the invention may optionally comprise at least one additional reagent (e.g., standards, markers and the like). Kits typically include a label indicating the intended use of the contents of the kit. The kit may further comprise reagents and other tools for measuring CD98hc in a sample or in a subject, or for diagnosing whether a patient belongs to a group that responds to a CD98hc-specific binding compound which makes use of a compound, composition or related method of the invention as described herein.

Delivery Devices and Further Kits

In certain embodiments, the invention relates to a device comprising one or more CD98hc specific binding compounds of the invention, or pharmaceutically acceptable salts or solvates thereof, for delivery to a subject. Thus, one or more compounds of the invention or pharmaceutically acceptable salts or solvates thereof can be administered to a patient in accordance with the present invention via a variety of delivery methods, including: intravenous, subcutaneous, intramuscular or intraperitoneal injection; oral administration; transdermal administration; pulmonary or transmucosal administration; administration by implant, osmotic pump, cartridge or micro pump; or by other means recognized by a person of skill in the art.

In some embodiments, the invention relates to a kit comprising one or more peptides, or pharmaceutically acceptable salts or solvates thereof, of the invention. In other embodiments, the kit comprises one or more pharmaceutical compositions comprising one or more peptides or pharmaceutically acceptable salts or solvates thereof. In certain embodiments, the kit further comprises packaging and/or instructions for use.

While some embodiments of the invention have been described by way of illustration, it will be apparent that the invention can be put into practice with many modifications, variations and adaptations, and with the use of numerous equivalents or alternative solutions that are within the scope of persons skilled in the art, without departing from the spirit of the invention or exceeding the scope of the claims.

All publications, patents, and patent applications are herein incorporated by reference in their entirety to the same extent as if each individual publication, patent or patent application was specifically and individually indicated to be incorporated by reference in its entirety.

EXAMPLES

The examples presented herein represent certain embodiments of the present invention. However, it is to be understood that these examples are for illustration purposes only and do not intend, nor should any be construed, to be wholly definitive as to conditions and scope of this invention. The examples were carried out using standard techniques, which are well known and routine to those of skill in the art, except where otherwise described in detail.

Example 1. Design and Generation of a VNAR Type IV Semi-Synthetic Library

To prepare a Type IV VNAR phage display library, the scaffold shown in FIG. 1A was chosen based on its favorable properties, including high monomer expression and secretion, high monomer stability (>3 months +4° C.) and low number of post translational modification sites. The library was constructed by randomizing four amino acid residues in the CDR1 and 13 amino acid residues in CDR3 using focused NNK codon mutagenesis for the residues marked as X (FIG. 1B). The library size was estimated at $10^8$-$10^9$ unique clones with 70% of sequences in frame and >70% of clones displaying at >15% of phage PIII protein as determined by ELISA or Western blot.

When mixed with Type I and Type II libraries, this Type IV library returned a high proportion of hits when selected on CD98 and the most brain penetrant VNAR F12 was derived from the Type IV library (discussed in the Examples below).

This Type IV scaffold was also engineered into a vector with a modular structure to allow for modifications to each variable site (CDR1, CDR3, HV2 and HV4) (see, FIG. 2).

Example 2. Selection of CD98hc-Binding VNARs

Four different semi-synthetic VNAR phage libraries (separate type I, type II, and type IV isoforms) were used to select clones that bind to CD98hc (SLC3A2) using the wobbegong shark library OSX-2 (complexity~$6.8\times10^9$ CFU) described in the Intl. Pub. No. WO2016/077840, a Type II library, the Type II OSX-3 library and the Type I OSX-4 synthetic library (described in the Intl. Pub. No. WO2015/200883), and the Type IV library described in Example 1. The phagemid vector used for both phage display and monomeric VNAR expression is pOsD2, a modified version of pSEX81 (Progen) in which a 6×His tag, a FLAG tag, and an amber stop codon were inserted between the VNAR (inserted into SfiI sites) and the full-length PIII protein of the M13 phage (WO2015/200883). The 6×His tag does not normally form part of a VNAR but can optionally be retained.

Phage library panning was performed essentially as described in (Griffiths et al. 1994, EMBO J., 13:3245-3260). Three rounds of panning were performed on polyhistidine-tagged ectodomain of human CD98hc using Ni-NTA-Dynabeads® magnetic beads to pull down binders.

Individual phage clones from round 2 and 3, were tested for their binding to both human and mouse CD98hc in phage ELISA. Briefly, $1\times10^{12}$ phage were incubated in Nunc® Maxisorp® 96-well plates coated at 1 μg/mL with the ectodomain of human or murine CD98hc or HSA (Sigma) as a negative control. After incubating at room temperature for one hour, the unbound particles were removed by washing the wells three times in PBS-0.1% Tween-20. Bound bacteriophage were detected using a specific anti-M13 antibody (GE).

TABLE 1A

Mouse and Human Cross Reactive VNARs

| Clone ID | SEQ. ID NO | Amino Acid Sequence |
|---|---|---|
| F1 | 7 | ARVDQTPQTITKEEGESLTI NCVLRVHGRALASTSWYRKK SGSTREETISKGGRYVETVN SGSKSFSLRINDLTVEDSGT YRCNVYGLSSGDIEGVKKID VYGDGTAVTVNA |
| D1 | 8 | ARVDQTPQTITKEEGESLTI NCVLRHNYSALASTSWYRKK SGSTREETISKGGRYVETVN SGSKSFSLRINDLTVEDSGT YRCNVYGISFIEEKIRYDFD VYGDGTAVTVNA |
| G12 | 9 | ARVDQTPQTITKETGESLTI NCVLRDSNCALSSTYWYRKK SGSTNEALISKGGRYVETV NSGSKSFSLRINDLTVEDSG TYRCNVVQDLRDDCFFRDV YGGGTAVTVNA |
| H6 | 10 | ARVDQTPQTITKEEGESLTI NCVLRTHSNALASTSWYRKK SGSTREETISKGGRYVETVN SGSKSFSLRINDLTVEDSGT YRCNVYAFLEIQPNIYHEFD VYGDGTAVTVNA |
| H7 | 11 | ARVDQTPQTITKEEGESLTI NCVLRYNNPALASTSWYRKK SGSTREETISKGGRYVETVN SGSKSFSLRINDLTVEDSGT YRCNVYFFPSFLVDKLQSHD VYGDGTAVTVNA |
| G3 | 12 | ARVDQTPQTITKETGESLTI NCVLRDNNCALSTTYWYRKK SGSTNEENISKGGRYVETVN SGSKSFSLRINDLTVEDSGT YRCKVHFFPSFCNSTSIRSV DVYGGGTWTVNA |
| E12 | 13 | ARVDQTPQTITKEEGESLTI NCVLRTQDPALASTSWYRKK SGSTREETISKGGRYVETVN SGSKSFSLRINDLTVEDSGT YRCNVYFLLAPTKTKLQGID VYGDGTAVTVNA |

TABLE 1A-continued

Mouse and Human Cross Reactive VNARs

| Clone ID | SEQ. ID NO | Amino Acid Sequence |
|---|---|---|
| B12 | 14 | ARVDQTPRSVTKETGESLTINCVLRDASYALGSTCWYRKKSGSTNEESISKGGRYVETVNSGSKSFSLRINDLTVEDGGTYRCGVARGWRTLNYLCDVRTGEWSCVWRAAACGDGTAVTVNA |
| E12A | 15 | ARVDQTPQTIAREEGESVTINCWRdsNRALASTSWCSEKYVSTREESISKGGRYVETVNSGSKSFSLRINDLTVEDSGTYRCNVYFFPSFEVDVLQTNDVYGDGTAVTVNA |
| F11 | 16 | ARVDQTPQTITKEEGESLTINCVLRGEFYALASTSWYRKKSGSTREETISKGGRYVETVNSGSKSFSLRINDLTVEDSGTYRCNVYGYRIFSPEVKGPNDVYGDGTAVTVNA |
| A8 | 17 | ARVDQTPQTITKEEGESLTINCVLRRNFQLASTSWYRKKSGSTREETISKGGRYVETVNSGSKSFSLRINDLTVEDSGTYRCNVYGFVEFAKNIVEFIDVYGDGTAVTVNA |
| G6 | 18 | ARVDQTPQTITKEEGESLTINCVLRVETRALASTSWYRKKSGSTREETISKGGRYVETVNSGSKSFSLRINDLTVEDSGTYRCNVYIRHYSEFTQAPFRDVYGDGTAVTVNA |
| H12 | 19 | ARVDQTPQTITKEEGESLTINCVLRVHGCALASTSWYRKKSGSTREETISKGGRYVETVNSGSKSFSLRINDLTVEDSGTYRCNVYGLSFVDIEGVKKIDVYGDGTAVTVNA |
| F12 | 20 | ARVDQTPQTITKEEGESLTINCVLRVHGRALASTSWYRKKSGSTREETISKGGRYVETVNSGSKSFSLRINDLTVEDSGTYRCNVYGLSFGDIEGVKKIDVYGDGTAVTVNA |
| H7A | 21 | PGVDQTPEQTIKKEEGESVTIKCVMRVKYPALASTSRYRKKSGSREETISKGGRYVETVNYSSKSISVRINDMTVEDSGRYRCNVYEEYAVDCDALVYQDVYGDGTAVTVNA |
| H8 | 22 | ARVDQTPQTITKETGESLTINCVLRDSNCALPSTYWYRKKSGSTNEESISKGGRYVETVNSGSKSFSLRINDLWEDSGTYRCKVGNYCIRLCYDMKFAVDVYGGGTAVTVNA |
| C6 | 23 | ARVDQTPQTITKETGESLTINCVLRDSNCALSSTYWYRKKSGSTNEALISKGGRYVETVNSGSKSFSLRINDLTVEDSGTYRCNVVYDLRDDCFFRDVYGGGTAVTVNA |
| G10 | 24 | ARVDQTPQTITKETGESLTINCVLRDSNCALSSTYWYRKKSGSTNEENISKGGRYVETVNSGSKSFSLKINDLTVEDSGTYRCKVVFKLFSGRACAGEKDVYGGGTVVTVNA |

TABLE 1B

CDR and HV Regions of Cross Reactive VNARs

| Clone ID | CDR1 | SEQ. ID NO | HV2 | HV4 | CDR3 | SEQ. ID NO | Iso-Type |
|---|---|---|---|---|---|---|---|
| F1 | VHGRALA | 25 | TREETISKG | NSGSKS | VYGLSSGDIEGVKKIDV | 79 | 4 |
| D1 | HNYSALA | 26 | TREETISKG | NSGSKS | VYGISFIEEKIRYDFDV | 80 | 4 |
| G12 | DSNCALS | 27 | TNEALISKG | NSGSKS | VVQDLRDDCFFRDV | 81 | 2 |
| H6 | THSNALA | 28 | TREETISKG | NSGSKS | VYAFLEIQPNIYHEFDV | 82 | 4 |
| H7 | YNNPALA | 29 | TREETISKG | NSGSKS | VYFFPSFLVDKLQSHDV | 83 | 4 |
| G3 | DNNCALS | 30 | TNEENISKG | NSGSKS | VHFFPSFCNSTSIRSVDV | 84 | 2 |
| E12 | TQDPALA | 31 | TREETISKG | NSGSKS | VYFLLAPTKTKLQGIDV | 85 | 4 |
| B12 | DASYALG | 32 | TNEESISKG | NSGSKS | VARGWRTLNYLCDVRTGEWSCV | 86 | 1 |
| E12A | DSNRALA | 33 | TREETISKG | NSGSKS | VYFFPSFEVDVLQTNDV | 87 | 4 |
| F11 | GEFYALA | 34 | TREETISKG | NSGSKS | VYGYRIFSPEVKGPNDV | 88 | 4 |
| A8 | RNFQLA | 35 | TREETISKG | NSGSKS | VYGFVEFAKNIVEFIDV | 89 | 4 |
| G6 | VETRALA | 36 | TREETISKG | NSGSKS | VYIRHYSEFTQAPFRDV | 90 | 4 |

TABLE 1B-continued

CDR and HV Regions of Cross Reactive VNARs

| Clone ID | CDR1 | SEQ. ID NO | HV2 | HV4 | CDR3 | SEQ. ID NO | Iso-Type |
|---|---|---|---|---|---|---|---|
| H12 | VHGCALA | 37 | TREETISKG | NSGSKS | VYGLS FVDIE GVKKI DV | 91 | 4 |
| F12 | VHGRALA | 38 | TREETISKG | NSGSKS | VYGLS FGDIE GVKKI DV | 92 | 4 |
| H7A | VKYPALA | 39 | SREETISKG | NYSSKS | VYEEY AVDCD ALVYQ DV | 93 | 4 |
| H8 | DSNCALP | 40 | TNEESISKG | NSGSKS | VGNYC IRLCY DMKFA VDV | 94 | 2 |
| C6 | DSNCALS | 41 | TNEALISKG | NSGSKS | VVYDL RDDCF FRDV | 95 | 2 |
| G10 | DSNCALS | 42 | TNEENISKG | NSGSKS | VVFKL FSGRA CAGEK DV | 96 | 2 |

Example 3. Preparation of Fc Fusions

The eighteen VNARs binding to mouse and human CD98hc were expressed as N-terminal fusions with human IgG1 Fc in mammalian cells and re-tested for their binding activity in ELISA. The clones were reformatted as bivalent VNAR-Fc by cloning the VNARs into the commercial pFUSE vector (pFUSE-hIgG1e3-Fc2). The Fc region of the protein contained CH2 and CH3 domains with the hinge that served as a flexible spacer between the two parts of the Fc-fusion protein. N-termini of the construct contained the IL2 signal sequence to allow secretion. A HEK Expi293 expression system was used to transiently express the proteins. The VNAR clones were expressed as Fc formats in mammalian cells in small (1 ml) scale in 96-well plates. Media was collected and used directly for ELISA in order to confirm binding to the ectodomain of mouse and human CD98hc. Human serum albumin was used as the negative control.

Upon reformatting to VNAR-hFc, 9 of the clones (bolded) retained their binding activity (Table 2), namely clones F1, D1, H6, H7, G3, E12, F11, A8 and F12. All clones showed variable expression levels in mammalian cells.

TABLE 2

| Clone ID | Expression [ug/mL] | Binding [relative units] | | |
|---|---|---|---|---|
| | | hCD98hc | mCD98hc | HSA |
| F1 | 26.32 | 3.757 | 0.115 | 0.073 |
| D1 | 22.74 | 3.495 | 0.417 | 0.074 |
| G12 | 39.09 | 0.044 | 0.044 | 0.054 |
| H6 | 4.387 | 3.314 | 0.186 | 0.06 |
| H7 | 9.698 | 3.934 | 0.108 | 0.072 |
| G3 | 34.96 | 1.479 | 0.041 | 0.053 |

TABLE 2-continued

| Clone ID | Expression [ug/mL] | Binding [relative units] | | |
|---|---|---|---|---|
| | | hCD98hc | mCD98hc | HSA |
| E12 | 17.69 | 2.192 | 0.078 | 0.056 |
| B12 | 4.035 | 0.076 | 0.084 | 0.081 |
| E12A | 8.592 | 0.049 | 0.065 | 0.063 |
| F11 | 2.062 | 3.032 | 0.096 | 0.072 |
| A8 | 4.218 | 2.973 | 0.135 | 0.065 |
| G6 | ND | 0.042 | 0.041 | 0.052 |
| H12 | 1.953 | 0.046 | 0.045 | 0.055 |
| F12 | 10.67 | 3.988 | 0.563 | 0.112 |
| H7A | 0.9652 | 0.043 | 0.043 | 0.054 |
| H8 | 6.429 | 0.048 | 0.049 | 0.059 |
| C6 | 42.54 | 0.041 | 0.042 | 0.052 |
| G10 | 36.48 | 0.043 | 0.041 | 0.051 |

Clones binding to CD98hc were then expressed at a larger scale. Expi293F (Invitrogen) cells were cultured in Expi293 expression medium (Invitrogen) supplemented with penicillin (100 U/ml), streptomycin (100 µg/ml) and maintained in a humidified shaking incubator at 37° C. and 5% $CO_2$. Cells were transfected using ExpiFectamine™M 293 Transfection Kit (Invitrogen) according to the manufacturer's protocol. Cells removed from the expression medium by centrifugation 5 days post transfection. The media was filtered and loaded onto PBS equilibrated MabSelect® Sure® Protein A columns (GE Life Sciences). The columns were washed with 10 volumes of PBS and the recombinant protein eluted with linear gradient of 0.1M glycine, pH 2.5 and PBS. Fractions containing the proteins were pooled and buffer exchanged to PBS using Sephadex® 25 desalting columns (GE Life Sciences). Protein concentrations were estimated by absorbance at 280 nm. Purified proteins were stored at −80° C. and once thawed maintained at 4° C. for a period of up to 2 weeks.

Eight of these could be purified in amounts sufficient for subsequent analyses. The biochemical EC50 (equilibrium constant, the concentration at which the ratio of bound to unbound is 50:50) of each of these clones was determined by serially diluting purified VNAR-Fc fusion proteins in blocking buffer (PBS-0.1% Tween+2.5% milk) and exposing it to preblocked Nunc® Maxisorp® 96-well plates coated at 1 µg/mL with human or murine CD98hc. After washing in PBS-0.1% Tween-20, bound. VNAR-Fc fusions were detected using a peroxidase-conjugated anti-FLAG antibody (Sigma). Absorbance at 450 nm was recorded using an Envision multiwell reader (Perkin Elmer) and EC50s were calculated by fitting curves (non-linear regression) using GraphPad Prism® software.

Figure 3A:
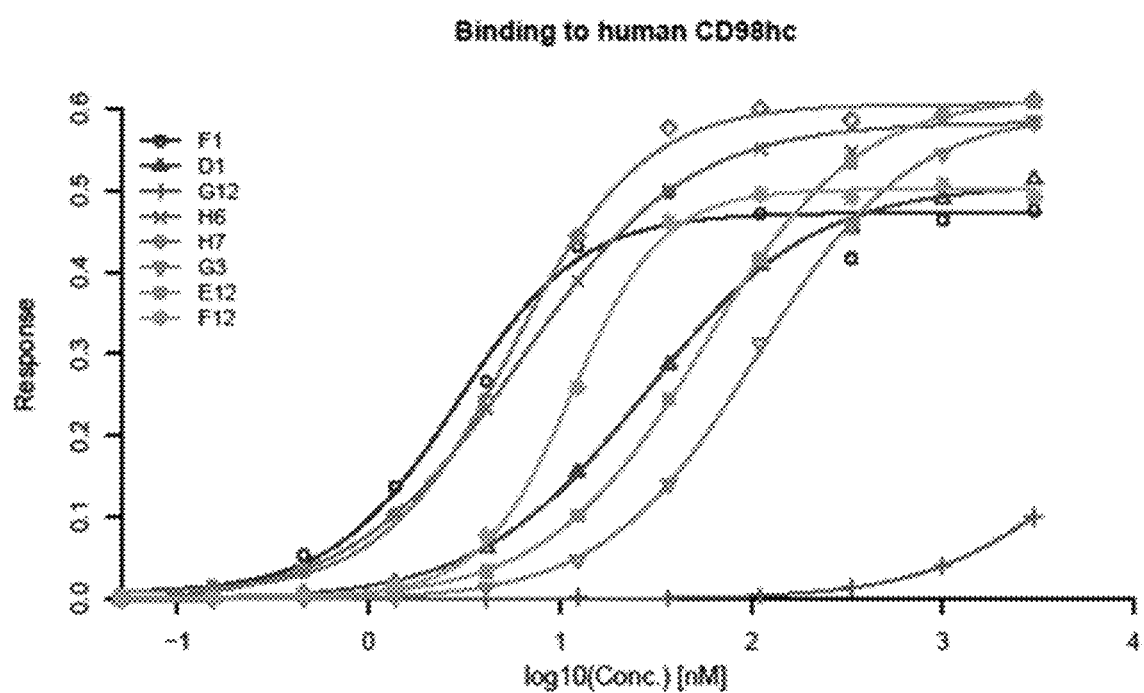
FIG. 3. ELISA binding of Fc formatted anti-CD98hc VNAR fusions to recombinant (A) human and (B) mouse CD98hc.
Figure 3B:
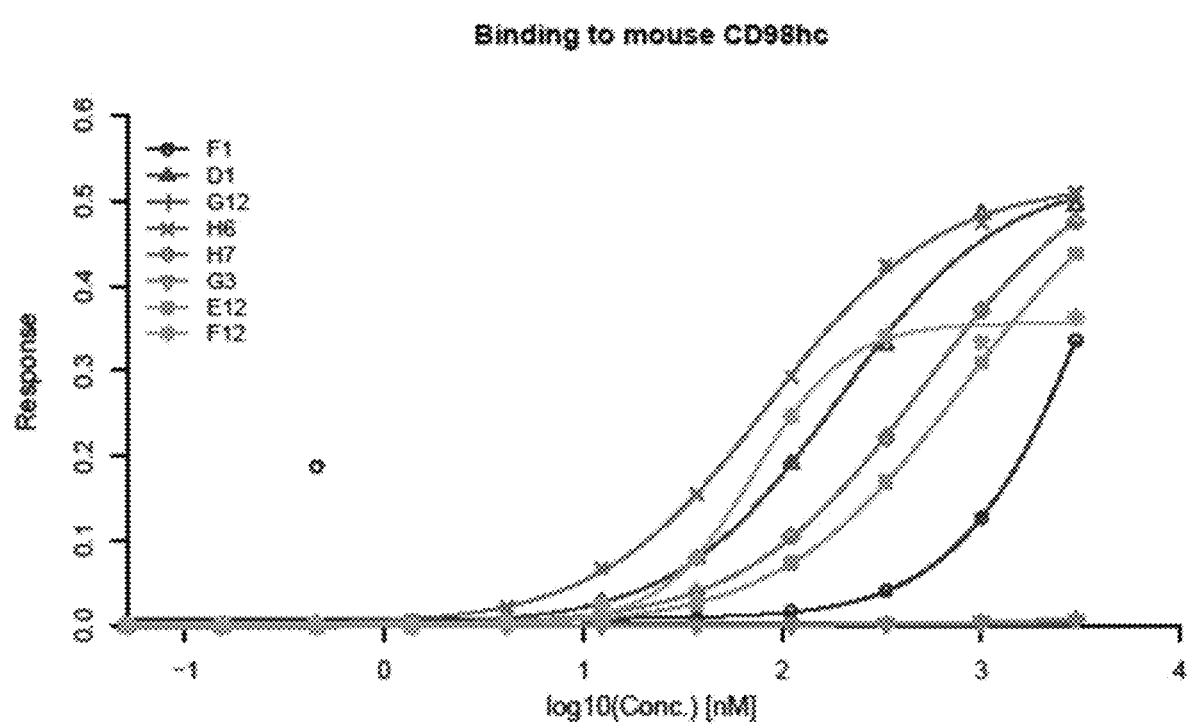

EC50 values for binding of the 8 clones to human and mouse CD98hc are shown in FIGS. 3A and 3B. One clone showed very low binding to both proteins and the other appeared to bind better to human than to mouse CD98hc. EC50s for the human protein ranged from 3 to 107 nM and for mouse from 72 nM to 3.9 uM (Table 3).

TABLE 3

| Clone ID | EC50 [nM] | |
|---|---|---|
| | mouse CD98hC | human CD98hC |
| F1 | 3859 | 3 |
| D1 | 190 | 28 |
| G12 | ND* | ND |

TABLE 3-continued

| Clone | EC50 [nM] | |
|---|---|---|
| ID | mouse CD98hC | human CD98hC |
| H6 | 86 | 6 |
| H7 | 504 | 6 |
| G3 | ND | 107 |
| E12 | 819 | 56 |
| F12 | 72 | 12 |

*Weak binder, EC50 could not be determined

Example 4. Brain Uptake of CD98hc Binders

Figure 4:
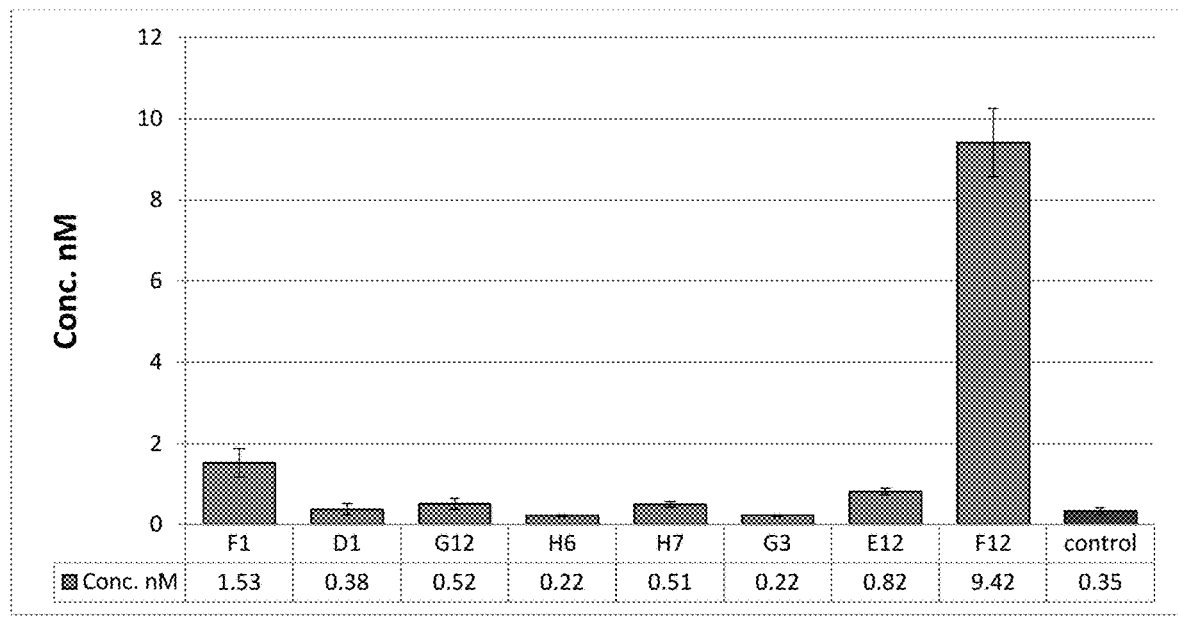
FIG. 4. Brain uptake of CD98hc binding VNAR-hFc fusions. Mice were injected intravenously with 25 nmol/kg and perfused 18 hours later. Concentration in brain was determined by hFc capture ELISA in brain extracted with 1% Triton in PBS as described in the examples.
Figure 5:
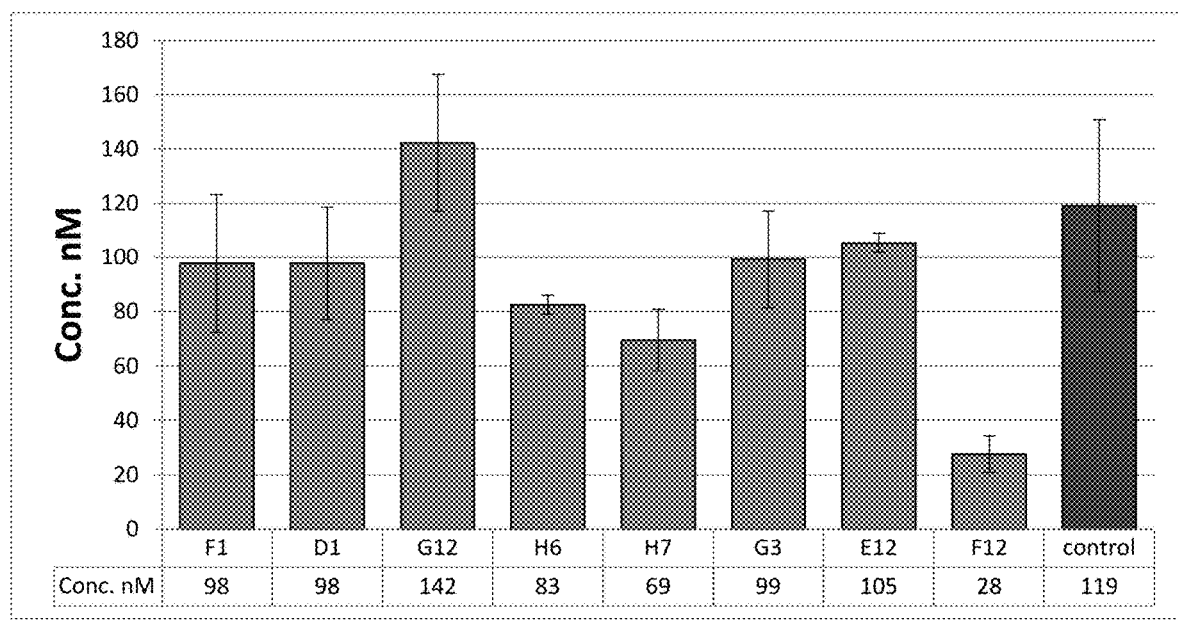
FIG. 5. Plasma levels of CD98hc binding VNAR-hFc clones. Plasma was prepared from blood collected from the mice used in FIG. 2 and concentrations were determined by hFc capture ELISA as described in the examples.
Figure 6:
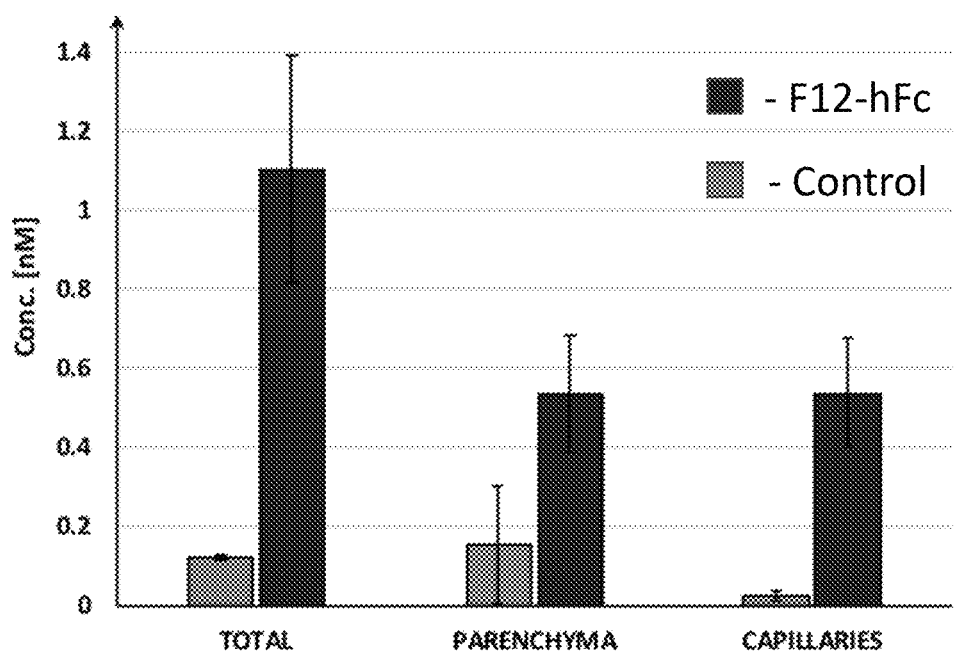
FIG. 6. Distribution of F12-hFc fusions in brain. Mice were injected intravenously with 25 nmol/kg of F12-hFc or control VNAR-hFc fusion and perfused 18 hours later. Brains were fractionated by dextran gradient centrifugation. Parenchymal and capillary fractions were lysed in 1% Triton X-100 containing protease inhibitors and the concentrations of injected proteins was determined by hFc-capture ELISA.

All 8 binders were tested for their blood-brain barrier penetration activity as described in WO2018/031424. Briefly, mice were injected with 25 nmol/kg (~1.9 mg/kg) of the VNAR-hFc fusion and perfused 18 hours later with PBS supplemented with heparin. The brains were dissected, placed in lysis buffer (3:1 v/w ratio) containing 1% Triton X-100 in PBS supplemented with cOmplete® Protease Inhibitor Cocktail (Roche). Brains were homogenized with a TissueRuptor® (Qiagen) homogenizer at medium speed for 10 seconds and lysed for 30 min on ice. Lysates were centrifuged at 17,000×g for 20 min and the supernatant was blocked in 2.5% milk in PBST overnight at 4° C. VNAR-Fc amounts in the extract were measured using human Fc capture ELISA (Rülker et al. (2010) In: Kontermann R., Dübel S. (eds) Antibody Engineering. Springer, Berlin, Heidelberg). Of tested clones, 3 showed brain levels higher than. control VNAR (FIG. 4): clone E12 (2.3-fold), clone F1 (4.4-fold), and clone F12 (26.9-fold). All clones except for F12 showed comparable levels in plasma 18h post-injection (FIG. 5). The majority of F12-hFc protein was transported through the blood-brain barrier and found in brain parenchyma (FIG. 6).

Figure 7:
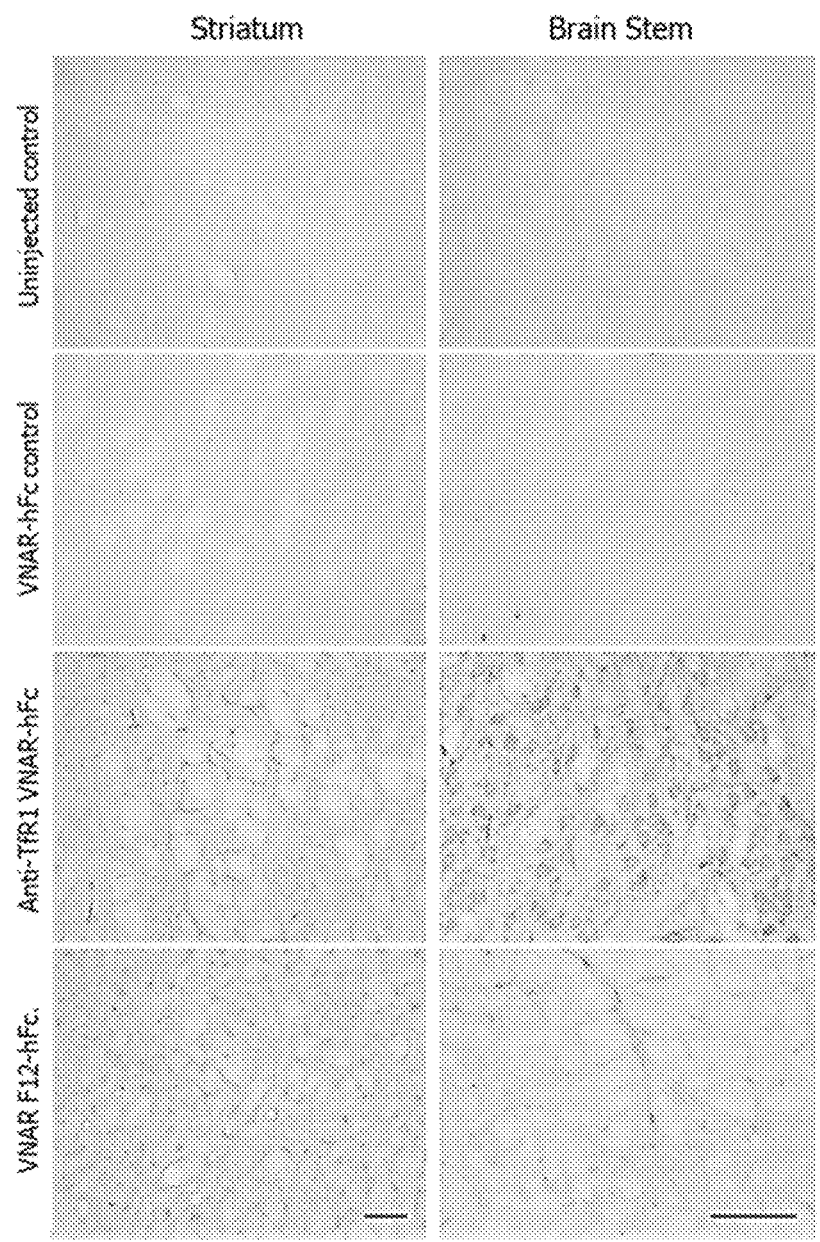
FIG. 7. Immunohistochemical localization of VNAR F12-hFc fusions in mouse brain. The distribution of an anti-CD98 VNAR-hFc was compared to an anti-TfR1 VNAR-hFc in the striatum (left panels) and brain stem (right panels) 18 hours after a 12 mg/kg, IV injection.

Immunohistochemical analysis was used to determine the distribution of an F12-hFc protein was compared to an anti-TfR1 VNAR-hFc protein in the striatum and brain stem. The fusion proteins were injected intravenously into a mouse tail vein at 12 mg/kg as described above, and brains harvested at 18 hours after injection and striatem and brain stem sections were prepared for staining. The results show that the F12-hFc protein (to CD98hc) and the VNAR-Fc fusions against TfR1 are found in capillaries and the parenchyma of the striatum whereas only the anti-TfR1 VNAR fusion is found in brain stem neurons (FIG. 7). Neither the uninjected control nor a control VNAR-Fc at the same dose and time point show any staining.

Example 5. Characterization of Clone F12

Figure 8:
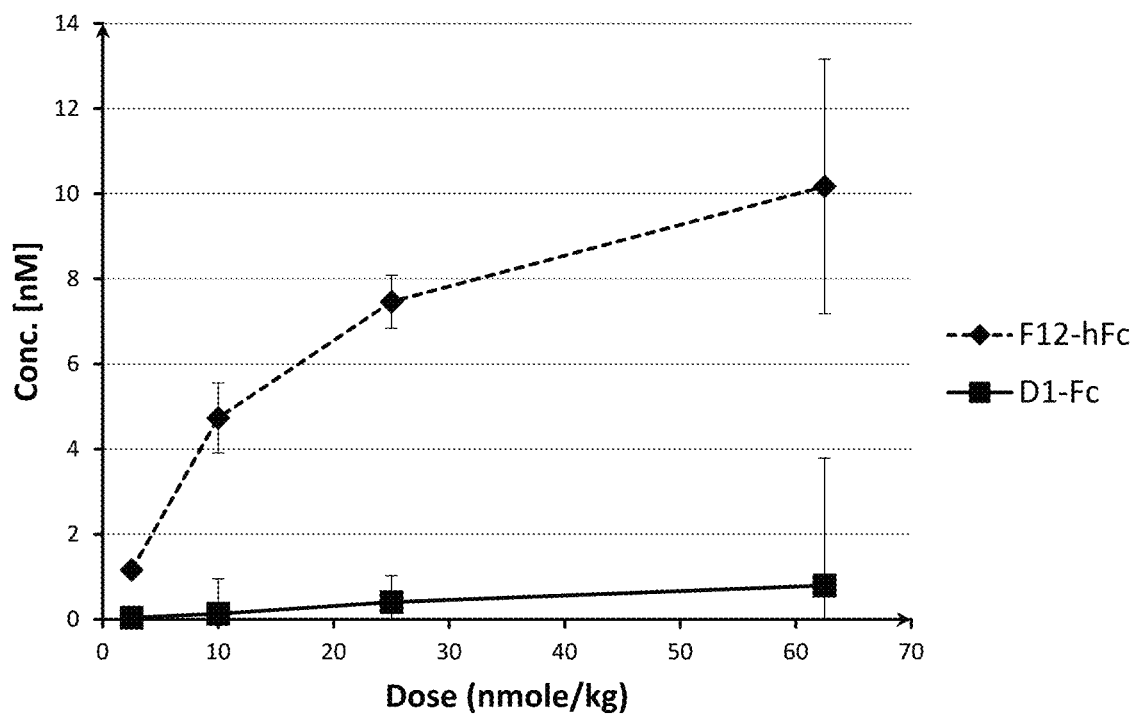
FIG. 8. Dose-dependent brain uptake of VNAR F12-hFc. Mice were injected intravenously with ascending doses of F12-hFc or D1-hFc control and perfused 18 hours later. The brains were dissected and concentrations in homogenates were determined by hFc capture ELISA.
Figure 9:
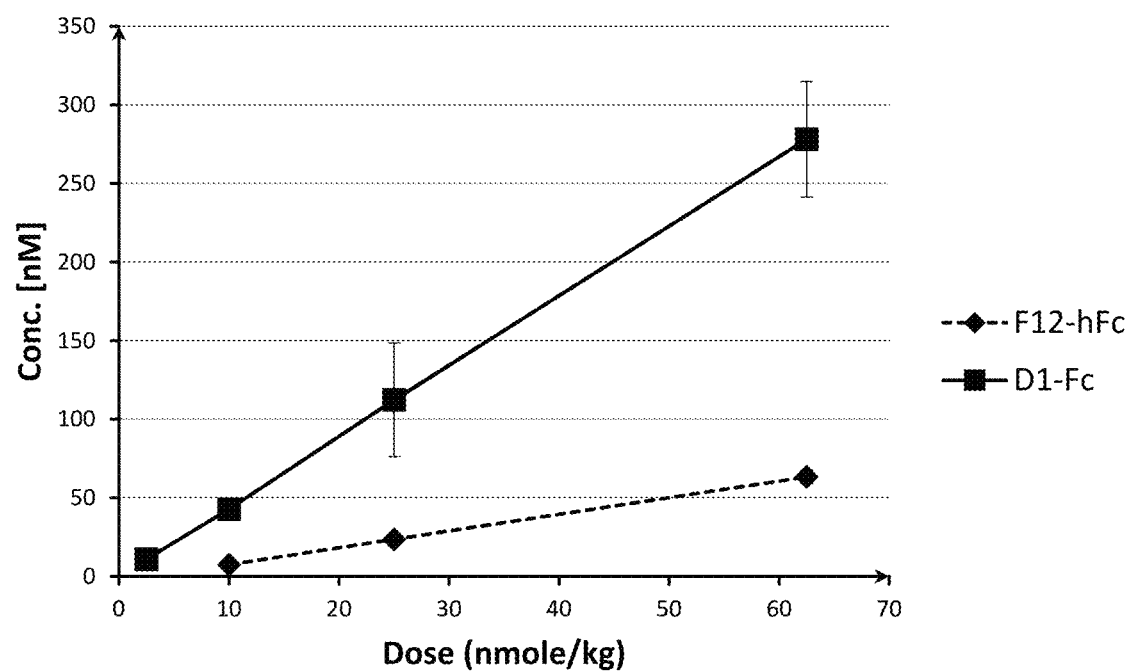
FIG. 9. Dose-dependent plasma concentration of VNAR F12-hFc. Plasma was prepared from blood collected from the mice used in FIG. 5 and concentrations were determined by hFc capture ELISA.

Clone F12 showed the greatest potential as a brain shuttle and was further characterized. Different doses of the F12-hFc and D1-hFc (a CD98hc binder with brain uptake comparable to control VNAR) proteins were injected into mice at doses of 2.5 nmol/kg, 10 nmol/kg, 25 nmol/kg, and 62.5 nmol/kg (corresponding to 0.2, 0.8, 1.9 and 4.7 mg/kg) and proteins were extracted as described in Example 4. Both proteins showed linear dependence of plasma levels on the dose injected (FIG. 8). Brain uptake of F12-hFc showed a saturable dose response indicating a specific uptake whereas the negative clone showed low linear dose dependent increase in brain levels (FIG. 9).

Figure 10:
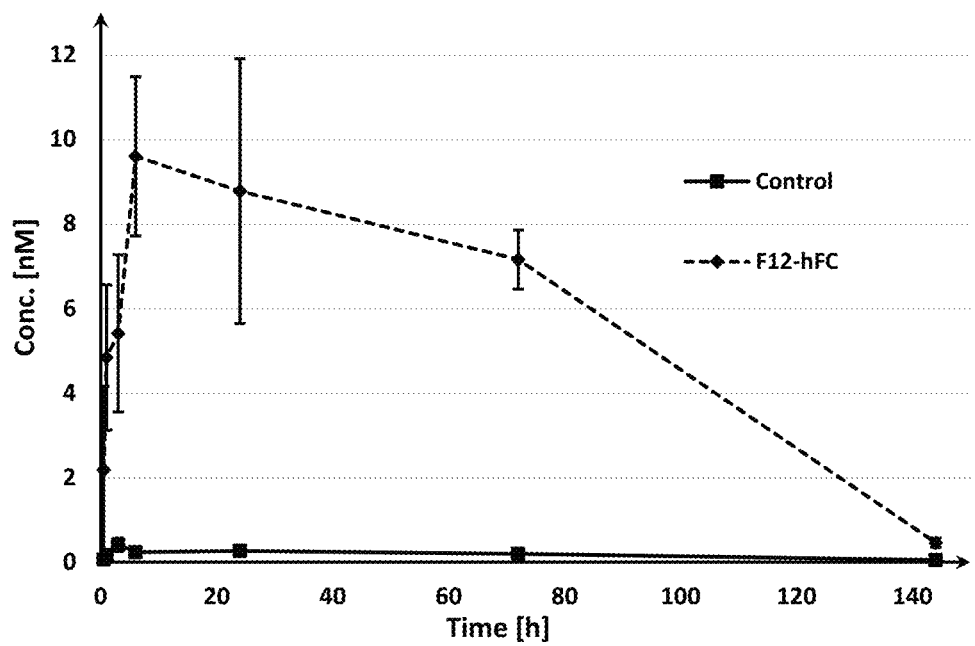
FIG. 10. Time course of brain exposure after a single dose of VNAR F12-hFc. Mice were injected intravenously with 25 nmol/kg and perfused after various time-points. Brains were dissected and the concentration in homogenates was determined by hFc capture ELISA.
Figure 11:
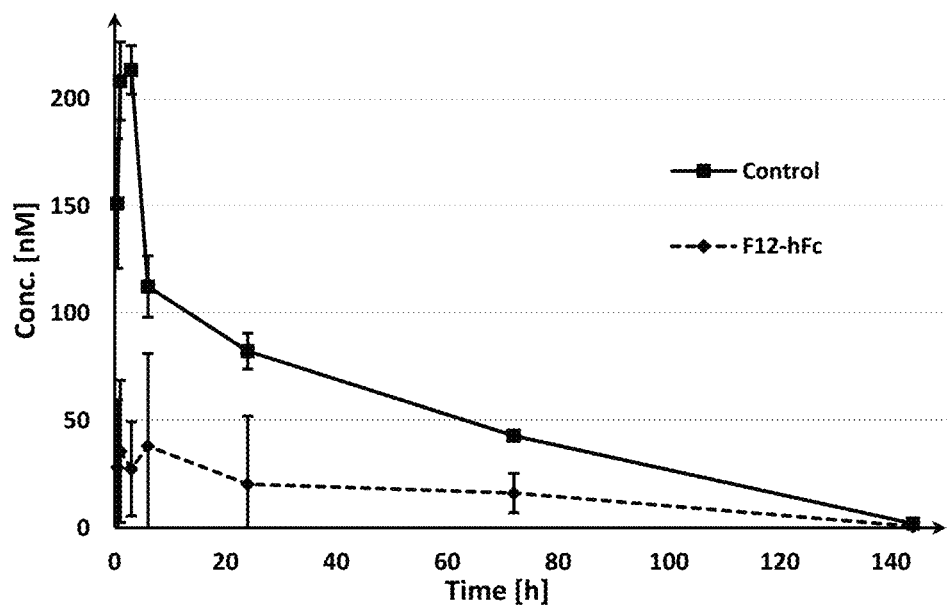
FIG. 11. Time course of plasma concentration after a single dose of VNAR F12-hFc. Plasma was prepared from blood collected from the mice used in FIG. 7 and concentrations were determined by hFc capture ELISA FIG. 12. Rituximab—F12 VNAR bi-specific formats.

In the time course experiment, F12-hFc and D1-hFc were injected at 25 nmol/kg dose and brains harvested at 0.5, 1, 3, 6, 24, 72, and 144 hours after injection. Plasma and brain levels were measured as before. The negative comparator VNAR showed low brain levels throughout the course of this experiment while clone F12 very quickly appeared in the brain with a peak between 6 and 24 h (FIG. 10). After 72 h there was still approximately 75% of the maximal measured concentration in the brain. As seen before, plasma levels of F12-hFc were significantly lower than those of D1-hFc though it mostly resulted from significantly higher drop in F12 levels during distribution phase, while the two molecules behaved more similarly during elimination phase (FIG. 11).

Example 6. Brain Uptake of a Therapeutic Payload

The ability of F12 VNAR to shuttle therapeutic antibodies to the brain was tested. F12 was expressed in mammalian cells as either N- or C-terminal fusions to either heavy or light chain of anti-human CD20 antibody—Rituximab (FIG. 12) using knob-into-holes technology (Ridgeway et al., Protein Engineering vol. 9 no. 7 pp. 617-621, 1996). The panel of bispecific antibodies were purified from CHO cell supernatants after transient transfection.

Figure 13:
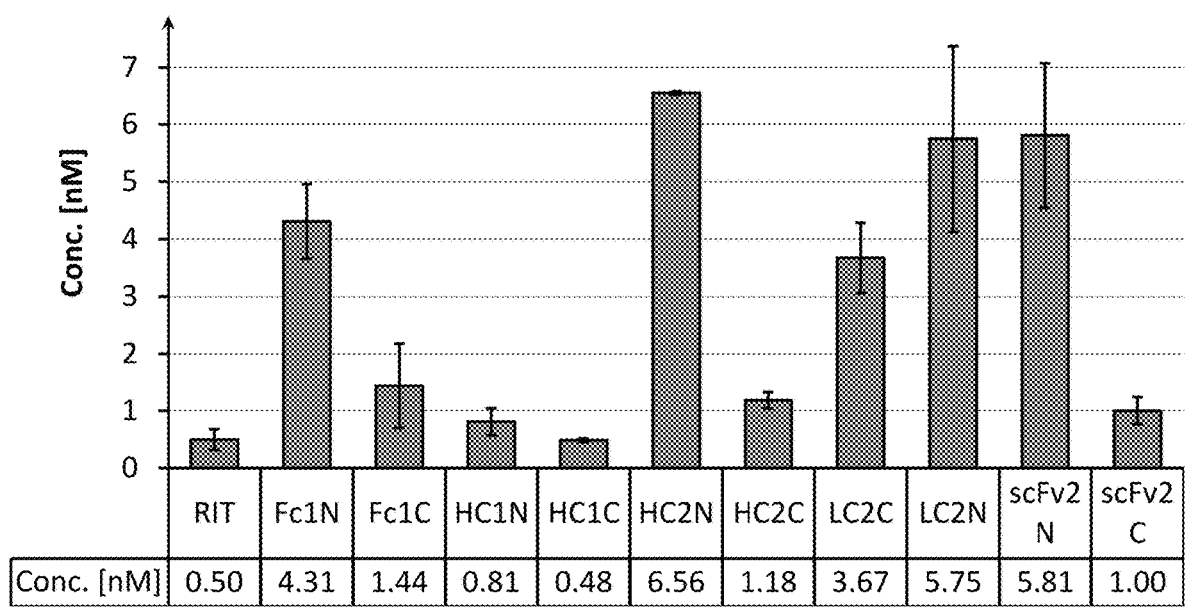
FIG. 13. Brain uptake of F12-rituximab bispecific formats. Mice were injected intravenously with 25 nmol/kg and perfused 18 hours later. Brains were dissected and the concentration was determined in the homogenates by hFc capture ELISA.
Figure 14:
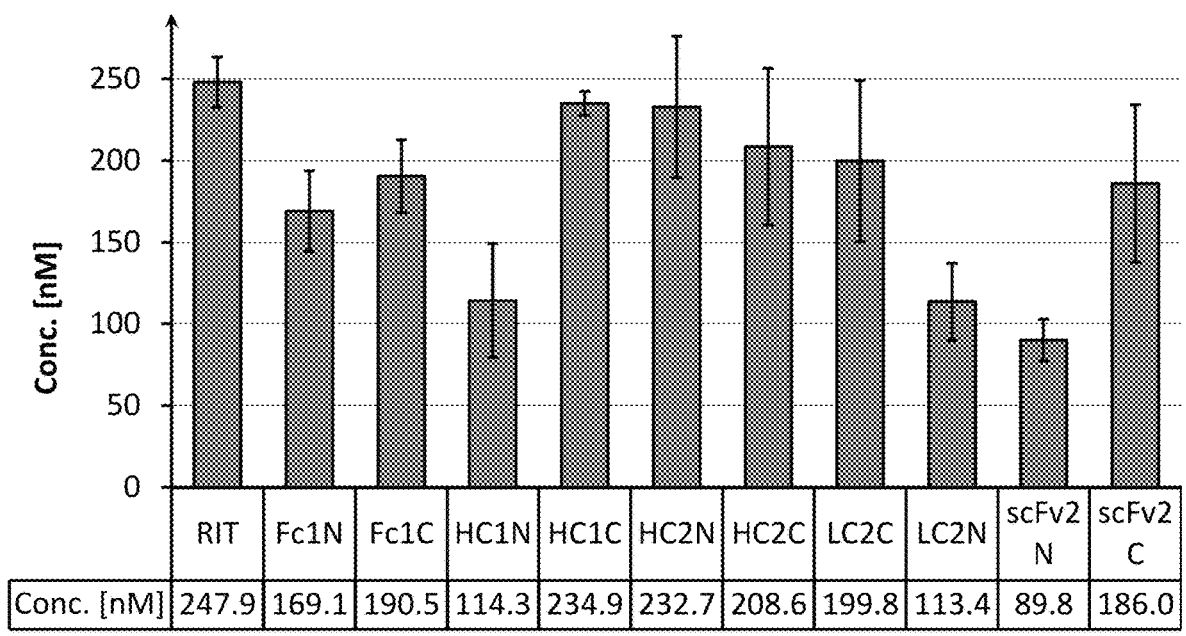
FIG. 14. Plasma concentration of F12-rituximab bispecific formats. Plasma was prepared from blood collected from the mice used in FIG. 10 and concentrations were determined by hFc capture ELISA.

Mice were injected with the bi-specific antibodies 25 nmol/kg dose and their plasma levels and brain uptake tested by human Fc capture ELISA. As shown in FIG. 13, 5 formats of RIT-F12; LC2N, HC2N, LC2C, Fc1N, and scFv2N showed significant brain uptake- between 7 and 14× better than rituximab. For three variants (scFv2N, HCIN, LC2N), PK in plasma was significantly lower than for unmodified rituximab (FIG. 14).

Table 4 provides the brain uptake of clone F12-bispecific rituximab formats over rituximab alone. The fold difference in brain uptake was calculated from data presented in FIG. 13 using concentration measured for unmodified rituximab as reference. Brain/plasma ratios were calculated from data in FIG. 13 and FIG. 14. The best BBB shuttle formats showed ~7- to 13-fold high brain concentration than the unmodified rituximab with brain/plasma ratios from 2.5-6% at 18 h after IV injection.

TABLE 4

| | Brain uptake (Fold over RIT) | brain/plasma [%] |
|---|---|---|
| RIT | 1.0 | 0.2 |
| Fc1N | 8.7 | 2.5 |
| Fc1C | 2.9 | 0.8 |
| HC1N | 1.6 | 0.7 |
| HC1C | 1.0 | 0.2 |

TABLE 4-continued

|       | Brain uptake (Fold over RIT) | brain/plasma [%] |
|-------|------------------------------|------------------|
| HC2N  | 13.2                         | 2.8              |
| HC2C  | 2.4                          | 0.6              |
| LC2C  | 7.4                          | 1.8              |
| LC2N  | 11.6                         | 5.1              |
| scFv2N| 11.7                         | 6.5              |
| scFv2C| 2.0                          | 0.5              |

Figure 12:
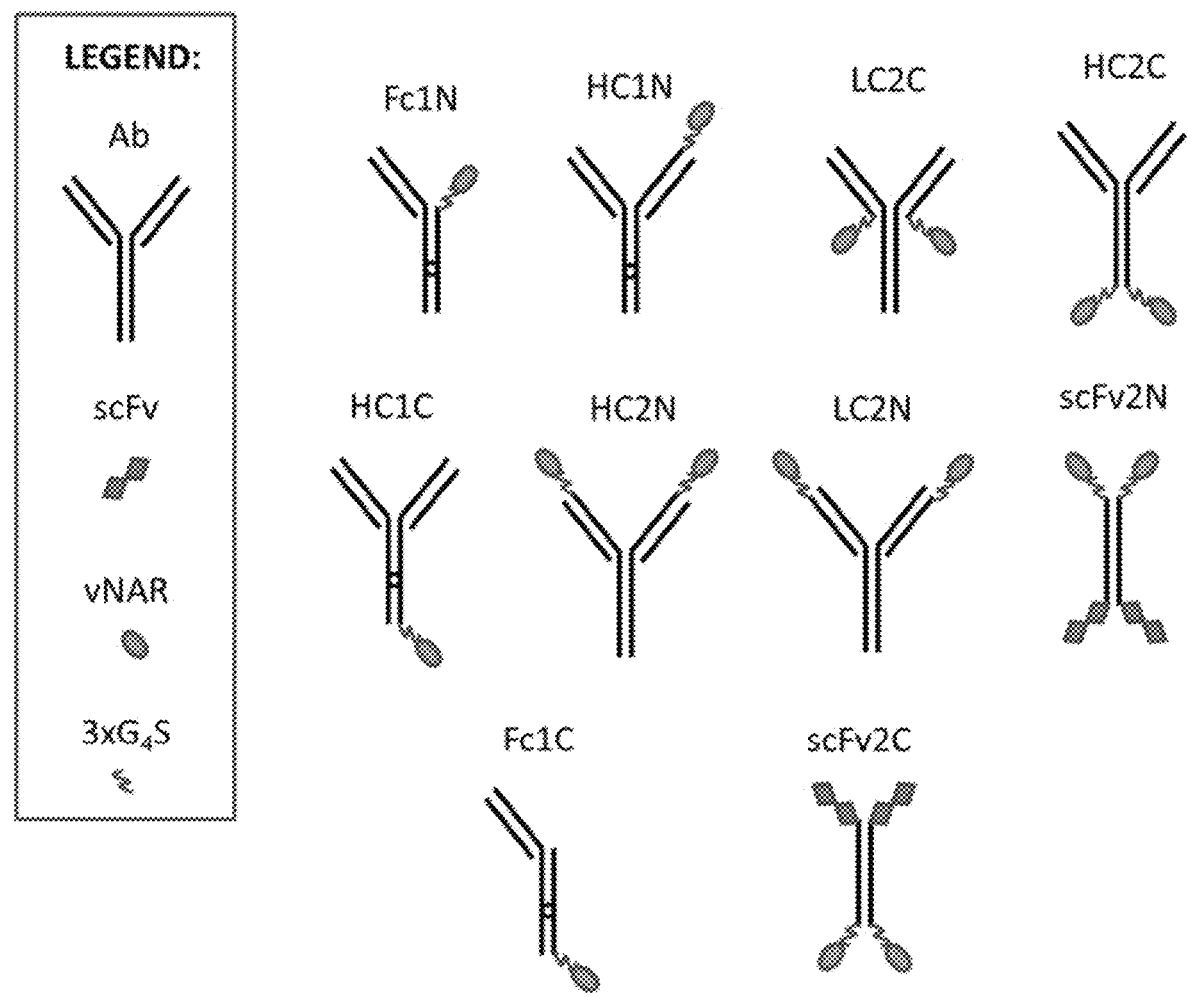

The following abbreviations are used in Table 4 and FIG. 12: Ab, RIT antibody; C, C-terminus; G$_4$S (SEQ ID NO. 97), Fc, the Fc domain of a conventional antibody; H, heavy chain; L, light chain; N, N-terminus; RIT, rituximab; scFv, single chain variable domain of a conventional antibody.

Example 7. Preparation of Clone F12 Variants

Clone F12, obtained as described in Example 2, is a Type IV VNAR domain having an amino acid sequence of (SEQ ID NO. 20)
ARVDQTPQTITKEEGESLTINCVLR*VHGRALAS*

TSWYRKKSGS*TREETISKG*GRYVETVN*SGSKSF*

SLRINDLTVEDSGTYRCN<u>VYGLSFGDIEGVKKI</u>

<u>DV</u>YGDGTAVTVNA.

The CDR1, HV2 and HV4 domains, appearing in order from left to right, are italicized and bolded, and the CDR3 domain is underlined and bolded.

Figure 15:
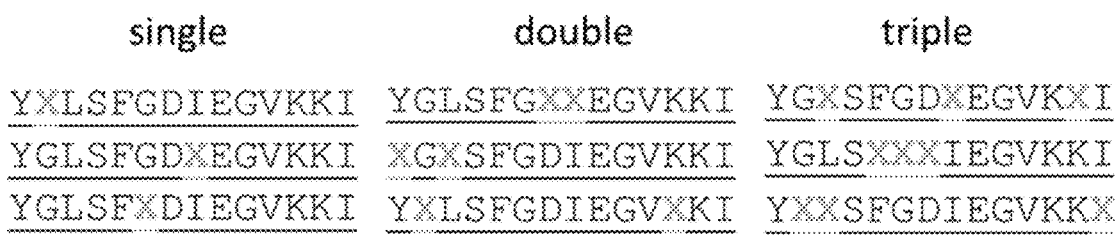
FIG. 15. CDR3 Mutagenesis strategy for F12 variants.

To improve BBB shuttling function of Clone F12, using a multiplex PCR process, the F12 CDR3 was mutated by making all possible permutations of single, double and triple amino acid substitutions in positions 2-15 of CDR3 to produce 183 sub libraries which were pooled for screening. An example of 9 such sublibraries, exemplifying various combinations of single, double and triple changes is shown in FIG. 15. To preserve Type IV VNAR architechture, this approach allowed preparation of oligonucleotides that did not encode cysteine or a stop condon.

The pooled phage display libraries were subjected to further in vitro or in vivo selection as described in Examples 8 and 9 below.

Example 8. In Vitro Selection of F12 Variants on Recombinant Mouse and Human CD98hc The F12 variant phage sublibrary of Example 7 was subjected to in vitro biopanning on human CD98hc TfR1 and screening on mouse CD98hc as described above in Example 2. After three rounds of selection, individual colonies were picked and approximately 200 clones were sequenced.

Analysis of the sequence data lead to a CDR3 consensus sequence for F12 VNAR variants that retained binding to both human and mouse CD98 (Table 5), which data is also represented in SEQ ID NO. 5. The top line of the table is the CDR3 sequence of F12.

TABLE 5

CDR3 consensus sequence for F12 and its variants

| V | Y | G | L | S | F | G | D | I | E | G | V | K | K | I | D | V |
|---|---|---|---|---|---|---|---|---|---|---|---|---|---|---|---|---|
|   | N |   | V | E | S | L | K | A | G | E | L | G | Q | L |   |   |
|   | F |   |   | Q | T | K | G | D | Q | R | W | N |   |   |   |   |
|   | D |   |   | R | G | E | H | E | W | W | Y |   |   |   |   |   |
|   | W |   |   | G | N | M | M | F | K |   | P |   |   |   |   |   |
|   | H |   |   | K | K | W | S | G | V |   |   |   |   |   |   |   |
|   | K |   |   | L | M | V | A | H | L |   |   |   |   |   |   |   |
|   | S |   |   | M | A | Y | P | K | M |   |   |   |   |   |   |   |
|   |   |   |   |   | H |   | T | L | A |   |   |   |   |   |   |   |
|   |   |   |   |   | I |   |   | M | H |   |   |   |   |   |   |   |
|   |   |   |   |   | L |   |   | N | R |   |   |   |   |   |   |   |
|   |   |   |   |   | Q |   |   | Q | Y |   |   |   |   |   |   |   |
|   |   |   |   |   | R |   |   | S |   |   |   |   |   |   |   |   |
|   |   |   |   |   | W |   |   | Y |   |   |   |   |   |   |   |   |
|   |   |   |   |   | Y |   |   |   |   |   |   |   |   |   |   |   |

Figure 16A:
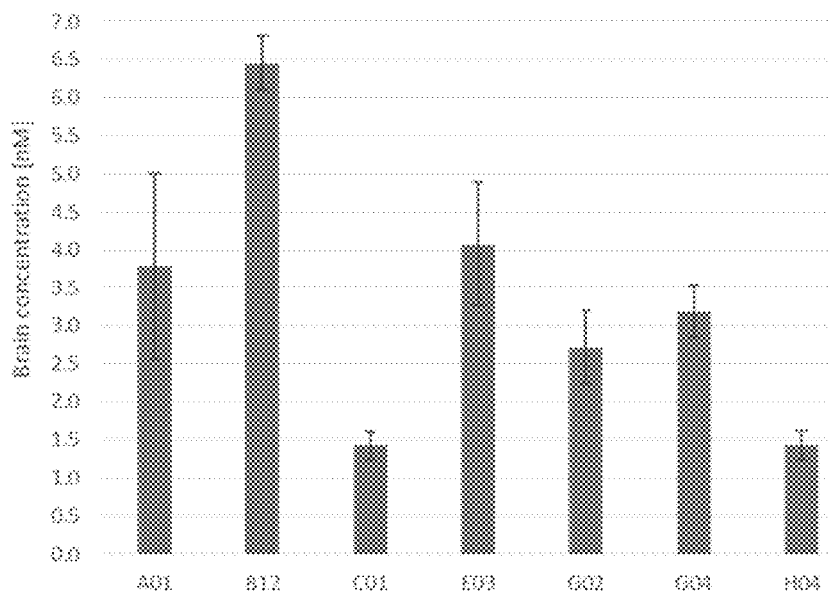
FIG. 16. Brain and plasma concentrations for selected F12 variants as VNAR-hFc fusions. Mice received a single IV injection of 25 nmol/kg and were perfused and brains isolated for analysis 18 hours after injection (N=3, +/−SD).
Figure 16B:
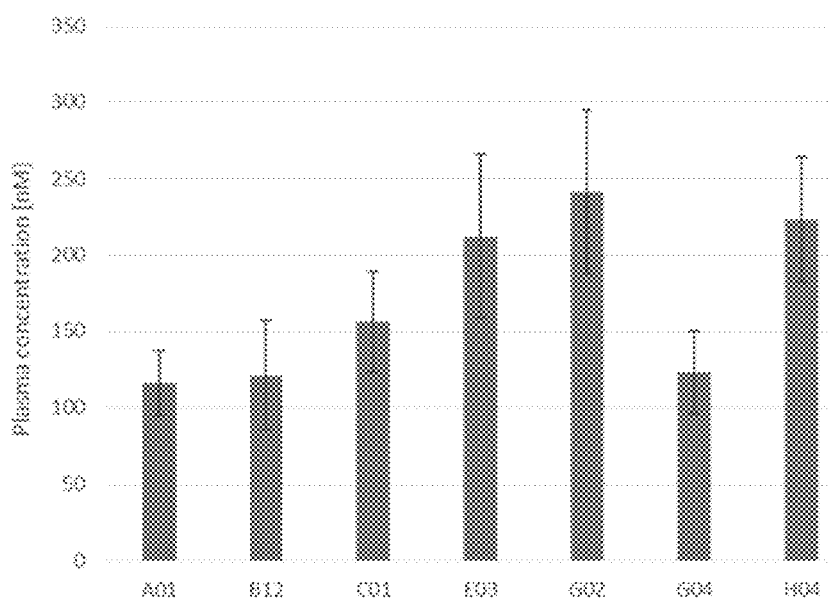
Figure 17:
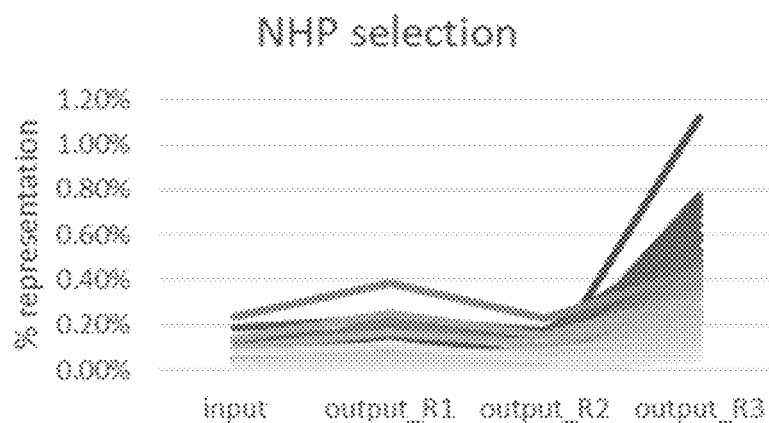
FIG. 17. NGS analysis of in vivo selection in mouse, rat and non-human primate (NHP). Clones that showed the highest abundancy in the output round 3 were traced back for the abundancy in the previous rounds of selection as well as in the input. The sequences of the plotted clones are included in Tables 7-9.
Figure 17:
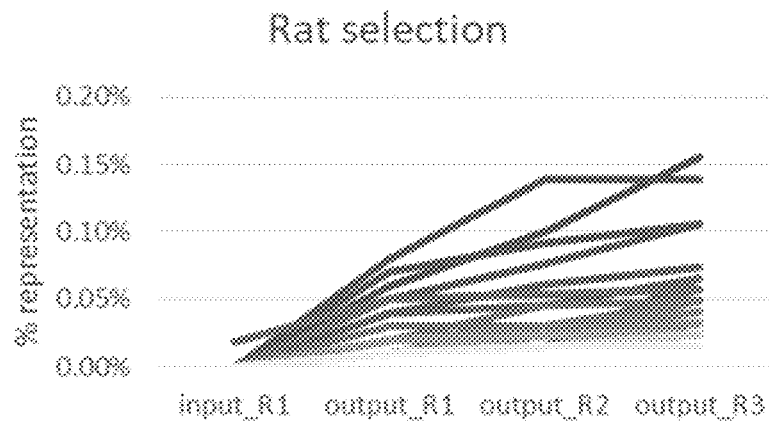
Figure 17:

Several of these cross reactive CD98hc binding clones were formatted as VNAR-hFc fusions and EC50 values for binding to human CD98 as determined by ELISA using the method described in Example 3. The results are shown in Table 6. Residues with substitutions relative to the parental F12 clone are bolded (and the font slightly enlarged). The column under the symbol # provides the SEQ ID NOS. of the CDR3 sequences Studies of the brain and plasma distribution of the F12 variant VNAR-Fc fusions were conducted as described in Example 4. The results are shown in FIG. 16A (brain) and FIG. 16B (plasma).

selection round, the brains were extracted 1 hour after phage injection and the recovered phage were subjected to Next Generation Sequence (NGS) analysis (as was the initial library). The high abundance sequences obtained after the third selection round were traced back for their abundance in the previous rounds. Clones that showed consistent amplification throughout the selection process are shown in FIG. 17 for each species and the sequences of those clones are provided in Table 7 for the macaque-derived clones (NHP), in Table 8 for the rat-derived clones (RT) and in Table 9 for the mouse-derived clones (MS). All clones had the same VNAR framework regions, CDR1, HV2 and HV4 sequences

TABLE 6

EC50 values and CDR3 Sequences of VNAR-Fc fusions for F12 variants

| Clone | EC50 | CDR3 Sequence | # | | | | | | | | | | | | | | |
|---|---|---|---|---|---|---|---|---|---|---|---|---|---|---|---|---|---|
| F12-A01 | 1E-08 | VNGL SSGD KEGV KKID V | 98 | V | N | G | L | S | S | G | D | K | E | G | V | K | K | I | D | V |
| F12-B12 | 1E-08 | VNGL SSGD IEGV KKL DV | 99 | V | N | G | L | S | S | G | D | I | E | G | V | K | K | L | D | V |
| F12-C01 | 3E-08 | VYGL SSGD SEGV KKID V | 100 | V | Y | G | L | S | S | G | D | S | E | G | V | K | K | I | D | V |
| F12-E03 | 4E-08 | VNGL SSGD QEGV KKID V | 101 | V | N | G | L | S | S | G | D | Q | E | G | V | K | K | I | D | V |
| F12-G02 | 1E-08 | VYGL MNVD IEGV KKID V | 102 | V | Y | G | L | M | N | V | D | I | E | G | V | K | K | I | D | V |
| F12-G04 | 3E-08 | VNGL SSGD IEGV KKID V | 103 | V | N | G | L | S | S | G | D | I | E | G | V | K | K | I | D | V |
| F12-H04 | 2E-08 | VYGL MQGD IEGV KKID V | 104 | V | Y | G | L | M | Q | G | D | I | E | G | V | K | K | I | D | V |

Example 9. In Vivo Selection of Brain Penetrant F12 Variants in fication in the NGS analysis shown in FIG. 17B. For the mouse-selected clones, Table 9 provides 125 F12 VNAR variants (with randomized CDR3 region) and includes all clones that showed consistent amplification in the NGS analysis shown in FIG. 17C.

TABLE 7

CDR3s of F12 Variants from in vivo selection in non-human primates

| Clone ID | SEQ. ID NO. | CDR3 | % in R3 |
|---|---|---|---|
| NHP-1 | 105 | VNGRSFGDIEGVKKIDV | 1.12% |
| NHP-2 | 106 | VHFLRFGDIEGVKKIDV | 0.77% |
| NHP-3 | 107 | VYGQSFGDIELVKKIDV | 0.74% |
| NHP-4 | 108 | VYGLSFGLIEGVKKIDV | 0.73% |
| NHP-5 | 109 | VEGLSNGDIEEVKKIDV | 0.72% |
| NHP-6 | 110 | VWGLSFGDIEGVKKIDV | 0.68% |
| NHP-7 | 111 | VLGLSFGDWGGVKKIDV | 0.65% |
| NHP-8 | 112 | VYGLSYGLFEGVKKIDV | 0.60% |
| NHP-9 | 113 | VYGLSFGDFEGVKKIDV | 0.59% |
| NHP-10 | 114 | VYGFSFGSIEGVKKIDV | 0.58% |
| NHP-11 | 115 | VRGLYTGDIEGVKKIDV | 0.54% |
| NHP-12 | 116 | VYGQSFGDIEGVKKIDV | 0.54% |
| NHP-13 | 117 | VYGMLFGDIEGVKKIDV | 0.53% |
| NHP-14 | 118 | VYGLSYGDIEGVKKIDV | 0.52% |
| NHP-15 | 119 | VYGLSYGDIGGVKKIDV | 0.51% |
| NHP-16 | 120 | VYGESFGLIEGVKKIDV | 0.49% |
| NHP-17 | 121 | VHGLSFQDIEGVKKIDV | 0.46% |
| NHP-18 | 122 | VYGLSFGDISGVKKIDV | 0.46% |
| NHP-19 | 123 | VWGLSFGRIEGVKKIDV | 0.46% |
| NHP-20 | 124 | VYGLQLGDIEQVKKIDV | 0.46% |
| NHP-21 | 125 | VYGLSLGDIEGFKKIDV | 0.46% |
| NHP-22 | 126 | VYLLSFGDIEGVQKIDV | 0.46% |
| NHP-23 | 127 | VYGLSFGDILGVKKIDV | 0.46% |
| NHP-24 | 128 | VYGLSVGDIEGVKKIDV | 0.46% |
| NHP-25 | 129 | VYGGLFGDNEGVKKIDV | 0.45% |
| NHP-26 | 130 | VYELSSGDIEGVKKIDV | 0.44% |
| NHP-27 | 131 | VYGLSFRDIGGVKKIDV | 0.44% |
| NHP-28 | 132 | VYGLSLGDIEGVKKIDV | 0.44% |
| NHP-29 | 133 | VYDESFRDIEGVKKIDV | 0.43% |
| NHP-30 | 134 | VYGLSFRDIEGVKKIDV | 0.43% |
| NHP-31 | 135 | VYGRSFGDIEKVKKIDV | 0.43% |
| NHP-32 | 136 | VFGWSFLDIEGVKKIDV | 0.43% |
| NHP-33 | 137 | VYGLDFGDMEGVKKIDV | 0.42% |

TABLE 7-continued

CDR3s of F12 Variants from in vivo selection in non-human primates

| Clone ID | SEQ. ID NO. | CDR3 | % in R3 |
|---|---|---|---|
| NHP-34 | 138 | VYGLSFGDKEKVKKIDV | 0.42% |
| NHP-35 | 139 | VYGLSEGDYEGVKKIDV | 0.41% |
| NHP-36 | 140 | VYGMSFGDVEGVKKIDV | 0.40% |
| NHP-37 | 141 | VYGLSFGSNEGVKKIDV | 0.38% |
| NHP-38 | 142 | VYGVSFGDIEGVKKIDV | 0.38% |
| NHP-39 | 143 | VIGLSFGDLWGVKKIDV | 0.38% |
| NHP-40 | 144 | VYGLFFGDIEGVKKIDV | 0.37% |
| NHP-41 | 145 | VYGLSFGDIEGQKKIDV | 0.37% |
| NHP-42 | 146 | VYGLSHGDIGGVKKIDV | 0.35% |
| NHP-43 | 147 | VNGLSFKDIEGVKDIDV | 0.34% |
| NHP-44 | 148 | VYMYMFGDIEGLKKIDV | 0.34% |
| NHP-45 | 149 | VFGLSFGDIEGVKKIDV | 0.33% |
| NHP-46 | 150 | VFGWSFGDIEGVKKIDV | 0.33% |
| NHP-47 | 151 | VLGMSFGEIEGVKKIDV | 0.33% |
| NHP-48 | 152 | VNGWSHGDIEGVKKIDV | 0.33% |
| NHP-49 | 153 | VYGLSFGDIMGVKKIDV | 0.33% |
| NHP-50 | 154 | VYGLSFKDIWGVKKIDV | 0.33% |
| NHP-51 | 155 | VYELSFGDIEGVKYIDV | 0.33% |
| NHP-52 | 156 | VWGLSFGDFEGVKKIDV | 0.32% |
| NHP-53 | 157 | VYGWSFGDILGVKKIDV | 0.32% |
| NHP-54 | 158 | VYGWFFGDHEGVKKIDV | 0.31% |
| NHP-55 | 159 | VYGLSFGDIEEVKKIDV | 0.27% |
| NHP-56 | 160 | VYGMFFKDIEGVKKIDV | 0.25% |
| NHP-57 | 161 | VTGMSFGDDEGVKKIDV | 0.24% |
| NHP-58 | 162 | VYKWSFMDIEGVKKIDV | 0.24% |
| NHP-59 | 163 | VYGWSFGDNWGVKKIDV | 0.22% |
| NHP-60 | 164 | VYKLSKGDIEGVKKIDV | 0.22% |
| NHP-61 | 165 | VWKLSFGDIEGVKKIDV | 0.21% |
| NHP-62 | 166 | VYLLSFFDLEGVKKIDV | 0.17% |
| NHP-63 | 167 | VYGLVYIDIEGVKKIDV | 0.17% |
| NHP-64 | 168 | VFGLSFWDIEGVKKIDV | 0.16% |
| NHP-65 | 169 | VYGLSSGDIEGMKKIDV | 0.16% |
| NHP-66 | 170 | VFNLVFGDIEGVKKIDV | 0.16% |
| NHP-67 | 171 | VDGLSFGDIEGVKKIDV | 0.15% |
| NHP-68 | 172 | VYLTSFGDIEGVKKIDV | 0.15% |
| NHP-69 | 173 | VYMFSFGDIGGVKKIDV | 0.15% |
| NHP-70 | 174 | VYGLSLGDIQGVKKIDV | 0.11% |

TABLE 7-continued

CDR3s of F12 Variants from in vivo selection in non-human primates

| Clone ID | SEQ. ID NO. | CDR3 | % in R3 |
|---|---|---|---|
| NHP-71 | 175 | VNGLSSGDIEGVKKIDV | 0.10% |
| NHP-72 | 176 | VNGLSFGDIEGVGKIDV | 0.10% |
| NHP-73 | 177 | VWGLSFGDIEGRKKIDV | 0.10% |
| NHP-74 | 178 | VYGLVFGDIEGRKKIDV | 0.09% |
| NHP-75 | 179 | VYGLSFGTIGGVKKIDV | 0.09% |
| NHP-76 | 180 | VYGLSFSKIEGVKKIDV | 0.08% |
| NHP-77 | 181 | VLGLKFGQIEGVKMIDV | 0.07% |
| NHP-78 | 182 | VYGLSFGDNEGVKKIDV | 0.06% |
| NHP-79 | 183 | VFNLSFGDIEGVKKIDV | 0.05% |
| NHP-80 | 184 | VVGLSLGDIEGVKKIDV | 0.05% |

TABLE 8

CDR3s of F12 Variants from in vivo selection in Rat

| Clone ID | SEQ. ID NO. | CDR3 | % in R3 |
|---|---|---|---|
| Rat-1 | 185 | VYGLKFGDIEGVKKIDV | 0.16% |
| Rat-2 | 186 | VYGLLFGDIEGVKKIDV | 0.14% |
| Rat-3 | 187 | VYGLSIGDIEGVKKIDV | 0.11% |
| Rat-4 | 188 | VYGLSFLDIEGVKKIDV | 0.11% |
| Rat-5 | 189 | VYGLSFGDIKGVKKIDV | 0.07% |
| Rat-6 | 190 | VTGLSFGDIEGVKKIDV | 0.07% |
| Rat-7 | 191 | VSGMSFGDIEGVKKIDV | 0.07% |
| Rat-8 | 192 | VKGLSFGDIEGVKKIDV | 0.06% |
| Rat-9 | 193 | VWGLSFGDIEGVKKIDV | 0.06% |
| Rat-10 | 194 | VYGLSFGDIEEVKKIDV | 0.06% |
| Rat-11 | 195 | VYGLSTGDIEGVKKIDV | 0.05% |
| Rat-12 | 196 | VYGLSFGRIEGVKKIDV | 0.05% |
| Rat-13 | 197 | VFQLSFGDIEGVKKIDV | 0.05% |
| Rat-14 | 198 | VMGLSFGDIEGVKKIDV | 0.05% |
| Rat-15 | 199 | VYGMSFGDLEGVKKIDV | 0.04% |
| Rat-16 | 200 | VYGLSFGDDSGVKKIDV | 0.04% |
| Rat-17 | 201 | VYGLSFGDIEGGKKIDV | 0.03% |
| Rat-18 | 202 | VYGLSFGMIWGVKKIDV | 0.03% |
| Rat-19 | 203 | VYGLSFEDFEGVKKIDV | 0.03% |
| Rat-20 | 204 | VYGLSFGDIEGVGKIDV | 0.03% |
| Rat-21 | 205 | VYGLSFSDIEGVKKIDV | 0.03% |
| Rat-22 | 206 | VLGLSFGDIEGRKKIDV | 0.02% |
| Rat-23 | 207 | VNGLSFKDIEGVKKIDV | 0.02% |
| Rat-24 | 208 | VYGLSFGDLWGVKKIDV | 0.02% |
| Rat-25 | 209 | VYGMSFGDSWGVKKIDV | 0.02% |
| Rat-26 | 210 | VYGLSGGDIEGVKKIDV | 0.02% |
| Rat-27 | 211 | VYGLSLGRIEGVKKIDV | 0.02% |
| Rat-28 | 212 | VYQWLFGDIEGVKKIDV | 0.02% |
| Rat-29 | 213 | VFGKSFGEIEGVKKIDV | 0.02% |
| Rat-30 | 214 | VFGLSFGLIEGVKKIDV | 0.02% |
| Rat-31 | 215 | VNGLSIGDIEGYKKIDV | 0.02% |
| Rat-32 | 216 | VTGLSFGDINGVKKIDV | 0.02% |
| Rat-33 | 217 | VYGGSFGDIMGVKKIDV | 0.02% |
| Rat-34 | 218 | VYGLSFGDIEFVKKIDV | 0.02% |
| Rat-35 | 219 | VYGLSFGDIPGVKKIDV | 0.02% |
| Rat-36 | 220 | VYGLSFGPHEGVKKIDV | 0.02% |
| Rat-37 | 221 | VYGLSMGDILGVKKIDV | 0.02% |
| Rat-38 | 222 | VYGLVFGDIEGVKTIDV | 0.02% |
| Rat-39 | 223 | VYLLSFGFIEGVKKIDV | 0.02% |
| Rat-40 | 224 | VFGLSFGDIRGVKKIDV | 0.02% |
| Rat-41 | 225 | VFGLSFGDIWGVKKIDV | 0.02% |
| Rat-42 | 226 | VIGWSFWDIEGVKKIDV | 0.02% |
| Rat-43 | 227 | VIQLSFGDIEGVKKIDV | 0.02% |
| Rat-44 | 228 | VLGGSFGDIEGVKKIDV | 0.02% |
| Rat-45 | 229 | VRGLSFGDIEGVRKIDV | 0.02% |
| Rat-46 | 230 | VYGLSDGDIWGVKKIDV | 0.02% |
| Rat-47 | 231 | VYGLSFEGIEGAKKIDV | 0.02% |
| Rat-48 | 232 | VYGLSFGDYWGVKKIDV | 0.02% |
| Rat-49 | 233 | VYGLSFGWIWGVKKIDV | 0.02% |
| Rat-50 | 234 | VYGLSFLWIEGVKKIDV | 0.02% |
| Rat-51 | 235 | VYGLSNGDIEGVKDIDV | 0.02% |
| Rat-52 | 236 | VYLLLWGDIEGVKKIDV | 0.02% |

TABLE 9

CDR3 of F12 Variants from in vivo selection in Mouse

| Clone ID | SEQ. ID NO. | CDR3 | % in R3 |
|---|---|---|---|
| Ms-1 | 237 | VHGLSFLDIEGVKKIDV | 0.14% |
| Ms-2 | 238 | VYGLSIGDYEGVKKIDV | 0.14% |
| Ms-3 | 239 | VLGLSFGAIEGVKKIDV | 0.13% |
| Ms-4 | 240 | VWFLSFGWIEGVKKIDV | 0.12% |
| Ms-5 | 241 | VYGLEFGDIEGVKKIDV | 0.12% |
| Ms-6 | 242 | VYSLSVGDIEGVIKIDV | 0.12% |
| Ms-7 | 243 | VVYGSFGDIEGVKKIDV | 0.12% |
| Ms-8 | 244 | VIGLSFGDIEGVKKIDV | 0.11% |
| Ms-9 | 245 | VYGFFEGDIEGVKKIDV | 0.10% |
| Ms-10 | 246 | VYGLLYGDFEGHKKIDV | 0.10% |
| Ms-11 | 247 | VYGLSFGFNEGVKKIDV | 0.10% |
| Ms-12 | 248 | VYGLSKGDIRGVKKIDV | 0.10% |
| Ms-13 | 249 | VYGLSSGDLEGVKKIDV | 0.10% |
| Ms-14 | 250 | VYQLSIGDIEGVKKIDV | 0.10% |
| Ms-15 | 251 | VFGLSFGRIEGVKKIDV | 0.09% |
| Ms-16 | 252 | VYGLSFGEIEGVKKIDV | 0.09% |
| Ms-17 | 253 | VYGLSLLDIEGVKKIDV | 0.09% |
| Ms-18 | 254 | VYGLWLGDIEGVKKIDV | 0.09% |
| Ms-19 | 255 | VYGESFGDIEGVKKIDV | 0.08% |
| Ms-20 | 256 | VYGLSFGDIRGVKRIDV | 0.08% |
| Ms-21 | 257 | VYGLWFGDIEGVNKIDV | 0.08% |
| Ms-22 | 258 | VYGMSFGDIEGWKKIDV | 0.08% |
| Ms-23 | 259 | VYGMSFGFIEGVKKIDV | 0.08% |
| Ms-24 | 260 | VFGLSFGDIEQVKKIDV | 0.07% |
| Ms-25 | 261 | VFGWFFGDIEGVKKIDV | 0.07% |
| Ms-26 | 262 | VHGLSFRDMEGVKKIDV | 0.07% |
| Ms-27 | 263 | VIGILFGDIEGVKKIDV | 0.07% |
| Ms-28 | 264 | VYELFFGDQEGVKKIDV | 0.07% |
| Ms-29 | 265 | VYFLSFGDSEGVKKIDV | 0.07% |
| Ms-30 | 266 | VYGFSFGDWEGVKKIDV | 0.07% |
| Ms-31 | 267 | VYGLKWGDIEGVKKIDV | 0.07% |
| Ms-32 | 268 | VYGLQLGDIEGVKKIDV | 0.07% |
| Ms-33 | 269 | VYGLSFEDIMGVKKIDV | 0.07% |
| Ms-34 | 270 | VYGLSFGDIEFMKKIDV | 0.07% |
| Ms-35 | 271 | VYGLSFGDINGVKKIDV | 0.07% |
| Ms-36 | 272 | VYGSSFGDIEGRKKIDV | 0.07% |
| Ms-37 | 273 | VKGLSFGDLEGVKKIDV | 0.06% |
| Ms-38 | 274 | VNGLSQGDIEWVKKIDV | 0.06% |
| Ms-39 | 275 | VNGLSTGDQEGVKKIDV | 0.06% |
| Ms-40 | 276 | VTGLSKGDIHGVKKIDV | 0.06% |
| Ms-41 | 277 | VYGIIEGDIEGVKKIDV | 0.06% |
| Ms-42 | 278 | VYGLSSGSIPGVKKIDV | 0.06% |
| Ms-43 | 279 | VYGLSYRDIEGVKKIDV | 0.06% |
| Ms-44 | 280 | VYGLTYKDIEGVKKIDV | 0.06% |
| Ms-45 | 281 | VYKLLVGDIEGVKKIDV | 0.06% |
| Ms-46 | 282 | VYKWMFGDIEGVKWIDV | 0.06% |
| Ms-47 | 283 | VYMLFFGDREGVKKIDV | 0.06% |
| Ms-48 | 284 | VYQLVLGDIEGVKKIDV | 0.06% |
| Ms-49 | 285 | VFGLSFGDIMGVKHIDV | 0.06% |
| Ms-50 | 286 | VFGLSFGSIEGVKKIDV | 0.06% |
| Ms-51 | 287 | VKQLSLGDIEGVKKIDV | 0.06% |
| Ms-52 | 288 | VYGLAYGFIEGVKKIDV | 0.06% |
| Ms-53 | 289 | VYGLKFGDIERVKKIDV | 0.06% |
| Ms-54 | 290 | VYGLMMGDIEGVKKIDV | 0.06% |
| Ms-55 | 291 | VYGLSFGDFEGVKQIDV | 0.06% |
| Ms-56 | 292 | VYGLSFGDHFTVKKIDV | 0.06% |
| Ms-57 | 293 | VYGLSFGDIELVAKIDV | 0.06% |
| Ms-58 | 294 | VYGLSVMDIEGVKKIDV | 0.06% |
| Ms-59 | 295 | VYGLVFGDDEGVKKIDV | 0.06% |
| Ms-60 | 296 | VYGLVIGDIQGVKKIDV | 0.06% |
| Ms-61 | 297 | VYGMSFGEIEGVKKIDV | 0.06% |
| Ms-62 | 298 | VYGMSLGDIEGEKKIDV | 0.06% |
| Ms-63 | 299 | VYQLSLGDIEGVKKIDV | 0.06% |
| Ms-64 | 300 | VFGLSFMDLEGVKKIDV | 0.05% |
| Ms-65 | 301 | VFSLSYWDIEGVKKIDV | 0.05% |
| Ms-66 | 302 | VKQPSFGDIEGVKKIDV | 0.05% |
| Ms-67 | 303 | VQGLSDGDIEGVKKIDV | 0.05% |
| Ms-68 | 304 | VSGMLFGDINGVKGIDV | 0.05% |
| Ms-69 | 305 | VYGKSFGDMWGVKKIDV | 0.05% |
| Ms-70 | 306 | VYGLGFGDIEGYKKIDV | 0.05% |
| Ms-71 | 307 | VYGLLNGDIEGNKKIDV | 0.05% |
| Ms-72 | 308 | VYGLSFGDHNGWKKIDV | 0.05% |
| Ms-73 | 309 | VYGLSFGDYRGVKKIDV | 0.05% |

TABLE 9-continued

CDR3 of F12 Variants from in vivo selection in Mouse

| Clone ID | SEQ. ID NO. | CDR3 | % in R3 |
|---|---|---|---|
| Ms-74 | 310 | VYGLSFGFTEEVKKIDV | 0.05% |
| Ms-75 | 311 | VYGLSFGWIRGVKKIDV | 0.05% |
| Ms-76 | 312 | VYGLSFGWYAGVKKIDV | 0.05% |
| Ms-77 | 313 | VYGLSFWDIGGVKKIDV | 0.05% |
| Ms-78 | 314 | VYGLSILDIEGVKKIDV | 0.05% |
| Ms-79 | 315 | VYGLSLMDLEGVKKIDV | 0.05% |
| Ms-80 | 316 | VYGLSMGDIEGVKDIDV | 0.05% |
| Ms-81 | 317 | VYGLSWGDIEGGKKIDV | 0.05% |
| Ms-82 | 318 | VYGVFFKDIEGVKKIDV | 0.05% |
| Ms-83 | 319 | VYVLSFMDIEGVKKIDV | 0.05% |
| Ms-84 | 320 | VFGLSFGDIEKVKKIDV | 0.04% |
| Ms-85 | 321 | VTGLSFGDIEGVNKIDV | 0.04% |
| Ms-86 | 322 | VYGISFGWIEGVKKIDV | 0.04% |
| Ms-87 | 323 | VYGLEFGDIDGVKKIDV | 0.04% |
| Ms-88 | 324 | VYGLSEGDIKGVKKIDV | 0.04% |
| Ms-89 | 325 | VYGLSFGDIEGVKGIDV | 0.04% |
| Ms-90 | 326 | VYGLSFGLIMGVKKIDV | 0.04% |
| Ms-91 | 327 | VYGLSFGVIEGVKTIDV | 0.04% |
| Ms-92 | 328 | VYGLSFIDIYGVKKIDV | 0.04% |
| Ms-93 | 329 | VYGLSLGDIEGVVKIDV | 0.04% |
| Ms-94 | 330 | VYGLSLGDYEGIKKIDV | 0.04% |
| Ms-95 | 331 | VYGLSLGQIEGVKKIDV | 0.04% |
| Ms-96 | 332 | VYGLSPLDIEGVKKIDV | 0.04% |
| Ms-97 | 333 | VYGLTAGLIEGVKKIDV | 0.04% |
| Ms-98 | 334 | VYGLYFGQIEKVKKIDV | 0.04% |
| Ms-99 | 335 | VYLLFFGDSEGVKKIDV | 0.04% |
| Ms-100 | 336 | VYNLFFGDFEGVKKIDV | 0.04% |
| Ms-101 | 337 | VYQLSFGDFEEVKKIDV | 0.04% |
| Ms-102 | 338 | VFKLSFGDIEGVKKIDV | 0.03% |
| Ms-103 | 339 | VLFLSFGDIEGVKKIDV | 0.03% |
| Ms-104 | 340 | VSGLSFGDIPGVKKIDV | 0.03% |
| Ms-105 | 341 | VYFLSFGDIAGVKKIDV | 0.03% |
| Ms-106 | 342 | VYFLSFLDIEGVKKIDV | 0.03% |
| Ms-107 | 343 | VYGFSMGDIEGVKKIDV | 0.03% |
| Ms-108 | 344 | VYGLSFGWDEGVKKIDV | 0.03% |
| Ms-109 | 345 | VYGLTFGLIMGVKKIDV | 0.03% |
| Ms-110 | 346 | VYGRSFGDIEHVKKIDV | 0.03% |
| Ms-111 | 347 | VYQLSLGTIEGVKKIDV | 0.03% |
| Ms-112 | 348 | VYQLSMGDIEGLKKIDV | 0.03% |
| Ms-113 | 349 | VDGLSFWDWEGVKKIDV | 0.02% |
| Ms-114 | 350 | VEGLSFGDIWGVKKIDV | 0.02% |
| Ms-115 | 351 | VIGRSFGDIEGVKKIDV | 0.02% |
| Ms-116 | 352 | VQWLSFGDIEGVKEIDV | 0.02% |
| Ms-117 | 353 | VYGLPFGFTEGVKKIDV | 0.02% |
| Ms-118 | 354 | VYGLSFGSFFGVKKIDV | 0.02% |
| Ms-119 | 355 | VYGLTFGMIMGVKKIDV | 0.02% |
| Ms-120 | 356 | VYGRSFGDKGGVKKIDV | 0.02% |
| Ms-121 | 357 | VYGVSFGDIEGMKKIDV | 0.02% |
| Ms-122 | 358 | VYGWSYGDIEGVKKIDV | 0.02% |
| Ms-123 | 359 | VYKLSYLDIEGVKKIDV | 0.02% |
| Ms-124 | 360 | VYLQSFGDIEGVMKIDV | 0.02% |
| Ms-125 | 361 | VYGFSFGSIEGVKKIDV | 0.02% |

REFERENCES

The following references are cited
(1) Pardridge, W. M. In: Brain drug targeting, the future of brain drug development; Cambridge University Press, Cambridge, UK, 2001; Vol. 1, pp 112.
(2) Pardridge, W. M.; Oldendorf, W. H. Transport of metabolic substrates through the blood brain barrier. J. Neurochem. 1977, 28, 5-12.
(3) Boado R J, Li J Y, Nagaya M, Zhang C, Pardridge W M (1999). "Selective expression of the large neutral amino acid transporter at the blood-brain barrier". Proc. Natl. Acad. Sci. U.S.A. 96 (21): 12079-84.
(4) Hawkins, R. A.; O'Kane, R. L.; Simpson, I. A.; Vina, J. R. Structure of the blood-brain barrier and its role in the transport of amino acids. J. Nutr. 2006, 136, 218S-226S.
(5) Pardridge, W. M.; Drug transport across the blood-brain barrier. Journal of Cerebral Blood Flow & Metabolism (2012) 32, 1959-1972.
(6) Fotiadis D, Kanai Y, Palacin M. The SLC3 and SLC7 families of amino acid transporters. Mol Aspects Med. 2013 April-June; 34(2-3):139-58
(7) Feral, C. C., Nishiya, N., Fenczik, C. A., Stuhlmann, H., Slepak, M., and Ginsberg, M. H. (2005) CD98hc (SLC3A2) mediates integrin signaling. Proc. Natl. Acad. Sci. U.S.A. 102, 355-360.
(8) Cantor, J. M., and Ginsberg, M. H. (2012) CD98 at the crossroads of adaptive immunity and cancer. J. Cell Sci. 125, 1373-1382.
(9) Ip H, Sethi T. CD98 signals controlling tumorigenesis. Int J Biochem Cell Biol. 2016 December; 81(Pt A): 148-150.

(10) Killian D M, Hermeling S, Chikhale P J. Targeting the cerebrovascular large neutral amino acid transporter (LAT1) isoform using a novel disulfide-based brain drug delivery system. Drug Deliv 2007; 14: 25-31.
(11) Gynther, M.; Lathe, K.; Ropponen, J.; Leppanen, J.; Mannila, A.; Nevalainen, T.; Savolainen, J.; Jarvinen, T.; Rautio, J. Large neutral amino acid transporter enables brain drug delivery via prodrugs. J. Med. Chem. 2008, 51, 932-936.
(12) Zuchero Y J, Chen X, Bien-Ly N, et al. Discovery of novel blood-brain barrier targets to enhance brain uptake of therapeutic antibodies. Neuron. 2016 Jan. 6; 89(1):70-82.
(13) Pardridge W M (2016) Re-engineering therapeutic antibodies for Alzheimer's disease as blood-brain barrier penetrating bi-specific antibodies, Expert Opinion on Biological Therapy, 16:12, 1455-1468.
(14) Yu Y J, Zhang Y, Kenrick M, Hoyte K, Luk W, Lu Y, Atwal J, Elliott J M, Prabhu S, Watts R J, Dennis M S. Boosting brain uptake of a therapeutic antibody by reducing its affinity for a transcytosis target. Sci Transl Med. 2011 May 25; 3(84):84ra44.
(15) Niewoehner J, Bohrmann B, Collin L, Urich E, Sade H, Maier P, Rueger P, Stracke J O, Lau W, Tissot A C, Loetscher H, Ghosh A, Freskgard P O. Increased brain penetration and potency of a therapeutic antibody using a monovalent molecular shuttle. Neuron. 2014 Jan. 8; 81(1):49-60.
(16) Greenberg A S, Avila D, Hughes M, Hughes A, McKinney E C, Flajnik M F. A new antigen receptor gene family that undergoes rearrangement and extensive somatic diversification in sharks. Nature 1995; 374:168-73.
(17) Nuttall S D, Walsh R B. Display scaffolds: protein engineering for novel therapeutics. Curr Opin Pharmacol 2008; 8:609-15.
(18) Stanfield R L, Dooley H, Verdino P, Flajnik M F, Wilson I A. Maturation of shark single-domain (IgNAR) antibodies: evidence for induced-fit binding. J Mol Biol. 2007 Mar. 23; 367(2):358-72.
(19) Kovalenko O V, Olland A, Piché-Nicholas N, Godbole A, King D, Svenson K, Calabro V, Müller M R, Barelle C J, Somers W, Gill D S, Mosyak L, Tchistiakova L. Atypical antigen recognition mode of a shark immunoglobulin new antigen receptor (IgNAR) variable domain characterized by humanization and structural analysis. J Biol Chem. 2013 Jun. 14; 288(24):17408-19.
(20) Stanfield R L, Dooley H, Flajnik M F, Wilson I A. Crystal structure of a shark single-domain antibody V region in complex with lysozyme. Science 2004; 305: 1770-3.
(21) Zielonka S, Empting M, Grzeschik J, Konning D, Barelle C J, Kolmar H. Structural insights and biomedical potential of IgNAR scaffolds from sharks. MAbs. 2015; 7(1):15-25.
(22) Diaz et al., 2002—Immunogenetics (2002) 54:501-512).
(23) Streltsov et al. PNAS 2004; 101:12444-9.
(24) Liu et al., 2007—Molecular immunology 2007; 44:1775-83.
(25) Feng et al., Antibody Therapeutics, 2019, Vol. 2, No. 1 1-11 doi:10.1093/abt/tby011).
(26) Muller et al., 2012—mAbs 4:6, 673-685.
(27) Weiner L, Cell 148: 1081-4 (2012).
(28) Ahmad Z et al., Clin Dev Immunol 2012: 980250 (2012).

We claim:

1. An isolated CD98hc-specific binding moiety comprising a Type IV VNAR domain capable of specifically binding to human CD98hc and murine CD98hc, wherein said VNAR domain is represented by the formula, from N to C terminus,

FW1-CDR1-FW2-HV2-FW2'-HV4-FW3-CDR3-FW4, wherein CDR1 comprises the amino acid sequence VHGRALA (SEQ ID NO: 38), HV2 comprises the amino acid sequence TREETISKG (SEQ ID NO: 1), HV4 comprises the amino acid sequence NSGSKS (SEQ ID NO: 3), and CDR3 comprises the amino acid sequence of any one of SEQ ID NOS: 92 or 98-361.

2. The binding moiety of claim 1, wherein the Type IV VNAR domain comprises the amino acid sequence for FW1, FW2, FW2', FW3, and FW4 of SEQ ID NO: 20.

3. A conjugate comprising the binding moiety of claim 1 operably linked to a heterologous molecule which differs in biological activity from said moiety.

4. A pharmaceutical composition comprising a CD98hc binding moiety of claim 1 or a conjugate thereof and a pharmaceutically-acceptable carrier.

5. A kit for detecting or quantifying CD98hc in a sample which comprises at least one CD98hc binding moiety of claim 1 or a conjugate thereof and one or more reagents for detecting or quantifying CD98hc in said sample.

6. A vector comprising a nucleic acid molecule encoding at least one binding moiety of claim 1 or a conjugate thereof and expression control sequences to enable expression of the nucleic acid molecule in a host cell to thereby produce said at least one binding moiety or conjugate thereof.

7. The isolated CD98hc-specific binding moiety of claim 1, wherein CDR1 has the amino acid sequence SEQ. ID NO: 38 and CDR3 has the amino acid sequence SEQ. ID NO: 92.

8. The isolated CD98hc-specific binding moiety of claim 7, wherein said Type IV VNAR domain comprises the amino acid sequence SEQ ID NO: 20.

9. A conjugate comprising the binding moiety of claim 7 operably linked to a heterologous molecule which differs in biological activity from said moiety.

10. A pharmaceutical composition comprising a CD98hc binding moiety of claim 7 or a conjugate thereof and a pharmaceutically-acceptable carrier.

11. A kit for detecting or quantifying CD98hc in a sample which comprises at least one CD98hc binding moiety of claim 7 or a conjugate thereof and one or more reagents for detecting or quantifying CD98hc in said sample.

12. A vector comprising a nucleic acid molecule encoding at least one binding moiety of claim 7 or a conjugate thereof and expression control sequences to enable expression of the nucleic acid molecule in a host cell to thereby produce said at least one binding moiety or conjugate thereof.

13. A vector comprising a nucleic acid molecule encoding at least one binding moiety of claim 8 or a conjugate thereof and expression control sequences to enable expression of the nucleic acid molecule in a host cell to thereby produce said at least one binding moiety or conjugate thereof.

14. A conjugate comprising the binding moiety of claim 8 operably linked to a heterologous molecule which differs in biological activity from said moiety.

15. A pharmaceutical composition comprising a CD98hc binding moiety of claim 8 or a conjugate thereof of and a pharmaceutically-acceptable carrier.

16. A kit for detecting or quantifying CD98hc in a sample which comprises at least one CD98hc binding moiety of claim 8 or a conjugate of thereof and one or more reagents for detecting or quantifying CD98hc in said sample.

* * * * *